(12) United States Patent
Todd et al.

(10) Patent No.: US 6,716,878 B1
(45) Date of Patent: Apr. 6, 2004

(54) ANTIMICROBIAL AGENTS

(75) Inventors: Richard Simon Todd, Oxford (GB); Daniel Christopher Brookings, Oxford (GB); Helen Katherine Smith, Oxford (GB); Alison Jane Thompson, Oxford (GB); Raymond Paul Beckett, Oxford (GB)

(73) Assignee: Vernalis (Oxford) Limited (GB)

( * ) Notice: Subject to any disclaimer, the term of this patent is extended or adjusted under 35 U.S.C. 154(b) by 0 days.

(21) Appl. No.: 09/958,099

(22) PCT Filed: Apr. 10, 2000

(86) PCT No.: PCT/GB00/01337

§ 371 (c)(1),
(2), (4) Date: Oct. 5, 2001

(87) PCT Pub. No.: WO00/61134

PCT Pub. Date: Oct. 19, 2000

(30) Foreign Application Priority Data

Apr. 9, 1999 (GB) .............................................. 9907981
Aug. 11, 1999 (GB) .............................................. 9918984
Nov. 16, 1999 (GB) .............................................. 9927089

(51) Int. Cl.[7] ........................ A61K 31/19; A61K 31/13; C07C 259/04; C07C 239/00
(52) U.S. Cl. ........................ 514/575; 562/621; 562/622; 562/623; 514/645; 564/300
(58) Field of Search ................................ 514/575, 645; 562/621, 622, 623; 564/300

(56) References Cited

U.S. PATENT DOCUMENTS

| | | | |
|---|---|---|---|
| 3,166,587 A | | 1/1965 | Bernstein et al. |
| 4,618,708 A | * | 10/1986 | Roques et al. ............... 562/448 |
| 4,738,803 A | * | 4/1988 | Roques et al. ............... 562/623 |
| 4,996,358 A | * | 2/1991 | Handa et al. ................ 562/621 |
| 5,691,382 A | * | 11/1997 | Crimmin et al. ............. 514/575 |
| 6,456,468 B1 | * | 9/2002 | Hayashi ...................... 360/324.1 |
| 6,458,779 B1 | * | 10/2002 | Faller et al. ................. 514/209 |
| 6,495,597 B1 | * | 12/2002 | Ayscough et al. .......... 514/538 |
| 6,500,983 B2 | * | 12/2002 | Kottirsch et al. ............ 562/621 |
| 6,511,990 B1 | * | 1/2003 | Breslow et al. .............. 514/314 |
| 6,545,051 B1 | * | 4/2003 | Hunter et al. ................ 514/575 |
| 6,552,223 B1 | * | 4/2003 | Cartwright et al. .......... 562/621 |
| 6,576,628 B1 | * | 6/2003 | Grams et al. ............... 514/228.2 |
| 6,610,729 B1 | * | 8/2003 | Gotou et al. ................ 514/419 |

FOREIGN PATENT DOCUMENTS

| | | |
|---|---|---|
| FR | 2353289 | 12/1977 |
| WO | 95/33709 | 12/1995 |
| WO | 97/03783 | 2/1997 |
| WO | 99/39704 | 8/1999 |

OTHER PUBLICATIONS

Frechette, Roger et al. "Screening, preparation, and use of peptide deformylase inhibitors as antibacterial agents", CA135:486, 2001.*

John P. Delvin, et al.: "Studies Concerning the Antibiotic Actinonin. Part III. Synthesis of Structural Analogues of Actinonin by the Anhydride–Imide Method" Journal of the Chemical Society, Perkin Transactions I, 1975, pp. 830–841, XP002141667.

* cited by examiner

Primary Examiner—Deborah C. Lambkin
(74) Attorney, Agent, or Firm—Banner & Witcoff Ltd.

(57) ABSTRACT

Compounds of formula (I) are antibacterial agents:

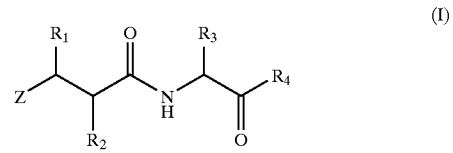

(I)

wherein Z represents a radical of formula —N(OH)CH(=O) or of formula —C(=O)NH(OH), and $R_1$–$R_4$ are as defined in the specification. A method for the treatment of bacterial or protozoal infections in humans and non-human mammals, which comprises administering to a subject suffering such infection an antibacterially or antiprotozoally effective dose of a compound of formula (I) or a pharmaceutically or veterinarily acceptable salt, hydrate or solvate thereof.

24 Claims, No Drawings

US 6,716,878 B1

ANTIMICROBIAL AGENTS

This is a U.S. National Phase Application Under 35 USC 371 and applicant herewith claims the benefit of priority of PCT/GB00/01337 filed Apr. 10, 2000, which was published under PCT Article 21(2) in English and Application No. 9907981.6 filed in Great Britain on Apr. 9, 1999, Application No. 9918984.7 filed in Great Britain on Aug. 11, 1999, Application No. 9927089.4 filed in Great Britain on Nov. 16, 1999.

This invention relates to a novel class of hydroxamic acid and N-formyl hydroxylamine derivatives having antibacterial activity, and to pharmaceutical and veterinary compositions comprising such compounds.

BACKGROUND TO THE INVENTION

In general, bacterial pathogens are classified as either Gram-positive or Gram-negative. Many antibacterial agents (including antibiotics) are specific against one or other Gram-class of pathogens. Antibacterial agents effective against both Gram-positive and Gram-negative pathogens are therefore generally regarded as having broad spectrum activity.

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as Staphylococci, Streptococci, Mycobacteria and Enterococci, resistant strains have evolved/arisen which makes them particularly difficult to eradicate. Examples of such strains are methicillin resistant *Staphylococcus aureus* (MRSA), methicillin resistant coagulase negative Staphylococci (MRCNS), penicillin resistant *Streptococcus pneumoniae* and multiply resistant *Enterococcus faecium*.

Pathogenic bacteria are often resistant to the aminoglycoside, μ-lactam (penicillins and cephalosporins), and chloramphenicol types of antibiotic. This resistance involves the enzymatic inactivation of the antibiotic by hydrolysis or by formation of inactive derivatives. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of enterococci (Woodford N. 1998 Glycopeptide-resistant enterococci: a decade of experience. Journal of Medical Microbiology. 47(10):849–62). Vancomycin-resistant enterococci are particularly hazardous in that they are frequent causes of hospital based infections and are inherently resistant to most antibiotics. Vancomycin works by binding to the terminal D-Ala-D-Ala residues of the cell wall peptidoglycan precursor. The high-level resistance to vancomycin is known as VanA and is conferred by a genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant enterococci and β-lactam antibiotic-resistant bacteria, such as methicillin-resistant *Staphylococcus aureus*, is of utmost importance.

BRIEF DESCRIPTION OF THE INVENTION

This invention is based on the finding that certain hydroxamic acid and N-formyl hydroxylamine derivatives have antibacterial activity, and makes available a new class of antibacterial agents. The inventors have found that the compounds with which this invention is concerned are antibacterial with respect to a range of Gram-positive and Gram-negative organisms.

Although it may be of interest to establish the mechanism of action of the compounds with which the invention is concerned, it is their ability to inhibit bacterial growth that makes them useful. However, it is presently believed that their antibacterial activity is due, at least in part, to intracellular inhibition of bacterial polypeptide deformylase (PDF; EC 3.5.1.31).

All ribosome-mediated synthesis of proteins starts with a methionine residue. In prokaryotes the methionyl moiety carried by the initiator tRNA is N-formylated prior to its incorporation into a polypeptide. Consequently, N-formylmethionine is always present at the N-terminus of a nascent bacterial polypeptide. However, most mature proteins do not retain the N-formyl group or the terminal methionine residue. Deformylation is required prior to methionine removal, since methionine aminopeptidase does not recognise peptides with an N-terminal formylmethionine residue (Solbiati et al., J. Mol. Biol. 290:607–614, 1999). Deformylation is, therefore, a crucial step in bacterial protein biosynthesis and the enzyme responsible, PDF, is essential for normal bacterial growth. Although the gene encoding PDF (def) is present in all pathogenic bacteria for which sequences are known (Meinnel et al., J. Mol. Biol, 266:939–49, 1997), it has no eukaryotic counterpart, making it an attractive target for antibacterial chemotherapy.

The isolation and characterisation of PDF has been facilitated by an understanding of the importance of the metal ion in the active site (Groche et al., Biophys. Biochem. Res. Commun., 246:324–6, 1998). The $Fe^{2+}$ form is highly active in vivo but is unstable when isolated due to oxidative degradation (Rajagopalan et al., J. Biol. Chem. 273:22305–10, 1998). The $Ni^{2+}$ form of the enzyme has specific activity comparable with the ferrous enzyme but is oxygen-insensitive (Ragusa et al., J. Mol. Biol. 1998, 280:515–23, 1998). The $Zn^{2+}$ enzyme is also stable but is almost devoid of catalytic activity (Rajagopalan et al., J. Am. Chem. Soc. 119:12418–12419, 1997).

Several X-ray crystal structures and NMR structures of *E. coli* PDF, with or without bound inhibitors, have been published (Chan et al., Biochemistry 36:13904–9, 1997; Becker et al., Nature Struct. Boil. 5:1053–8, 1998; Becker et al., J. Biol. Chem. 273:11413–6, 1998; Hao et al., Biochemistry, 38:4712–9, 1999; Dardel et al., J. Mol. Biol. 280:501–13, 1998; O'Connell et al., J. Biomol. NMR, 13:311–24, 1999), indicating similarities in active site geometry to metalloproteinases such as thermolysin and the metzincins.

Recently the substrate specificity of PDF has been extensively studied (Ragusa et al., J. Mol. Biol. 289:1445–57, 1999; Hu et al., Biochemistry 38:643–50, 1999; Meinnel et al., Biochemistry, 38:4287–95, 1999). These authors conclude that an unbranched hydrophobic chain is preferred at P1', while a wide variety of P2' substituents are acceptable and an aromatic substituent may be advantageous at the P3' position. There have also been reports that small peptidic compounds containing an H-phosphonate (Hu et al., Bioorg. Med. Chem. Lett., 8:2479–82, 1998) or thiol (Meinnet et al., Biochemistry, 38:4287–95, 1999) metal binding group are micromolar inhibitors of PDF. Peptide aldehydes such as calpeptin (N-Cbz-Leu-norteucinal) have also been shown to inhibit PDF (Durand et al., Arch. Biochem. Biophys., 367:297–302, 1999). However, the identity of the metal binding group and its spacing from the rest of the molecule ("recognition fragment") has not been studied extensively. Furthermore, non-peptidic PDF inhibitors, which may be desirable from the point of view of bacterial cell wall permeability or oral bioavailability in the host species, have not been identified.

Recently it has been reported that PDF is present in eukaryotic parasites such as *Plasmodium falciparum* (Ferreira et al, Parasitology Today, vol 16, no. 4, 2000). Those authors also found evidence for the presence of PDF in other parasites of humans, such as the kinetoplastid protozoan parasites *Trypanosoma brucei* and *Leishmania major*. Based on these findings, it is anticipated that the compounds with which this invention is concerned have antiprotozoal activity, and are useful in the treatment of malaria and other protozoal diseases.

Certain N-formyl hydroxylamine derivatives have previously been claimed in the patent publications listed below, although very few examples of such compounds have been specifically made and described:

| | |
|---|---|
| EP-B-0236872 | (Roche) |
| WO 92/09563 | (Glycomed) |
| WO 92/04735 | (Syntex) |
| WO 95/19965 | (Glycomed) |
| WO 95/22966 | (Sanofi Winthrop) |
| WO 95/33709 | (Roche) |
| WO 96/23791 | (Syntex) |
| WO 96/16027 | (Syntex/Agouron) |
| WO 97/03783 | (British Biotech) |
| WO 97/18207 | (DuPont Merck) |
| WO 98/38179 | (GlaxoWellcome) |
| WO 98/47863 | (Labs Jaques Logeais) |

The pharmaceutical utility ascribed to the N-formyl hydroxylamine derivatives in those publications is the ability to inhibit matrix metalloproteinases (MMPs) and in some cases release of tumour necrosis factor (TNF), and hence the treatment of diseases or conditions mediated by those enzymes, such as cancer and rheumatoid arthritis. That prior art does not disclose or imply that N-formyl hydroxylamine derivatives have antibacterial activity.

In addition to these, U.S. Pat. No. 4,738,803 (Roques et al.) also discloses N-formyl hydroxylamine derivatives, however, these compounds are disclosed as enkephalinase inhibitors and are proposed for use as antidepressants and hypotensive agents. Also, WO 97/38705 (Bristol-Myers Squibb) discloses certain N-formyl hydroxylamine derivatives as enkephalinase and angiotensin converting enzyme inhibitors. This prior art does not disclose or imply that N-formyl hydroxyiamine derivatives have antibacterial activity either.

Our copending International patent applications nos. WO 99/39704 and WO 99/59568 disclose that certain N-formyl hydroxylamine and hydroxamic acid derivatives have antibacterial activity. One class of compounds disclosed therein as having such activity has general formula (IA):

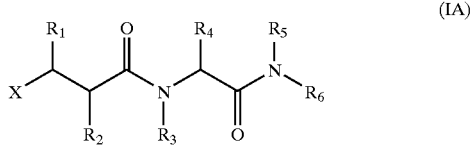

(IA)

Wherein X represents an N-formylhydroxylamino group (—N(OH)CHO) or a hydroxamic acid group (—CONHOH), and the various "R" substituents are as specified in the documents. The compounds useful in accordance with the present invention differ in structure from those of WO 99/39704 and WO 99/59568 principally in that the amido radical $R_6R_5NCO$— is replaced by a ketone radical.

Very many hydroxamic acid derivatives are known. Many have been disclosed as having matrix metalloproteinase (MMP) inhibitory activity, and thus to be potentially useful for the treatment of diseases mediated by MMPs, for example cancer, arthritides, and contitions involving tissue remodeling such as wound healing, and restenosis. However, very few such known hydroxamic acid derivatives have the ketone moiety which characterises the compounds useful according to the present invention. One publication which does, however, is WO 98/30541 (Abbott).

DETAILED DESCRIPTION OF THE INVENTION

According to the first aspect of the present invention there is provided the use of a compound of formula (I) or a pharmaceutically or veterinarily acceptable salt, hydrate or solvate thereof in the preparation of a composition for treatment of bacterial or protozoal infections in humans and non-human mammals:

(I)

wherein:
Z represents a radical of formula —N(OH)CH(═O) or formula —C(═O)NH(OH);
$R_1$ represents hydrogen, methyl or trifluoromethyl, or, except when Z is a radical of formula —N(OH)CH (═O), a hydroxy or amino group;
$R_2$ represents a group $R_{10}$—$(X)_n$—$(ALK)_m$— wherein
$R_{10}$ represents hydrogen, or a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by $(C_{1-6})$alkyl, $(C_{1-6})$alkoxy, hydroxy, mercapto, $(C_{1-6})$alkylthio, amino, halo (including fluoro, chloro, bromo and iodo), trifluoromethyl, cyano, nitro, oxo, —COOH, —$CONH_2$, —$COOR^A$, —$NHCOR^A$, —$CONHR^A$, —$NHR^A$, $NR^AR^B$, or —$CONR^AR^B$ wherein $R^A$ and $R^B$ are independently a $(C_{1-6})$alkyl group and
ALK represents a straight or branched divalent $C_{1-6}$ alkylene, $C_2$–$C_6$ alkenylene, or $C_2$–$C_6$ alkynylene radical, and may be interrupted by one or more non-adjacent —NH—, —O— or —S— linkages, X represents —NH—, —O— or —S—, and
m and n are independently 0 or 1;

$R_3$ represents the side chain of a natural or non-natural alpha amino acid; and $R_4$ represents a radical $R_5$—(ALK)$_p$— wherein ALK is as defined in relation to $R_2$, p is 0 or 1, and $R_5$ represents hydrogen, or a $C_1$–$C_6$ alkyl, $C_2$–$C_6$ alkenyl, $C_2$–$C_6$ alkynyl, cycloalkyl, aryl, or heterocyclyl group any of which (i) may be substituted by a group selected from $(C_{1-6})$ alkyl, phenyl, benzyl, $(C_{1-6})$alkoxy, phenoxy, hydroxy, mercapto, $(C_{1-6})$alkylthio, amino, halo, trifluoromethyl, cyano, nitro, oxo, —COOH, —SO$_2$H, —CONH$_2$, —SO$_2$NH$_2$, —COR$^A$, —SOR$^A$, —SO$_2$R$^A$, —SO$_3$R$^A$, —COOR$^A$, —CONHR$^A$, —SO$_2$NHR$^A$, —NHCOR$^A$, —NHSO$_2$R$^A$, and —NHR$^A$, wherein R$^A$ is $(C_{1-6})$alkyl, cycloalkyl, phenyl, 2-, 3- or 4-pyridyl, N- or 2-, 3- or 4-piperidyl, N- or 2- or 3-piperazyl group; or (ii) may be substituted by —NR$^A$R$^B$, —CONR$^A$R$^B$ or —SO$_2$NR$^A$R$^B$, wherein R$^A$ and R$^B$ are independently $(C_1$–$C_6)$alkyl, cycloalkyl, phenyl, 2-, 3- or 4-pyridyl, N- or 2-, 3- or 4-piperidyl, N- or 2- or 3-piperazyl group, or when taken together with the N atom to which they are attached R$^A$ and R$^B$ form a 5 to 7 membered aromatic or non-aromatic ring, which ring (a) may contain additional heteroatoms selected from N, O and S, and in which any S atom may be oxidised as a sulphonyl or sulphoxide, and (b) may be substituted on a ring carbon or heteroatom by one or more of the substituents listed under (i) above.

In another aspect, the invention provides a method for the treatment of bacterial or protozoal infections in humans and non-human mammals, which comprises administering to a subject suffering such infection an antibacterially effective dose of a compound of formula (I) as defined above.

In a further aspect of the invention there is provided a method for the treatment of bacterial contamination by applying an antibacterially effective amount of a compound of formula (I) as defined above to the site of contamination.

The compounds of formula (I) as defined above may be used as component(s) of antibacterial cleaning or disinfecting materials.

Compounds of formula (I) above wherein Z is a radical of formula —N(OH)CH(=O), are believed to be novel. Accordingly, in another aspect, the invention provides a compound of formula (I) wherein Z is a radical of formula —N(OH)CH(=O), or a pharmaceutically or veterinarily acceptable salt, hydrate or solvate thereof.

On the hypothesis that the compounds (I) act by inhibition of intracellular PDF, the most potent antibacterial effect may be achieved by using compounds which efficiently pass through the bacterial cell wall. Thus, compounds which are highly active as inhibitors of PDF in vitro and which penetrate bacterial cells are preferred for use in accordance with the invention. It is to be expected that the antibacterial potency of compounds which are potent inhibitors of the PDF enzyme in vitro, but are poorly cell penetrant, may be improved by their use in the form of a prodrug, ie a structurally modified analogue which is converted to the parent molecule of formula (I), for example by enzymic action, after it has passed through the bacterial cell wall. The same is true in the case of protozoa.

As used herein the term "$(C_1$–$C_6)$alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent $(C_1$–$C_6)$alkylene radical" means a saturated hydrocarbon chain having from 1 to 6 carbon atoms and two unsatisfied valencies.

As used herein the term "$(C_2$–$C_6)$alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "divalent $(C_2$–$C_6)$alkenylene radical" means a hydrocarbon chain having from 2 to 6 carbon atoms, at least one double bond, and two unsatisfied valencies.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_2$–$C_6)$alkynylene radical" means a hydrocarbon chain having from 2 to 6 carbon atoms, at least one triple bond, and two unsatisfied valencies.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "cycloalkenyl" means an unsaturated alicyclic moiety having from 3–8 carbon atoms and includes, for example, cyclopropenyl, cyclobutenyl, cyclopentenyl, cyclohexenyl, cycloheptenyl and cyclooctenyl. In the case of cycloalkenyl rings of from 5–8 carbon atoms, the ring may contain more than one double bond.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the unqualified term "heterocyclyl" or "heterocyclic" includes "heteroaryl" as defined below, and in particular means a 5–8 membered aromatic or non-aromatic heterocyclic ring containing one or more heteroatoms selected from S, N and O, and optionally fused to a benzyl or second heterocyclic ring, and the term includes, for example, pyrrolyl, furyl, thienyl, piperidinyl, imidazolyl, oxazolyl, thiazolyl, thiadiazolyl, thiazepinyl, pyrazolyl, pyridinyl, pyrrolidinyl, pyrimidinyl, morpholinyl, piperazinyl, indolyl, and benzimidazolyl rings.

As used herein the term "heteroaryl" refers to a 5- or 6-membered aromatic ring containing one or more heteroatoms, and optionally fused to a benzyl or pyridyl ring; and to groups consisting of two covalently linked 5- or 6-membered aromatic rings each containing one or more heteroatoms; and to groups consisting of a monocyclic carbocyclic aromatic group covalently linked to a 5- or 6-membered aromatic rings containing one or more heteroatoms. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl, 4-([1,2,3]-thiadiazoly-4-yl)phenyl and 5-isoxazol-3-ylthienyl.

As used herein the unqualified term "carbocyclyl" or "carbocyclic" refers to a 5–8 membered ring whose ring atoms are all carbon.

Unless otherwise specified in the context in which it occurs, the term "substituted" as applied to any moiety herein means substituted with up to four substituents, each of which independently may be $(C_1-C_6)$alkyl, phenyl, benzyl, $(C_{1-6})$alkoxy, phenoxy, hydroxy, mercapto, $(C_{1-6})$alkylthio, amino, halo (including fluoro, chloro, bromo and iodo), trifluoromethyl, cyano, nitro, oxo, —COOH, —CONH$_2$, —COR$^A$, —COOR$^A$, —NHCOR$^A$, —CONHR$^A$, —NHR$^A$, —NR$^A$R$^B$, or —CONR$^A$R$^B$ wherein R$^A$ and R$^B$ are independently a $(C_{1-6})$alkyl group. In the case where "substituted" means substituted by benzyl, the phenyl ring thereof may itself be substituted with any of the foregoing, except phenyl or benzyl.

As used herein the terms "side chain of a natural alpha-amino acid" and "side chain of a non-natural alpha-amino acid" mean the group $R^x$ in respectively a natural and non-natural amino acid of formula NH$_2$—CH(R$^x$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

In natural alpha-amino acid side chains which contain functional substituents, for example amino, carboxyl, hydroxy, mercapto, guanidyl, imidazolyl, or indolyl groups as in arginine, lysine, glutamic acid, aspartic acid, tryptophan, histidine, serine, threonine, tyrosine, and cysteine, such functional substituents may optionally be protected.

Likewise, in the side chains of non-natural alpha amino acids which contain functional substituents, for example amino, carboxyl, hydroxy, mercapto, guanidyl, imidazolyl, or indolyl groups, such functional substituents may optionally be protected.

The term "protected" when used in relation to a functional substituent in a side chain of a natural or non-natural alpha-amino acid means a derivative of such a substituent which is substantially non-functional. The widely used handbook by T. W. Greene and P. G. Wuts "Protective Groups in Organic Synthesis" Second Edition, Wiley, New York, 1991 reviews the subject. For example, carboxyl groups may be esterified (for example as a $C_{1-6}$ alkyl ester), amino groups may be converted to amides (for example as a NHCOC$_{1-6}$ alkyl amide) or carbamates (for example as an NHC(=O)OC$_{1-6}$ alkyl or NHC(=O)OCH$_2$Ph carbamate), hydroxyl groups may be converted to ethers (for example an OC$_{1-6}$ alkyl or a O(C$_{1-6}$ alkyl)phenyl ether) or esters (for example a OC(=O)C$_1$-C$_6$ alkyl ester) and thiol groups may be converted to thioethers (for example a tert-butyl or benzyl thioether) or thioesters (for example a SC(=O)C$_{1-6}$ alkyl thioester).

There are at least two actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the $R_2$ group is R; that of the carbon atom carrying the $R_1$ group (when asymmetric) is R; and that of the carbon atom carrying the $R_3$ group (when asymmetric) is S In the compounds of formula (I) as defined above:

$R_1$ is hydrogen, methyl, or trifluoromethyl. Hydrogen is currently preferred.

$R_2$ may be, for example:
optionally substituted $C_1-C_8$ alkyl, $C_3-C_6$ alkenyl, $C_3-C_6$ alkynyl or cycloalkyl;

phenyl($C_{1-6}$ alkyl)-, phenyl($C_3-C_6$ alkenyl)- or phenyl ($C_3-C_6$ alkynyl)-optionally substituted in the phenyl ring;

cycloalkyl($C_{1-6}$ alkyl)-, cycloalkyl($C_3-C_6$ alkenyl)- or cycloalkyl($C_3-C_6$ alkynyl)-optionally substituted in the cycloalkyl ring;

heterocyclyl($C_1-C_6$ alkyl)-, heterocyclyl($C_3-C_6$ alkenyl)- or heterocyclyl($C_3-C_6$ alkynyl)-optionally substituted in the heterocyclyl ring; or $CH_3(CH_2)_pO(CH_2)_q$— or $CH_3(CH_2)_pS(CH_2)_q$—, wherein p is 0, 1, 2 or 3 and q is 1, 2 or 3.

Specific examples of $R_2$ groups include
methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups at $R_2$ are n-propyl, n-butyl, n-pentyl, and cyclopentylmethyl.

$R_3$ may be, for example
the characterising group of a natural a amino acid, for example benzyl, or 4-methoxyphenylmethyl, in which any functional group may be protected, any amino group may be acylated and any carboxyl group present may be amidated; or a group -[Alk]$_n$R$_9$ where Alk is a $(C_{1-6})$alkylene or $(C_2-C_6)$alkenylene group optionally interrupted by one or more —O—, or —S— atoms or —N(R$_{12}$)— groups [where R$_{12}$ is a hydrogen atom or a $(C_{1-6})$alkyl group], n is 0 or 1, and R$_9$ is hydrogen or an optionally substituted phenyl, aryl, heterocyclyl, cycloalkyl or cycloalkenyl group or (only when n is 1) R$_9$ may additionally be hydroxy, mercapto, $(C_{1-6})$alkylthio, amino, halo, trifluoromethyl, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a $(C_1-C_6)$alkyl group; or CONH$_2$, —COOR$^A$, —NHCOR$^A$, —CONHR$^A$, —NHR$_A$, —NR$^A$R$^B$, or —CONR$^A$R$^B$ wherein R$^A$ and R$^B$ are independently a $(C_{1-6})$alkyl group; or a benzyl group substituted in the phenyl ring by a group of formula —OCH$_2$COR$_3$ where R$_8$ is hydroxyl, amino, $(C_{1-6})$alkoxy, phenyl$(C_{1-6})$alkoxy, $(C_{1-6})$alkylamino, di$((C_{1-6})$alkyl)amino, phenyl$(C_1-C_6)$alkylamino; or a heterocyclic$(C_{1-6})$alkyl group, either being unsubstituted or mono- or di-substituted in the heterocyclic ring with halo, nitro, carboxy, $(C_{1-6})$alkoxy, cyano, $(C_{1-6})$alkanoyl, trifluoromethyl $(C_{1-6})$alkyl, hydroxy, formyl, amino, $(C_{1-6})$alkylamino, di-$(C_{1-6})$alkylamino, mercapto, $(C_{1-6})$alkylthio, hydroxy$(C_{1-6})$alkyl, mercapto$(C_{1-6})$alkyl or $(C_1-C_6)$alkylphenylmethyl; or a group —CR$_a$R$_b$R$_c$ in which:
  each of R$_a$, R$_b$ and R$_c$ is independently hydrogen, (C$_1$–$_6$)alkyl, (C$_2$–C$_6$)alkenyl, (C$_2$–C$_6$)alkynyl, phenyl(C$_1$–C$_6$)alkyl, (C$_3$–C$_8$)cycloalkyl; or
  R$_c$ is hydrogen and R$_a$ and R$_b$ are independently phenyl or heteroaryl such as pyridyl; or
  R$_c$ is hydrogen, (C$_1$–C$_6$)alkyl, (C$_2$–C$_6$)alkenyl, (C$_2$–C$_8$) alkynyl, phenyl(C$_1$–C$_6$)alkyl, or (C$_3$–C$_8$)cycloalkyl, and R$_a$ and R$_b$ together with the carbon atom to which they are attached form a 3 to 8 membered cycloalkyl or a 5- to 6-membered heterocyclic ring; or
  R$_a$, R$_b$ and R$_c$ together with the carbon atom to which they are attached form a tricyclic ring (for example adamantyl); or
  R$_a$ and R$_b$ are each independently (C$_1$–$_6$)alkyl, (C$_2$–C$_6$) alkenyl, (C$_2$–C$_6$)alkynyl, phenyl(C$_1$–$_6$)alkyl, or a group as defined for R$_c$ below other hydrogen, —OH, —SH, halogen, —CN, —CO$_2$H, (C$_1$–$_4$) perfluoroalkyl, —CH$_2$OH, —CO$_2$(C$_1$–$_6$)alkyl, —O(C$_1$–$_6$)alkyl, —O(C$_2$–C$_6$)alkenyl, —S(C$_1$–C$_6$) alkyl, —SO(C$_1$–C$_6$)alkyl, —SO$_2$(C$_1$–$_6$)alkyl, —S(C$_2$–C$_6$)alkenyl, —SO(C$_2$–C$_6$)alkenyl, —SO$_2$(C$_2$–C$_6$)alkenyl or a group —Q—W wherein Q represents a bond or —O—, —S—, —SO— or —SO$_2$— and W represents a phenyl, phenylalkyl, (C$_3$–C$_8$)cycloalkyl, (C$_3$–C$_8$)cycloalkylalkyl, (C$_4$–C$_8$)cycloalkenyl, (C$_4$–C$_8$)cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$–C$_6$)alkyl, —CONH$_2$, —CONH(C$_1$–C$_6$)alkyl, —CONH (C$_1$–C$_6$alkyl)$_2$, —CHO, —CH$_2$OH, (C$_1$–C$_4$) perfluoroalkyl, —O(C$_1$–C$_6$)alkyl, —S(C$_1$–C$_6$)alkyl, —SO(C$_1$–C$_6$)alkyl, —SO$_2$(C$_1$–$_6$)alkyl, —NO$_2$, —NH$_2$, —NH(C$_1$–C$_6$)alkyl, —N((C$_1$–C$_6$)alkyl)$_2$, —NHCO(C$_1$–C$_6$)alkyl, (C$_1$–C$_6$)alkyl, (C$_2$–C$_6$) alkenyl, (C$_2$–C$_6$)alkynyl, (C$_3$–C$_8$)cycloalkyl, (C$_4$–C$_8$)cycloalkenyl, phenyl or benzyl.

Examples of particular R$_3$ groups include methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxethyl, 2-carboxyethyl, 2-methylcarbamoylethyl, 2-carbamoylethyl, and 4-aminobutyl. Presently preferred R$_3$ groups include tert-butyl.

R$_4$ may be, for example
  optionally substituted C$_1$–C$_8$ alkyl, C$_2$–C$_6$ alkenyl, C$_2$–C$_6$ alkynyl or cycloalkyl;
  optionally substituted phenyl, biphenyl or naphthyl;
  optionally substituted piperidinyl, cyclohexyl, cyclopentyl, oxazolyl, thiazepinyl, pyridinyl, pyrrolidinyl, pyrimidinyl, morpholinyl, piperazinyl, indolyl, optionally substituted piperidinyl, cyclohexyl, cyclopentyl, oxazolyl, thiazepinyl, pyridinyl, pyrrolidinyl, pyrimidinyl, morpholinyl, piperazinyl, indolyl, thienyl, furanyl, pyrrolyl, imidazolyl, benzofuranyl, benzothienyl, benzimidazolyl, thiazolyl, benzothiazolyl, pyrazolyl, isoxazolyl, isothiazolyl, triazolyl, thiadiazolyl, oxadiazolyl, pyridinyl, pyridazinyl, pyrazinyl, or triazinyl.
  phenyl(C$_1$–C$_6$ alkyl)-, phenyl(C$_2$–C$_6$ alkenyl)- or phenyl (C$_2$–C$_6$ alkynyl)-optionally substituted in the phenyl ring;
  cycloalkyl(C$_1$–C$_6$ alkyl)-, cycloalkyl(C$_2$–C$_6$ alkenyl)- or cycloalkyl(C$_2$–C$_6$ alkynyl)-optionally substituted in the cycloalkyl ring;
  heterocyclyl(C$_1$–C$_6$ alkyl)-, heterocyclyl(C$_2$–C$_6$ alkenyl)- or heterocyclyl(C$_2$–C$_6$ alkynyl)-optionally substituted in the heterocyclyl ring.

Specific examples of R$_4$ groups include

Methyl, ethyl, n-propyl, iso-propyl, cyclopropyl, cyclobutyl, cyclopentyl, cyclohexyl, 2-phenylcycloprop-1-yl, benzyl, biphenyl-2-yl, biphenyl-3-yl, biphenyl-l-4-yl, 2-methoxyphenyl, 3-methoxyphenyl, 4-methoxyphenyl, 2,3-dimethoxyphenyl, 2,4-dimethoxyphenyl, 3,4-dimethoxyphenyl, 2-phenoxyphenyl, 3-phenoxyphenyl, 4-phenoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-aminophenyl, 3-aminophenyl, 4-aminophenyl, 2-acetamidophenyl, 3-acetamidophenyl, 4-acetamidophenyl, 2-N,N-dimethylaminophenyl, 3-N,N-dimethylaminophenyl, 4-N,N-dimethylaminophenyl, 2-methanesulfonamidophenyl, 3-methanesulfonamidophenyl, 4-methanesulfonamidophenyl, 2-hydroxyphenyl, 3-hydroxyphenyl, 4-hydroxyphenyl, 2,3-dihydroxyphenyl, 2,4-dihydroxyphenyl, 3,4-dihydroxyphenyl, 2-thiophenolyl, 3-thiophenolyl, 4-thiophenolyl, 2-thioanisolyl, 3-thioanisolyl, 4-thioanisolyl, 1-naphthyl, 2-naphthyl, furan-2-yl, thien-2-yl, pyrrol-2-yl, 1-methylpyrrol-2-yl, imidazol-2-yl, 1-methylimidazol-2-yl, thiazol-2-yl, 5-phenylpyrrol-2-yl, 5-phenylfuran-2-yl, 5-phenylthien-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 1,3,4-thiadiazol-2-yl, pyridin-2-yl, pyridin-3-yl, pyridin-4-yl, N-oxides of pyridin-2-yl pyridin-3-yl and pyridin-4-yl, indol-2-yl, indol-3-yl, 1-methylindol-2-yl, 1-methylindol-3-yl, benzimidazol-2-yl, 1-methylbenzimidazol-2-yl, pyrazin-2-yl, 1,2-pyridazin-3-yl, 1,3-pyrimidin-2-yl, benzo[b]thien-2-yl, benzo[b]thien-3-yl, benzo[b]furan-2-yl, benzo[b]furan-3-yl, isoxazol-5-yl, quinolin-2-yl, quinolin-3-yl, isoquinolin-2-yl, isoquinolin-3-yl, 2-oxo-2-phenylethyl, diphenylmethyl, 4-N-methylaminophenyl, 4-N,N-dimethylcarboxamidophenyl, and 4-carboxyphenyl. R$_4$ may be a phenyl group which is substituted, for example in the 4-position, by one of the following:

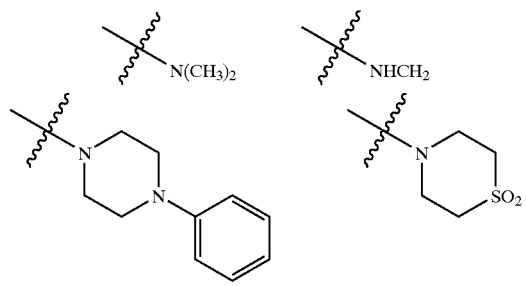

-continued

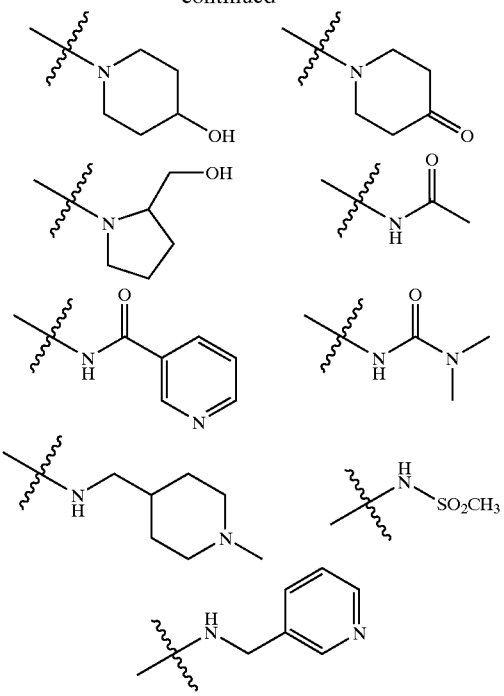

In the compounds of formula (I) as defined above wherein Z is a radical of formula —C(=O)NH(OH) the radicals $R_1$, $R_2$, $R_3$, $R_4$ may be any of those discussed above in relation to compounds (I) wherein Z is a radical of formula —N(OH)CH(=O). However, in addition, $R_1$ may be, for example, a hydroxy, methoxy, ethoxy, n-propyloxy, allyloxy, amino, methylamino, dimethylamino, ethylamino, or diethylamino group.

Specific examples of compounds of the invention include those disclosed in the Examples herein.

Compounds of the invention wherein Z is a radical of formula —N(OH)CH(=O) may be prepared by N-formylation of a compound of formula (II)

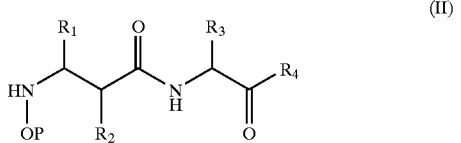

(II)

wherein —OP represents a protected hydroxy group, and $R_1$, $R_2$, $R_3$ and $R_4$ are as defined in relation to formula (I) except that any reactive groups present therein which are reactive with the formylation reagent are protected, and then converting —OP to a hydroxy group and removing any protecting groups present in $R_1$, $R_2$, $R_3$ or $R_4$. Formylacetic anhydride is a convenient formylating agent for this reaction.

Compounds of formula (II) may be synthesised from easily accessible or commercially available starting materials, or by standard synthetic routes analogous to those shown in Schemes 1 and 2 below.

Hydroxamate compounds of formula (I) for use in accordance with the invention may be prepared by reacting the parent compound wherein Z is a carboxylic acid group with hydroxylamine or an N- and/or O-protected hydroxylamine, and thereafter removing any O- or N-protecting groups.

Antibacterial or antiprotozoal compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredient(s) may be made up into a cream, lotion or ointment. Cream or ointment formulations which may be used for the drug are conventional formulations well known in the art, for example as described in standard textbooks of pharmaceutics such as the British Pharmacopoeia.

The active ingredient(s) may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle. Intra-venous infusion is another route of administration for the compounds used in accordance with the invention.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following example illustrate embodiments of the invention.

The following abbreviations have been used throughout:

| | |
|---|---|
| CDI | 1,1'-Carbonyldiimidazole |
| DMF | N,N-Dimethylformamide |
| EDC | N-Ethyl-N'-(3-dimethylaminopropyl)carbodiimide hydrochloride |
| TFA | Trifluoroacetic acid |
| HOBt | 1-Hydroxybenzotriazole |
| HPLC | High performance liquid chromatography |
| LRMS | Low resolution mass spectrometry |

| | |
|---|---|
| THF | Tetrahydrofuran |
| TLC | Thin layer chromatography |

$^1$H and $^{13}$C NMR spectra were recorded using a Bruker AC 250E spectrometer at 250.1 and 62.9 MHz, respectively. Mass spectra were obtained using a Perkin Elmer Sciex API 165 spectrometer using both positive and negative ion modes.

Where MIC values are quoted for the compounds of the examples, those results were obtained by the method described in the Biological Example.

EXAMPLE 1

2(R)-[(N-Formyl-N-hydroxyamino)-methyl]-hexanoic Acid-(1'(S)-(4-fluorobenzoyl)-2',2'-dimethylpropyl)amide

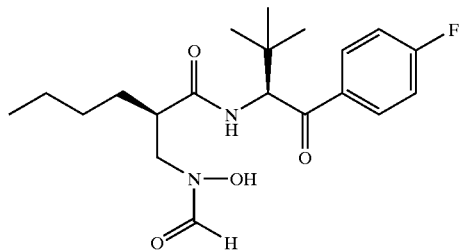

The title compound was prepared as described in Scheme 1. The experimental details of the synthesis and relevant spectroscopic data are described below.

Scheme 1

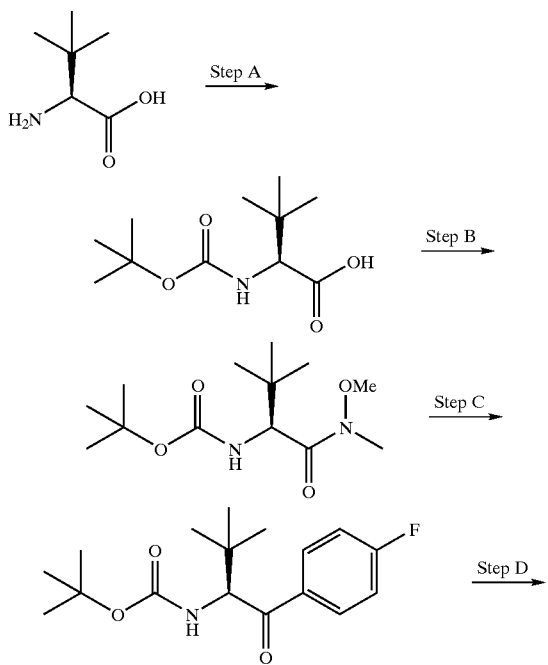

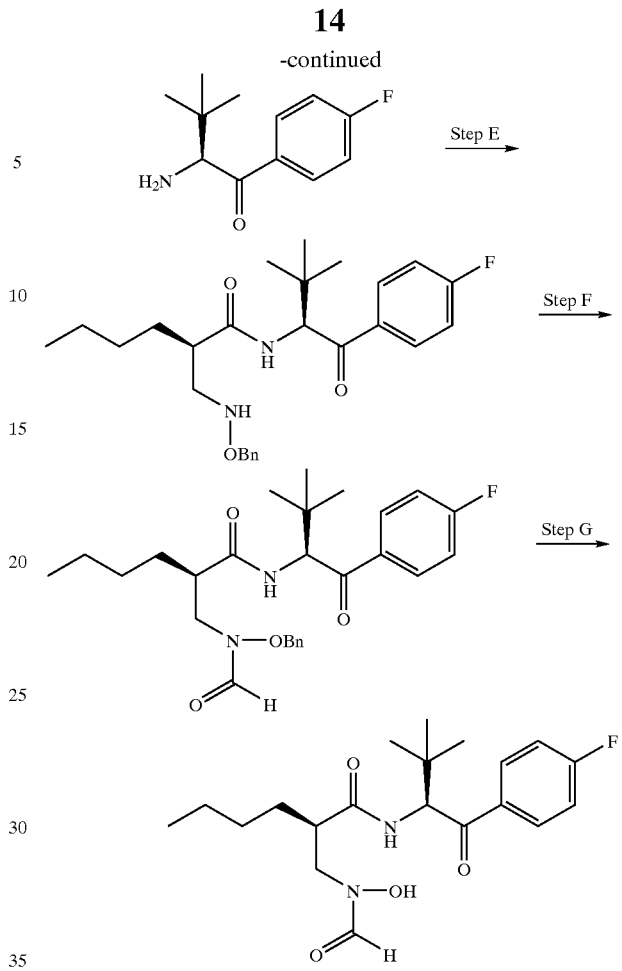

Reagents and Conditions:
A. Di-tert-butyldicarbamaye, Et$_3$N, MeOH
B. HN(OMe)Me•HCl, CDI, CH$_2$Cl$_2$
C. 4-Fluorophenylamagnesium bromide, THF, 0° C. to 25° C., 20 hours
D. TFA, CH$_2$Cl$_2$, <5° C., 16 hours
E. 2(R)-(Benzyloxy-amino-methyl)-hexanoic acid, WSC, 10 mol% HOBT, DMF, 16 hours
F. Formylacetic anhydride, CH$_2$Cl$_2$, RT, 1 hour
G. H$_2$ 10% Pd/C, EtOAc/MeOH STEP A: 2(S)-tert-Butoxycarbonylamino-3,3-dimethyl-butyric Acid To a suspension of L-tert-leucine (26.1 g, 0.2 mol) in methanol (150 mL) was added triethylamine (56 mL, 0.4 mol) and the mixture cooled to 0° C. To the mixture was added slowly a solution of di-tert-butyldicarbamate (48 g, 0.22 mol) in methanol (40 mL) such that an internal temperature of between 0 and 5° C. was maintained. The reaction was allowed to stir overnight and the solvents were removed in vacuo. The residue was dissolved in ethyl acetate (200 mL) and washed with 10% w/v aqueous citric acid solution (3×100 mL). The organic layer was dried over MgSO$_4$, filtered and the solvents removed in vacuo to give the title product as a pale yellow oil (48.9 g, >100%, residual solvent).

$^1$H NMR (CDCl$_3$): δ/ppm 9.20 (1H, bs), 5.10 (1H, m), 4.15 (1H, m), 1.45 (9H, s), 1.00 (9H, s).

STEP B: [1(S)-(Methoxy-methyl-carbamoyl)-2,2-dimethylpropyl]-carbamic Acid-tert-butyl Ester To a solution of 2(S)-tert-butoxycarbonylamino-3,3-dimethyl-butyric acid (30 g, 0.13 mol) in dichloromethane (400 mL) was added portionwise 1,1'-carbonyidiimidazole (63.3 g, 0.39 mol). After addition was complete the reaction was allowed to stir for 15 minutes before N-methoxy-N-methylamine hydrochloride (38 g, 0.39 mol) was added and the reaction allowed to stir for 16 hours. The solvents were removed in vacuo and the residue partitioned between ethyl acetate (250 mL) and 1M HCl (150 mL). The organic phase was washed with 1M HCl solution (2×100 mL), saturated sodium bicarbonate solution (2×100 mL) and brine (100 mL). The organic phase was dried over MgSO$_4$, filtered and the solvents removed in vacuo to give a crude yellow oil. Purification by column chromatography (SiO$_2$, 30% ethyl acetate in hexanes) afforded the title product as a pale yellow oil (26.5 g, 74%).

$^1$H NMR (CDCl$_3$): δ/ppm 5.20 (1H, bd, J=9.5 Hz), 4.65 (1H, d, J=10.4 Hz), 3.77 (3H, s), 3.21 (3H, s), 1.43 (9H, s), 0.97 (9H, s). LRMS: (m/z) 297 (M+Na)$^+$.

STEP C: (1(S)-(4-Fluorobenzoyl)]2,2-dimethylpropyl)carbamic Acid-tert-Butyl Ester

[1(S)-(Methoxy-methyl-carbamoyl)-2,2-dimethylpropyl]-carbamic acid-tert-butyl ester (548 mg, 2.0 mmol) was dissolved in freshly distilled THF (10 mL) under an argon atmosphere. The solution was cooled to 0° C. whereupon 4-fluorophenylmagnesium bromide (8.0 mL, 1.0 M in THF, 8.0 mmol, 4 eqv) was added dropwise maintaining an internal temperature <5° C. The reaction was stirred at 0° C. for 30 minutes before warming to room temperature for a further 20 hours. After this time the reaction was cooled to 0° C. and saturated aqueous ammonium chloride solution (30 mL) was added. The aqueous phase was extracted with ethyl acetate (3×30 mL) and the organic phases washed with water (3×50 mL) and brine (50 mL), dried over MgSO$_4$, filtered and the solvents removed in vacuo to give a crude yellow oil. Purification by column chromatography (SiO$_2$, 20% ethyl acetate in hexanes) afforded the title compound as a white solid (447 mg, 72%).

$^1$H NMR (CDCl$_3$): δ/ppm 8.03 (2H, m), 7.14 (2H, t, J=8.5 Hz), 5.41 (1H, bd, J=9.6 Hz), 5.12 (1H, d, J=9.6 Hz), 1.43 (9H, s), 0.92 (9H, s). LRMS: (m/z) 332 (M+Na)$^+$.

STEP D: 2(S)-Amino-1-(4-fluorophenyl)-3,3-dimethyl-butan-1-one

To a solution of (1(S)-(4-fluorobenzoyl)]-2,2-dimethylpropyl)carbamic acid-tert-butyl ester (319 mg, 1.03 mmol) in dichloromethane (5 mL) at 0° C. was added trifluoroacetic acid (2 mL).The reaction was placed at <5° C. for 16 hours before the solvents were removed in vacuo to give a bright yellow oil. The residue was dissolved in methanol (30 mL) and was treated portionwise with Dowex 1X8-400 basic resin until pH 9. Filtration and removal of the solvents in vacuo gave the title compound as a pale yellow oil (~1.0 g, >100%, residual water). Purification by column chromatography (SiO$_2$, 5% methanol in dichloromethane) gave the title compound as a colourless oil (190 mg, 88%).

$^1$H NMR (CDCl$_3$): δ/ppm 8.10 (2H, m), 7.15 (2H, t, J=8.4 Hz), 4.20 (1H, s), 1.70 (2H, bs), 0.93 (9H, s). LRMS: (m/z) 210 (M+H)$^+$.

STEP E: 2(R)-(N-Benzyloxyaminomethyl)-hexanoic Acid-(1'(S)-(4-fluorobenzoyl)-2',2'-dimethylpropyl)amide To a suspension of 2(R)-(N-benzyloxyamino-methyl)-hexanoic acid (237 mg, 0.91 mmol, 1.1 eqv) in DMF (5 mL) at 0° C. was added EDC (200 mg, 1.1 eqv) and 1-hydroxybenzotriazole (12 mg, 10 mol %). The mixture was allowed to stir at 0° C. for 45 minutes before a solution of 2(S)-amino-1-(4-fluorophenyl)-3,3-dimethyl-butan-1-one (179 mg, 0.83 mmol, 1 eqv) in DMF (2 mL) was added. The reaction was allowed to warm to room temperature and stirred for 16 hours. The solvents were removed in vacuo and the residue dissolved in ethyl acetate (30 mL) and 10% w/v aqueous citric acid (40 mL). The aqueous phase was extracted with ethyl acetate (3×20 mL) and the combined organic layers washed with saturated sodium hydrogen carbonate (70 mL) and brine (2×70 mL). The organic phases were dried over MgSO$_4$, filtered and the solvents removed in vacuo to give a crude yellow oil. Purification by column chromatography (SiO$_2$, 30% ethyl acetate in hexanes) gave the title compound as a clear oil (160 mg, 42%).

$^1$H NMR (CDCl$_3$): δ/ppm 8.07 (2H, m), 7.35 (5H, m), 7.13 (2H, t, J=8.7 Hz), 6.99 (1H, d, J=9.0 Hz), 5.52 (1H, d, J=9.0 Hz), 4.75 (2H, s), 3.10 (2H, m), 2.52 (1H, m), 1.70–1.10 (6H, m), 0.94 (9H, s), 0.81 (3H, t, J=6.6 Hz). LRMS: (m/z) 443 (M+H)$^+$.

STEP F: 2(R)-[N-Benzyloxy-N-formylamino)-methyl]-hexanoic Acid-(1'(S)-(4-fluorobenzoyl)-2',2'-dimethylpropyl)amide To a solution of 2(R)-(N-benzyloxyaminomethyl)-hexanoic acid-(1'(S)-(4-fluorobenzoyl)-2',2'-dimethylpropyl)amide (150 mg, 0.35 mmol) in dichloromethane (10 mL) at 0° C. was added formylacetic anhydride (80 μL, 0.88 mmol, 2.5 eqv) and the reaction allowed to stir at room temperature. After 2 hours the solvents were removed in vacuo and the residue azeotroped with toluene (3×30 mL). The product was placed under high vacuum to give the title compound as a pale yellow solid (145 mg, 88%).

$^1$H NMR (CDCl$_3$): δ/ppm 8.20–7.85 (3H, bm), 7.40 (5H, m), 7.15 (2H, m), 6.31 (1H, d, J=9.3 Hz), 5.42 (1H, d, J=9.2 Hz), 5.10–4.70 (2H, bm), 3.90–3.60 (2H, bm), 2.58 (1H, m), 1.80–1.05 (6H, m), 0.89 (9H, s), 0.78 (3H, t, J=6.8 Hz). LRMS: (m/z) 471 (M+H)$^+$.

STEP G: 2(R)-[N-Formyl-N-hydroxyamino)-methyl]-hexanoic Acid-(1'(S)-(4-fluorobenzoyl)2',2'-dimethylpropyl)amide To a solution 2(R)-[N-benzyloxy-N-formylamino)-methyl]-hexanoic acid-(1'(S)(4-fluorobenzoyl)-2',2'-dimethylpropyl)amide (145 mg, 0.31 mmol) in methanol (10 mL) under an argon atmosphere was added a slurry of 10% Pd/C (15 mg) in ethyl acetate (1 mL). Hydrogen gas was bubbled through the reaction for 15 minutes after which time the reaction was allowed to stir under 1 atmosphere of hydrogen for two hours. The reaction was flushed with argon and filtered through glass wool. The solvents were removed in vacuo to afford the title compound as a hygroscopic white crystalline solid (105 mg, 90%).

$^1$H NMR (CDCl$_3$): δ/ppm 8.40 (0.3H, s), 8.05 (2H, dd, J=6.8, 5.4 Hz), 7.86 (0.7H, s), 7.16 (2H, t, J=3.2 Hz), 6.90 (0.3H, bd, J=9.1 Hz), 6.82 (0.7H, bd, J=9.2 Hz), 5.50 (1H, d, J=9.3 Hz), 4.02 (0.2H, dd, J=14.5, 7.5 Hz), 3.87 (0.8H, dd, J=14.2, 10.0 Hz), 3.62 (0.2H, dd, J=11.0, 3.0 Hz), 3.46 (0.8H, dd, J=14.1, 4.6 Hz), 2.88–2.70 (1H, m), 1.55 (1H, m), 1.45–1.10 (5H, m), 0.94 (2H, s), 0.90 (7H, s), 0.78 (3H, t, J=6.6 Hz). $^{13}$C NMR (CDCl$_3$): δ/ppm 199.6, 199.3, 173.5, 168.5, 164.5, 134.5, 131.8, 131.7, 116.7, 116.6, 116.3, 116.2, 59.5, 52.6, 48.4, 48.1, 45.0, 35.7, 30.5, 29.8, 29.5, 28.7, 28.5, 27.4, 22.9, 14.2. LRMS: (m/z) 381 (M+H)$^+$, 403 (M+Na)$^+$. MIC (*E. Coli*): 12.5 μM MIC (*S. Capitis*): 25 μM

EXAMPLE 2

2(R)-[(N-Formyl-N-hydroxyamino)-methyl]-hexanoic Acid-(1'(S)-(4-methoxybenzoyl 2', 2'dimethylpropyl)amide

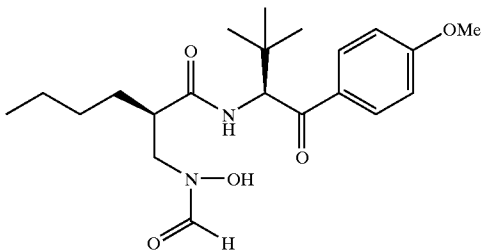

The title compound was prepared as described in Scheme 1 in an analogous manner to 2(R)-[N-formyl-N-hydroxyamino)-methyl]-hexanoic acid-(1'(S)-(4-fluorobenzoyl)-2',2'-dimethylpropyl)amide. The relevant spectroscopic data are described below.

STEP C: (1(S)-(4-Methoxybenzoyl)]-2,2-dimethylpropyl)carbamic Acid-tert-butyl Ester Purification by column chromatography (SiO$_2$, 20% ethyl acetate in hexanes) afforded the title compound as a white solid (836 mg, 71%).

$^1$H NMR (CDCl$_3$): δ/ppm 8.00 (2H, d, J=8.8 Hz), 6.95 (2H, d, J=8.8 Hz), 5.45 (1H, d, J=9.5 Hz), 5.12 (1H, d, J=9.8 Hz), 3.89 (3H, s), 1.43 (9H, s), 0.93 (9H, s).

STEP D: 2(S)-Amino-1-(4-methoxyphenyl)-3,3-dimethyl-butan-1-one

Purification by column chromatography (SiO$_2$, 5% methanol in dichloromethane) gave the title compound as a colourless oil (176 mg, 78%).

$^1$H NMR (CDCl$_3$): δ/ppm 7.95 (2H, d, J=9.0 Hz), 6.93 (2H, d, J=9.0 Hz), 4.20 (1H, s), 3.89 (3H, s), 1.68 (2H, bs), 0.94 (9H, s). LRMS: (m/z) 222 (M+H)$^+$.

STEP E: 2(R)-(N-Benzyloxyaminomethyl)-hexanoic Acid-(1'(S)(4-methoxybenzoyl)-2',2'-dimethylpropyl)amide Purification by column chromatography (SiO$_2$, 30% ethyl acetate in hexanes) gave the title compound as a clear oil (215 mg, 61%).

$^1$H NMR (CDCl$_3$): δ/ppm 8.01 (2H, d, J=9.0 Hz), 7.35 (5H, m), 6.95 (2H, d, J=9.0 Hz), 5.55 (1H, d, J=9.5 Hz), 4.73 (2H, m), 3.87 (3H, s), 3.10 (2H, m), 2.51 (1H, m), 1.70–1.10 (6H, m), 0.94 (9H, s), 0.80 (3H, t, J=6.7 Hz). LRMS: (m/z) 455 (M+H)$^+$.

STEP F: 2(R)-[N-Benzyloxy-N-formylamino)-methyl]-hexanoic Acid-(1'(S)-(4-methoxybenzoyl)-2',2'-dimethylpropyl)amide The title compound was isolated as a pale yellow solid (187 mg, 88%).

$^1$H NMR (CDCl$_3$): δ/ppm 8.20–7.85 (3H, m), 7.60–7.30 (5H, m), 7.05–6.90 (2H, bd, J=8.7 Hz), 6.40 (1H, bd, J=9.2 Hz), 5.50 (1H, bd, J=9.3 Hz), 5.10–4.70 (2H, bm), 3.92 (3H, bs), 3.75 (2H, bm), 2.60 (1H, m), 1.90–1.10 (6H, m), 0.89 (9H, s), 0.77 (3H, m). LRMS: (m/z) 483 (M+H)$^+$.

STEP G: 2(R)-[N-Formyl-N-hydroxyamino)-methyl]-hexanoic Acid-(1'(S)-(4-methoxybenzoyl)-2',2'-dimethylpropyl)amide The title compound was isolated as a hygroscopic white crystalline solid (133 mg, 98%).

$^1$H NMR (CDCl$_3$): δ/ppm 8.40 (0.3H, s), 8.00 (2H, d, J=8.8 Hz), 7.86 (0.7H, s), 6.95 (2H, d, J=8.8 Hz), 6.76 (1H, d, J=9.3 Hz), 5.52 (1H, d, J=9.4 Hz), 4.10 (1H, m), 3.88 (3H, s), 3.62 (0.3H, dd, J=14.6, 3.1 Hz), 3.47 (0.7H, dd, J=14.0, 4.0 Hz), 2.85 (0.7H, m), 2.72 (0.3H, m), 1.55 (1H, m), 1.45–1.10 (5H, m), 0.94 (3H, s), 0.90 (6H, s), 0.77 (3H, t, J=6.6 Hz). $^{13}$C NMR (CDCl$_3$): δ/ppm 199.2, 198.9, 176.3, 173.3, 164.7, 164.5, 131.6, 131.5, 130.7, 114.7, 114.4, 59.3, 59.0, 55.9, 52.5, 48.3, 46.5, 45.1, 36.1, 35.9, 30.4, 30.3, 29.6, 27.5, 22.9, 14.2. LRMS: (m/z) 391 (M-H)$^-$; 393 (M+H)$^+$, 415 (M+Na)$^+$. MIC (*E. Coli*): 12.5 μM MIC (*S. Capitis*): 6.25 μM

EXAMPLE 3

2(R)-[(N-Formyl-N-hydroxyamino)-methyl]-hexanoic Acid-(1'(S)-cyclohexanecarbonyl-2'-methylpropyl)amide

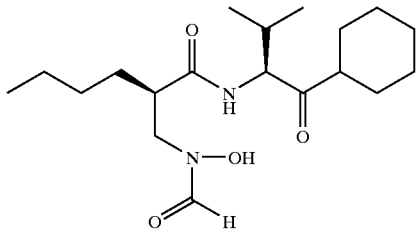

The title compound was prepared in an analogous manner to that described in Scheme 1 utilising 2(S)-tert-butoxycarbonylamino-3-methyl-butyric acid as the starting material in Step B. The relevant spectroscopic data are described below.

STEP B: [1(S)-(Methoxy-methyl-carbamoyl)-2-methylpropyl]-carbamic Acid-tert-butyl Ester The title product was isolated as a pale yellow oil (14.7 g, 82%).

$^1$H NMR (CDCl$_3$): δ/ppm 5.13 (1H, m), 4.57 (1H, m), 3.77 (3H, s), 3.21 (3H, s), 1.99 (1H, m), 1.44 (9H, s), 0.96 (3H, d, J=6.8 Hz), 0.90 (3H, d, J=6.8 Hz).

STEP C: (1(S)-(Cyclohexanecarbonyl)-2-methylpropyl)carbamic Acid-tert-butyl Ester Purification by column chromatography (SiO$_2$, 25% ethyl acetate in hexanes) afforded the title compound as a white solid (253 mg, 42%).

$^1$H NMR (CDCl$_3$): δ/ppm 5.13 (1H, bd, J=8.5 Hz), 4.40 (1H, m), 2.52 (1H, m), 2.13 (1H, m), 2.00–1.60 (7H, m), 1.44 (9H, s), 1.25 (3H, m), 1.01 (3H, d, J=6.9 Hz), 0.75 (3H, d, J=6.9 Hz).

STEP D: 2(S)-Amino-1-cyclohexyl-3-methyl-butan-1-one

The title compound was isolated as colourless oil (158 mg, 98%).

$^1$H NMR (CDCl$_3$): δ/ppm 3.49 (1H, d, J=3.7 Hz), 2.55 (1H, m), 2.12 (1H, m), 1.95–1.10 (10H, m), 1.03 (3H, d, J=6.9 Hz), 0.75 (3H, d, J=6.8 Hz).

STEP E: 2(R)-(N-Benzyloxyaminomethyl)-hexanoic Acid-(1'(S)-cyclohexanecarbonyl-2'-methylpropyl)amide Purification by column chromatography (SiO$_2$, 25% ethyl acetate in hexanes) gave the title compound as a clear oil (116 mg, 35%).

¹H NMR (CDCl₃): δ/ppm 7.35 (5H, m), 6.49 (1H, d, J=8.9 Hz), 5.70 (1H, bs), 4.78 (1H, dd, J=8.9, 4.7 Hz), 4.72 (2H, s), 3.08 (2H, m), 2.52 (2H, m), 2.15 (1H, m), 2.05 –1.10 (16H, m), 0.98 (3H, d, J=6.8 Hz), 0.86 (3H, t, J=6.9 Hz), 0.78 (3H, d, J=6.8 Hz). LRMS: (m/z) 417 (M+H)⁺.

STEP F: 2(R)-[N-Benzyloxy-N-formylamino)-methyl]-hexanoic Acid-(1'(S)-cyclohexanecarbonyl-2'-methylpropyl)amide The title compound was isolated as a viscous oil (105 mg, 99%).

¹H NMR (CDCl₃): δ/ppm 8.30 –7.80 (1H, m), 7.40 (5H, m), 6.12 (1H, m), 5.15–4.60 (3H, m), 3.95–3.50 (2H, m), 3.10 (1H, m), 2.55 (2H, m), 1.10–2.30 (16H, m), 1.10–0.60 (9H, m). LRMS: (m/z) 445 (M+H)⁺, 467 (M+Na)⁺.

STEP G: 2(R)-[N-Formyl-N-hydroxyamino)-methyl]-hexanoic Acid-(1'(S)-cyclohexanecarbonyl-2'-methylpropyl)amide The title compound was isolated as a hygroscopic white crystalline solid (67 mg, 84%).

¹H NMR (CDCl₃): δ/ppm 8.37 (0.3H, s), 7.81 (0.7H, s), 6.69 (1H, d, J=9.0 Hz), 4.74 (1H, dd, J=9.0, 5.0 Hz), 4.00 (0.3H, dd, J=14.6, 7.6 Hz), 3.84 (0.7H, dd, J=14.0, 9.8 Hz), 3.59 (0.3H, dd, J=14.5, 3.4 Hz), 3.43 (0.7H, dd, J=14.1, 3.7 Hz), 2.83 (0.7H, m), 2.70 (0.3H, m), 2.50 (1H, m), 2.12 (1H, m), 2.00–1.10 (16H, m), 1.00–0.60 (9H, m). ¹³C NMR (CD₃OD): δ/ppm 176.3, 173.5, 61.5, 61.3, 52.9, 49.5, 49.3, 48.5, 30.7, 30.4, 30.2, 30.0, 29.8, 29.6, 27.6, 26.3, 26.1, 25.6, 25.5, 23.0, 20.3, 17.6, 14.3. LRMS: (m/z) 355 (M+H)⁺, 377 (M+Na)⁺. MIC (*E. Coli*): 50 μM MIC (*S. Capitis*): 25 μM

EXAMPLE 4

3-Cyclopentyl-2(R)-[(N-formyl-N-hydroxyamino)-methyl]-N-[1'(S)-(4-fluorobenzoyl)-2',2'-dimethylpropyl]propionamide

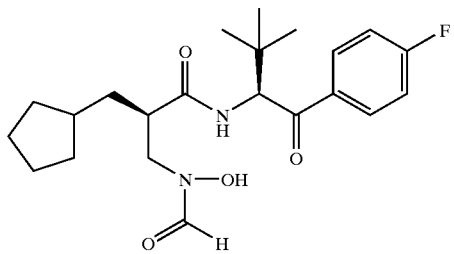

The title compound was prepared in an analogous manner to that described in Scheme 1 utilising 2(R)-(benzyloxyamino-methyl)-3-cyclopentyl-propionic acid in Step E. Spectroscopic data are described below. Experimental details of the synthesis of 2(R)-(benzyloxyamino-methyl)-3-cyclopentyl-propionic acid and relevant spectroscopic data are also presented.

STEP G: 3-Cyclopentyl-2(R)-[(N-formyl-N-hydroxyamino)-methyl]-N-[1'(S)-(4-fluorobenzoyl)-2',2'-dimethylpropyl]propionamide The title compound was isolated as a hygroscopic white crystalline solid (120 mg, 81%).

¹H NMR (CD₃OD): δ/ppm 8.27 (0.3H, s), 8.10 (2H, m), 7.85 (0.7H, s), 7.23 (2H, t, J=8.7 Hz), 5.47 (1H, m), 3.77 (1H, m), 3.58 (0.3H, dd, J=14.0, 5.6 Hz), 3.42 (0.7H, dd, J=14.1, 4.7 Hz), 3.09 (0.7H, m), 2.93 (0.3H, m), 1.82–1.20 (9H, m), 1.15–0.80 (11H, m). ¹³C NMR (CD₃OD): δ/ppm 176.8, 176.5, 169.8, 165.7, 136.3, 132.9, 132.8, 117.4, 117.0, 61.1, 54.3, 45.1, 45.0, 39.3, 38.1, 38.0, 36.2, 34.4, 33.7, 33.6, 27.8, 26.4, 26.3. LRMS: (m/z) 407 (M+H)⁺. MIC (*E. Coli*): 3.1 μM MIC (*S. Capitis*): 3.1 μM

EXAMPLE 5

3-Cyclopentyl-2(R)-[(N-formyl-N-hydroxyamino)-methyl]-N-[1'(S)-(4-methoxybenzoyl)-2',2'-dimethylpropyl]propionamide

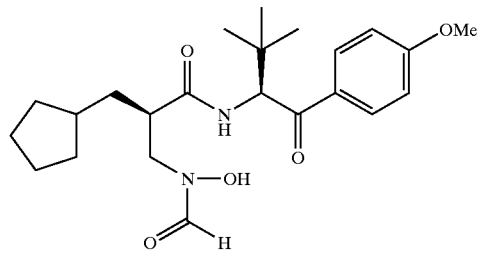

The title compound was prepared in an analogous manner to that described in Scheme 1 utilising 2(R)-(benzyloxyamino-methyl)-3-cyclopentyl-propionic acid in Step E. Spectroscopic data are described below.

STEP G: 3-Cyclopentyl-2(R)-[(N-formyl-N-hydroxyamino)-methyl]-N-[1'(S)(4-methoxybenzoyl)-2',2'-dimethylpropyl]propionamide The title compound was isolated as a hygroscopic white crystalline solid (173 mg, 96%).

¹H NMR (CD₃OD): δ/ppm 8.26 (0.4H, s), 8.01 (2H, d, J=9.0 Hz), 7.85 (0.6H, s), 7.01 (2H, d, J=9.0 Hz), 5.49 (1H, bs), 3.87 (3H, s), 3.79 (1H, m), 3.59 (0.4H, dd, J=11.7, 5.6 Hz), 3.41 (0.6H, dd, J=14.4, 4.9 Hz), 3.09 (0.6H, m), 2.92 (0.4H, m), 1.85–1.20 (9H, m), 1.15–0.80 (11H, m). ¹³C NMR (CD₃OD): δ/ppm 200.0, 176.6, 176.4, 166.0, 132.5, 132.3, 115.4, 60.6, 60.5, 56.5, 54.3, 51.9, 45.3, 45.1, 39.3, 38.1, 36.3, 34.3, 33.8, 33.6, 27.9, 26.4, 26.3. LRMS: (m/z) 419 (M+H)⁺. MIC (*E. coli*): 3.1 μM MIC (*S. capitis*): 1.6 μM Synthesis of 2(R)-(benzyloxyamino-methyl)-3-cyclopentyl-propionic Acid

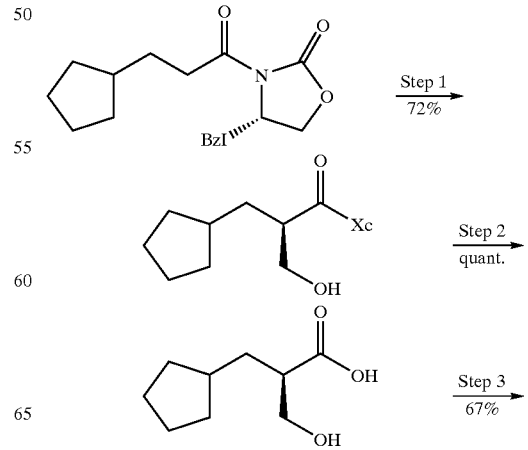

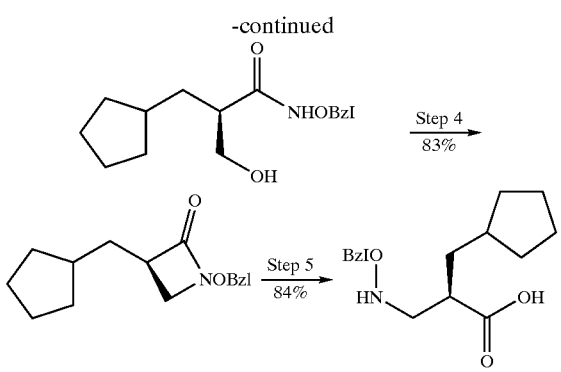

Reagents and Conditions: 1: TiCl₄, trioxane, CH₂Cl₂; 2: H₂O₂, LiOH; 3: H₂NOBn, WSC, THF/H₂O; 4: Ph₃P, DIAD, THF; 5: LiOH, THF/MeOH/H₂O.

Step 1: 4S-Benzyl-3-[3-cyclopentyl-2R-hydroxymethyl-propionyl]-oxazolidin-2-one To a stirred, cooled (0° C.) solution of 4S-benzyl-(3-cyclopentyl-propionyl)-oxazolidin-2-one (21 g, 69.8 mmol) in dichloromethane (350 ml) was added a solution of titanium tetrachloride (1M in dichloromethane, 73.25 ml, 73.2 mmol), dropwise. The resulting yellowish slurry was stirred for 10 minutes at 0° C., and then DIPEA (13.37 ml, 76.7 ml) was added dropwise to furnish a dark-red solution. The stirring was maintained for 1 h at 0° C., and then a solution of s-trioxane (7.53 g, 83.7 mmol), in dichloromethane (70 ml) was added dropwise followed by the addition of a solution of titanium tetrachloride (1M in dichloromethane, 73.25 ml, 73.2 mmol). The reaction mixture was then stirred for 4 h at 0° C. Saturated aqueous ammonium chloride (250 ml) was added to the reaction mixture and the aqueous layer was extracted with additional dichloromethane (2×300 ml). The combined organic layers were washed with water (150 ml) and with brine (80 ml), dried over anhydrous magnesium sulfate, filtered and concentrated in vacuo to yield a yellow solid which on trituration with diethyl ether furnished a white solid (16.57 g, 72%).

¹H NMR (CDCl₃): δ/ppm 7.38–7.22 (5H, m), 4.70 (1H, m), 4.22–4.18 (2H, m), 3.99 (1H, m), 3.96–3.75 (2H, m), 3.31 (1H, dd, J=13.4 & 3.3 Hz), 2.82 (1H, dd, J=13.4 & 9.4 Hz), 2.24 (1H, dd, J=8.3 & 4.5 Hz), 2.81–1.30 (4H, m) and 1.13 (1H, m); ¹³C NMR (CDCl₃): δ/ppm 176.3, 153.6, 135.2, 129.5, 129.0, 127.4, 66.2, 64.2, 55.7, 44.8, 37.9, 37.8, 34.6, 33.0, 32.4 and 25.1.

Step 2: 3-Cyclopentyl-2R-hydroxymethyl-propionic Acid

To a stirred, cooled (0° C.) solution of 4S-Benzyl-3-[3-cyclopentyl-2R-hydroxymethyl-propionyl]-oxazolidin-2-one (16.05 g, 48.5 mmol) in THF-water (4:1, 250 ml) was added 27.5% aqueous hydrogen peroxide (24 ml, 194 mmol), followed by lithium hydroxide monohydrate (4.07 g, 97 mmol) in water (50 ml). After the reaction was complete (30 min), THF was removed in vacuo. The aqueous layer was extracted with dichloromethane (3×100 ml) and acidified to pH 2 with 4M hydrochloric acid. The aqueous layer was extracted with diethyl ether (2×150 ml). The combined organic layers were washed with brine (60 ml), dried over anhydrous magnesium sulfate and filtered. The solvent was removed in vacuo to afford a yellow oil which was further purified by column chromatography (25% ethyl acetate in hexanes to 100% ethyl acetate) to furnish the title compound as an oil (8.3 g, quant.).

¹H NMR (CDCl₃): δ/ppm 6.60–5.90 (1H, br s), 3.80–3.78 (2H, m), 2.67 (1H, m), 1.98–1.40 (9H, m) and 1.20–0.98 (2H, m). ¹³C NMR (CDCl₃): δ/ppm 181.0, 63.2, 46.9, 37.8, 34.5, 32.7, 32.6, 25.1 and 25.1.

Step 3: N-Benzyloxy-3-cyclopentyl-2R-hydroxymethyl-propionamide

To a stirred, cooled (0° C.) mixture of 3-cyclopentyl-2R-hydroxymethyl-propionic acid (1.1 g, 6.4 mmol) in THF-water (4:1, 30 ml), was added O-benzylhydroxylamine. The pH of the resulting solution was adjusted to 4.5 by addition of 1M hydrochloric acid, and then EDC (1.84 g, 9.6 mmol) was added in one portion. The resulting solution was stirred for 2.5 h at room temperature while controlling pH at 4.5 by addition of 1M hydrochloric acid. After removal of the THF, the aqueous layer was extracted with ethyl acetate (3×40 ml) and the combined organic layers were washed with 10% citric acid (3×15 ml), 5% sodium hydrogen carbonate and dried over anhydrous magnesium sulfate. The solvent was removed in vacuo to afford the title compound as a colourless crystalline solid (1.18 g, 67%). This compound was then used without any further purification.

¹H NMR (CDCl₃): δ/ppm 8.14 (1H, br s), 7.40–7.34 (5H, m), 4.94 (2H, brs), 3.76–3.66 (2H, m), 1.79–1.47 (11H, m) and 1.17–0.97 (2H, m). LRMS: +ve ion 278 [M+H], 555 [2M+H].

Step 4: N-Benzyloxy-3R-cyclopentylmethyl-azetidin-2-one

To a stirred, cooled (0° C.) solution of N-Benzyloxy-3-cyclopentyl-2R-hydroxymethyl-propionamide (8.63 g, 31.1 mmol) and triphenylphosphine (9 g, 34.2 mmol) in dry THF (320 ml) was added DIAD (6.12 ml, 31.1 mmol), dropwise. The resulting solution was stirred at room temperature overnight. After removal of THF in vacuo, the residue was purified by column chromatography (hexanes:ethyl acetate, 5:1 to 3:1) to give the desired product as a white solid (6.7 g, 83%).

¹H NMR (CDCl₃): δ/ppm 7.76–7.39 (5H, m), 4.94 (2H, br s), 3.36 (1 H, m), 2.96–2.80 (2H, m), 1.89–1.38 (9H, m) and 1.18–0.98 (2H, m). ¹³C NMR (CDCl₃): δ/ppm 167.7, 129.6, 129.3, 129.0, 78.1, 52.5, 45.1, 39.1, 35.2, 33.1, 32.9, 25.5 and 25.3. LRMS: +ve ion 260 [M+H], 519 [2M+H].

Step 5: 2R-(Benzyloxyamino-methyl)-3-cyclopentyl-propionic Acid

To a stirred, cooled (0° C.) solution of N-Benzyloxy-3R-cyclopentylmethyl-azetidin-2-one (6.7 g, 25.8 mmol) in THF-methanol (3:1, 100 ml) was added lithium hydroxide monohydrate (1.3 g, 31.0 mmol) in water (25 ml). The reaction mixture was stirred and allowed to warm to room temperature overnight. The solvent was removed in vacuo and the aqueous layer was extracted with diethyl ether, then acidified to pH 2 by addition of 4M hydrochloric acid. The aqueous layer was extracted with diethyl ether (3×40 ml), and the combined organic layers were washed with brine, dried over anhydrous magnesium sulfate, filtered and concentrated in vacuo to give the title compound as white crystals (6.02 g, 84%).

¹H NMR (CDCl₃): δ/ppm 7.68–7.30 (5H, m), 4.78–4.68 (2H, m), 3.12–3.10 (2H, d, J=6.9 Hz), 2.76 (1H, m), 1.91–1.39 (11H, m), 1.20–1.00 (2H, m). ¹³C NMR (CDCl₃): δ/ppm 180.1, 137.7, 129.0, 128.9, 128.5, 78.0, 53.9, 42.9, 38.3, 36.6, 33.1, 33.0, 25.5. LRMS: 276 [M–H], 553 [2M–H].

EXAMPLE 6

2(R)-[(N-Formyl-N-hydroxyamino)-methyl]-hexanoic Acid-[2,2-dimethyl-1(S)(1-methyl-1H-imidazole-2-carbonyl)-propyl]-amide

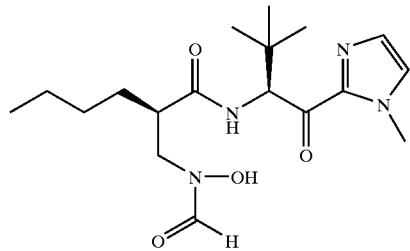

The title compound was prepared as described in Scheme 2. The experimental details of the synthesis and relevant spectroscopic data are described below.

STEP A: 2(S)-Amino-N-methoxy-3,3,N-trimethyl-butyramide

To a solution of [1(S)-(methoxy-methyl-carbamoyl)-2,2-dimethylpropyl]-carbamic acid-tert-butyl ester (1.686 g, 6.15 mmol) in dichloromethane (20 mL) at 0° C. was added trifluoroacetic acid (17 mL). The reaction was allowed to stand for 16 hours at <5° C. before the solvents were removed in vacuo to give a bright yellow oil. The residue was dissolved in methanol (30 mL) and was treated portionwise with Dowex 1X8-400 basic resin until pH 9. Filtration and removal of the solvents in vacuo gave the title compound as a pale yellow oil (990 mg, 92%). The material was used without further purification.

$^1$H NMR (CDCl$_3$): δ/ppm 3.70 (3H, s), 3.61 (1H, bs), 3.20 (3H, s), 1.60 (2H, bs), 0.98 (9H, s). LRMS: (m/z) 175 (M+H)$^+$.

STEP B: 2(R)-[(N-Benzyloxyamino)-methyl]-hexanoic Acid-[1'(S)-(methoxy-methyl-carbamoyl)-2',2'-dimethylpropyl]amide To a suspension of 2(R)-(N-benzyloxyamino-methyl)-hexanoic acid (1.430 g, 5.17 mmol, 1.1 eqv) in DMF (20 mL) at 0° C. was added EDC (1.190 g, 5.64 mmol, 1.2 eqv) and 1-hydroxybenzotriazole (84 mg, 10 mol %). The mixture was allowed to stir at 0° C. for 45 minutes before a solution of 2(S)-amino-N-methoxy-3,3,N-trimethyl-butyramide (900 mg, 4.7 mmol, 1 eqv) in DMF (5 mL) was added. The reaction was allowed to warm to room temperature and stirred overnight. The solvents were removed in vacuo and the residue dissolved in ethyl acetate (75 mL) and 10% w/v aqueous citric acid (50 mL). The aqueous phase was extracted with ethyl acetate (3×75 mL) and the combined organic layers washed with saturated sodium hydrogen carbonate solution (100 mL) and brine (2×100 mL). The organic phases were dried over MgSO$_4$, filtered and the solvents removed in vacuo to give a crude yellow oil. Purification by column chromatography (SiO$_2$, 25% ethyl acetate in hexanes) gave the title compound as a clear oil (1.43 g, 68%).

$^1$H NMR (CDCl$_3$): δ/ppm 7.35 (5H, m), 6.73 (1H, bd, J=10.0 Hz), 5.70 (1H, bs), 5.05 (1H, d, J=10.0 Hz), 4.74 (2H, s), 3.78 (3H, s), 3.20 (3H, s), 3.07 (2H, m), 2.50 (1H, m), 1.65 (1H, m), 1.45 (1H, m), 1.25 (4H, m), 0.98 (9H, s), 0.86 (3H, t, J=7.0 Hz). LRMS: (m/z) 408 (M+H)$^+$.

STEP C: 2(R)-[(N-Benzyloxyamino)-methyl]-hexanoic Acid-[2,2-dimethyl-1(S)-(1-methyl-1H-imidazole-2-carbonyl propyl]-amide To a solution of N-methyl-imidazole (246 mg, 3 mmol, 6 eqv), in dry freshly distilled THF (5 mL) under argon at −78° C. was added dropwise n-BuLi (1.84 mL, 1.6M in hexanes, 3.0 mmol, 6 eqv) such that an internal temperature of <−70° C. was maintained. The reaction was allowed to stir at −70° C. for 90 minutes after which time a solution of 2(R)-[(N-benzyloxyamino)-methyl]-hexanoic acid-[1'(S)-(methoxy-methyl-carbamoyl)-2',2'-dimethylpropyl]amide (204 mg, 0.5 mmol, 1eqv) in freshly distilled THF (2 mL) was added dropwise such that an internal temperature of <−70° C. was maintained. The reaction was allowed to stir at −70° C. for five hours before saturated aqueous ammonium chloride solution (10 mL) was added and the solution allowed to warm to room temperature. The aqueous phase was extracted with ethyl acetate (3×50 mL), and the organic phases combined and washed with water (3×50 mL) and brine (50 mL). The organic phase was dried over MgSO$_4$, filtered and the solvents removed in vacuo to give a crude yellow oil. Purification by column chromatography (SiO$_2$, 30% hexanes in ethyl acetate) gave the title product as a colourless oil (77 mg, 36%).

$^1$H NMR (CDCl$_3$): δ/ppm 7.33 (5H, m), 7.17 (1H, s), 7.03 (1H, s), 5.75 (1H, bs), 5.65 (1H, d, J=9.1 Hz), 4.75 (2H, s), 3.98 (3H, s), 3.10 (2H, m), 2.54 (1H, m), 1.90 (1H, bm), 1.58 (1H, m), 1.40 (1H, m), 1.23 (4H, m), 0.99 (9H, s), 0.80 (3H, t, J=6.7 Hz). LRMS: (m/z) 429 (M+H)$^+$.

STEP D: 2(R)-[(N-Benzyloxy-N-formylamino)-methyl]-hexanoic Acid-[2,2-dimethyl-1(S)-(1-methyl-1H-imidazole-2-carbonyl)-propyl]-amide To a solution of 2(R)-[(N-benzyloxyamino)-methyl]-hexanoic acid-[2,2-dimethyl-1(S)-(1-methyl-1H-imidazole-2-carbonyl)-propyl]-amide (77 mg, 0.18 mmol) in dichloromethane (2 mL) at 0° C. was added formylacetic anhydride (50 μL, 0.54 mmol, 3 eqv) and the reaction allowed to stir at room temperature. After 2 hours the solvents were removed in vacuo and the residue azeotroped with toluene (2×30 mL). The product was placed under high vacuum for several hours to give the title compound as an off white waxy solid (76 mg, 93%).

$^1$H NMR (CDCl$_3$): δ/ppm 8.30–7.80 (1H, m), 7.40 (5H, bm), 7.19 (1H, bs), 7.05 (1H, bs), 5.55 (1H, bd, J=9.3 Hz), 5.15–4.70 (2H, bm), 3.96 (3H, bs), 3.80 (1H, bm), 3.15 (1H, bm), 2.60 (1H, m), 1.70–0.70 (18H, m). LRMS: (m/z) 456 (M+H)$^+$.

STEP E: 2(R)-[(N-Formyl-N-hydroxyamino) methyl]-hexanoic Acid-[2,2-dimethyl-1(S)-(1-methyl-1H-imidazole-2-carbonyl)-propyl]-amide To a solution of 2(R)-[(N-benzyloxy-N-formylamino)-methyl]-hexanoic acid-[2,2-dimethyl-1(S)-(1-methyl-1H-imidazole-2-carbonyl)-propyl]-amide. (76 mg, 0.17 mmol) in methanol (2 mL) was added a slurry of 10% Pd/C (10 mg) in ethyl acetate (1 mL). Hydrogen gas was bubbled through the reaction for 15 minutes after which time the reaction was allowed to stir under one atmosphere of hydrogen for 2 hours. The reaction was flushed with argon and filtered through glass wool. The solvents were removed in vacuo to afford the title compound as a hygroscopic white crystalline solid (43 mg, 70%).

$^1$H NMR (CD$_3$OD): δ/ppm 8.26 (0.3H, s), 8.22 (0.7H, d, J=9.0 Hz), 8.10 (0.3H, d, J=8.0 Hz), 7.84 (0.7H, s), 7.35 (1H, s), 7.14 (1H, s), 5.71 (1H, m), 3.99 (3H, s), 3.72 (1H, m), 3.40 (0.5H, dd, J=14.1, 4.6 Hz), 3.31 (0.5H, m), 3.05 (0.7H, m), 2.88 (0.3H, m), 1.60–1.10 (6H, m), 0.99 (4H, s), 0.97 (5H, s), 0.82 (3H, t, J=6.6 Hz). $^{13}$C NMR (CDCl$_3$): δ/ppm 194.7, 178.7, 147.2, 132.9, 132.4, 65.2, 56.5, 48.2, 47.9, 39.6, 39.1, 34.1, 33.2, 30.4, 26.6 and 17.2. LRMS: (m/z) 365

(M–H)⁻, 367 (M+H)⁺. MIC (*E. coli*): 25 μM MIC (*S. capitis*): 200 μM

EXAMPLE 7

2(R)-[(N-Formyl-N-hydroxyamino)-methyl]-hexanoic Acid-[2,2-dimethyl-1(S)-(pyridine-2-carbonyl)-propyl]-amide

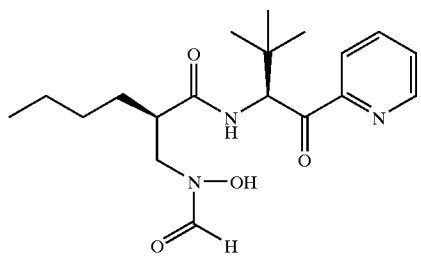

The title compound was prepared from 2-bromopyridine as outlined in Scheme 2, in an analogous manner to 2(R)-[(N-formyl-N-hydroxyamino)-methyl]-hexanoic acid-[2,2-dimethyl-1(S)-(1-methyl-1H-imidazole-2-carbonyl)-propyl]-amide. The relevant spectroscopic data are described below.

STEP C: 2(R)-[(N-Benzyloxyamino)-methyl]-hexanoic Acid-[2,2-dimethyl-1(S)-(pyridine-2-carbonyl)-propyl]-amide Purification by column chromatography (SiO₂, 30% to 50% ethyl acetate in hexanes) gave the title product as a colourless oil (160 mg, 60%).

¹H NMR (CDCl₃): δ/ppm 8.72 (1H, m), 8.05 (1 H, m), 7.82 (1H, m), 7.45 (1H, m), 7.40–7.28 (5H, m), 7.00 (1H, bd, J=9.3 Hz), 6.22 (1H, d, J=9.3 Hz), 5.74 (1H, bs), 4.76 (2H, s), 3.11 (2H, m), 2.52 (1H, m), 1.58 (1H, m), 1.40 (1H, m), 1.22 (4H, m), 0.95 (9H, s), 0.81 (3H, t, J=6.6 Hz). LRMS: (m/z) 426 (M+H)⁺.

STEP D: 2(R)-[(N-Benzyloxy-N-formylamino)-methyl]-hexanoic Acid-[2,2-dimethyl-1(S)-(pyridine-2-carbonyl)propyl]-amide The title compound was isolated as a pale yellow waxy solid (162 mg, 90%).

¹H NMR (CDCl₃): δ/ppm 8.75 (1H, m), 8.35–7.80 (4H, m), 7.60–7.10 (5H, m), 6.10 (1H, m), 4.90 (2H, m), 3.75 (2H, bm), 2.90 (2H, bm), 1.60–1.10 (6H, bm), 0.90 (9H, s), 0.85 (3H, m). LRMS: (m/z) 454 (M+H)⁺.

STEP E: 2(R)-[(N-Formyl-N-hydroxyamino)-methyl]-hexanoic Acid-[2,2-dimethyl-1(S)-(pyridine-2-carbonyl)-propyl]-amide The title compound was isolated as a hygroscopic white crystalline solid (113 mg, 94%).

¹H NMR (CD₃OD): δ/ppm 8.72 (1H, m), 8.27 (0.3H, s), 8.10–7.90 (2H, m), 7.85 (0.7H, s), 7.59 (1H, m), 7.40–7.20 (1 H), 6.18 (1H, m), 3.85–3.58 (1.7H, m), 3.41 (0.3H, dd, J=14.2, 4.7 Hz), 3.05 (0.7H, m), 2.89 (0.3H, m), 1.60–1.05 (6H, m), 0.97 (3.5H, s), 0.95 (5.5H, s), 0.79 (3H, t, J=6.7 Hz). ¹³C NMR (CD₃OD): δ/ppm 176.5, 176.2, 155.3, 150.6, 139.1, 129.2, 123.9, 122.3, 60.1, 53.5, 45.6, 45.3, 35.8, 32.2, 30.7, 27.9, 24.1, 14.8. LRMS: (m/z) 364 (M+H)⁺. MIC (*E. Coli*): 12.5 μM MIC (*S. Capitis*): 50 μM

EXAMPLE 8

2(R)-[(N-Formyl-N-hydroxyamino)-methyl]-hexanoic Acid-(1'(S)-(benzofuran-2-carbonyl)-2',2'-dimethylpropyl)amide

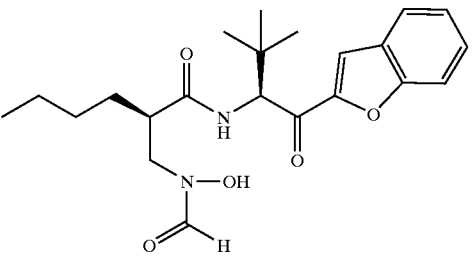

The title compound was prepared from 2-lithiobenzofuran as outlined in Scheme 2, in an analogous manner to 2(R)-[(N-Formyl-N-hydroxyamino)-methyl]-hexanoic acid-[2', 2'-dimethyl-1'(S)-(1-methyl-1H-imidazole-2-carbonyl)-propyl]-amide. The relevant spectroscopic data are described below.

STEP C: 2(R)-[(N-Benzyloxyamino)-methyl]-hexanoic Acid-[1'(S)-(bezofuran-2-carbonyl)-2',2'-dimethyl-propyl]-amide Purification by column chromatography (SiO₂, 25% ethyl acetate in hexanes) gave the title compound as a colourless oil (43 mg, 19%).

¹H NMR (CDCl₃): 7.90–7.20 (10H, m), 7.05 (1H, bd, J=9.2 Hz), 5.72 (1H, bs), 5.45 (1H, d, J=9.2 Hz), 4.76 (2H, s), 3.11 (2H, m), 2.53 (1H, m), 1.80–1.10 (6H, m), 1.03 (9H, s), 0.82 (3H, m). LRMS: (m/z) 465 (M+H)⁺.

STEP D: 2(R)-[(N-Benzyloxy-N-formylamino)-methyl]-hexanoic Acid-[1'(S)-(bezofuran-2-carbonyl)-2',2'-dimethyl-propyl]-amide Purification by column chromatography (SiO₂, 2:1 ethyl acetate: hexanes) gave the title compound as a clear oil (24 mg, 52%)

¹H NMR (MeOD): 8.13 (0.5H, bs), 7.90 (0.5H, bs), 7.81 (2H, m), 7.70–7.25 (8H, m), 5.25 (1H, m), 4.90 (2H, m), 3.75 (2H, m), 2.90 (1H, m), 1.60–1.00 (6H, m), 0.98 (9H, s), 0.71 (3H, m). LRMS: (m/z) 493 (M+H)⁺, 515 (M+Na)⁺.

STEP E: 2(R)-[(N-Formyl-N-hydroxyamino)-methyl]-hexanoic Acid-[1(S)-(bezofuran-2-carbonyl)-2,2-dimethyl-propyl]-amide The title compound was isolated as a hygroscopic white crystalline solid (20 mg, 100%).

¹H NMR (MeOD): 8.27 (0.3H, s), 7.85 (1.7H, m), 7.80 (1H, d, J=7.8 Hz), 7.62 (1H, d, J=8.4 Hz), 7.54 (1H, t, J=7.8 Hz), 7.35 (1H, m), 5.35 (1H, br, s), 3.78 (1H, m), 3.62 (0.3H, dd, J=14.0, 5.6 Hz), 3.42 (0.7H, dd, J=14.0, 4.7 Hz), 3.09 (0.7H, m), 2.91 (0.3H, m), 1.42 (2H, m), 1.25–0.95 (13H, bm), 0.80–0.65 (3H, m). ¹³C NMR(MeOD): 191.5, 176.5, 157.7, 154.3, 130.4, 128.6, 125.7, 125.2, 116.3, 113.6, 62.5, 53.9, 45.5, 45.3, 36.2, 31.6, 30.6, 27.7, 24.0, 14.5. LRMS: (m/z) 401 (M–H)⁻, 403 (M+H)⁺, 425 (M+Na)⁺. MIC (*E. coli*): 6.25 μM MIC (*S. capitis*): 1.6 μM

EXAMPLE 9

N-[1(S)-(Benzofuran-2-carbonyl)-2,2-dimethylpropyl]-3'-cyclopentyl-2'(R)-[(N-formyl-N-hydroxyamino)-methyl]-propionamide

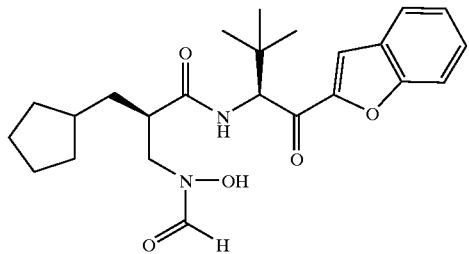

The title compound was prepared as described in Scheme 3 and the General Protocol (GP). Experimental details and relevant spectroscopic data are described below.

Scheme 3

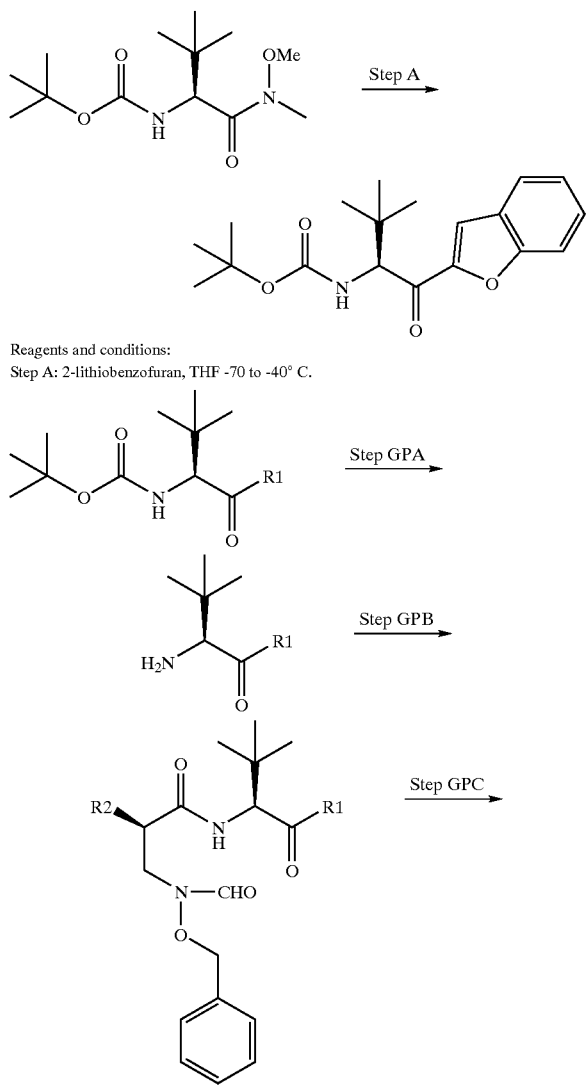

Reagents and conditions:
Step A: 2-lithiobenzofuran, THF -70 to -40° C.

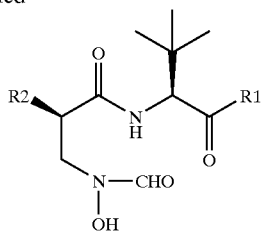

R1 = substituted aryl or 2-benzofuranyl
R2 = n-Butyl or Cyclopentlmethyl
Reagents and conditions:
Step GPA: HCl/dioxan
Step GPAB: EDC, HOBT and either 2(R)-[(N-Benzyloxy-N-formylamino)-methyl]-hexanoic acid or 2(R)-[(N-Benzyloxy-N-formylamino)-methyl]-3-cyclopentyl-propionic acid in DMF
Step GPC: H$_2$/Pd/C 10 wt%

General Protocol (GP)

STEP A: [1(S)-(Benzofuran-2-carbonyl)-2,2-dimethylpropyl]-carbamic Acid tert-butyl Ester A solution of benzofuran (4.24 g, 36 mmol) in dry THF (20 mL) under argon was cooled to −78° C. n-Butyllithium (22.5 mL, 36 mmol, 1.6M in hexanes) was added dropwise such that an internal temperature below −65° C. was maintained. The reaction was allowed to stir at −78° C. for two hours during which time 2-lithiobenzofuran precipitated as a white solid. The suspension of 2-lithiobenzofuran was added dropwise to a cooled (−78° C.) solution of [1(S)-(Methoxy-methyl-carbamoyl)-2,2-dimethylpropyl]-carbamic acid-tert-butyl ester (3.34 g, 12 mmol) in THF (30 mL) via cannula such that an internal temperature of below −65° C. was maintained. The yellow solution was allowed to stir at −70° C. for 30 minutes and −40° C. for a further 3 hours. The reaction was quenched by addition of saturated ammonium chloride solution (200 mL). The aqueous phase was extracted with ethyl acetate (3×150 mL) and the combined organic extracts washed with brine (2×200 mL), dried over magnesium sulphate, filtered and the solvents removed in vacuo to give a crude yellow oil. Purification by column chromatography (SiO$_2$, 10% ethyl acetate in hexanes) gave the title compound as a yellow solid (3.45 g, 87%).

$^1$H NMR (CDCl$_3$): δ/ppm 7.70 (2H, m), 7.62 (1H, m), 7.50 (1H, m), 7.31 (1H, m), 5.41 (1H, bd, J=9.1 Hz), 5.07 (1H, bd, J=9.7 Hz), 1.43 (9H, s), 1.02 (9H, s). LRMS: (m/z) 354 (M+Na)$^+$.

STEP GPA: 2(S)-Amino-1-benzofuran-2-yl-3,3-dimethylbutan-1-one

[1(S)-(Benzofuran-2-carbonyl)-2,2-dimethylpropyl]-carbamic acid tert-butyl ester (700 mg, 2.11 mmol) was dissolved in 1,4-dioxan saturated with HCl (10 mL) and the yellow solution allowed to stir at room temperature for 18 hours. The reaction was added to saturated sodium bicarbonate solution (50 mL) (CAUTION!) and the pH adjusted to 10 with the addition of 1M sodium carbonate. The aqueous mixture was extracted with ethyl acetate (3×100 mL) and the combined organic extracts washed with brine (3×100 mL), dried over magnesium sulphate, filtered and the solvents removed in vacuo to give the title compound as a pale yellow solid (480 mg, 98%).

Alternatively the α-aminoketones were isolated as hydrochloride salts by removal of the HCl/1,4-dioxan in vacuo.

$^1$H NMR (CDCl$_3$): δ/ppm 7.72 (1H, d, J=7.8 Hz), 7.55 (2H, m), 7.48 (1H, m), 7.32 (1H, t, J=7.5 Hz), 4.12 (1H, s), 1.65 (2H, bs), 1.02 (9H, s).

STEP GPB: N-[1(S)-(Benzofuran-2-carbonyl)-2,2-dimethylpropyl]-3'-cyclopentyl-2'(R)-[(N-benzyloxy-N-formylamino)-methyl]-propionamide To a solution of 2(R)-[(N-Benzyloxy-N-formylamino)-methyl]-3-cyclopentyl-propionic acid (247 mg, 0.81 mmol) in DMF (5 mL) at 0° C. was added EDC (157 mg, 0.81 mmol) and HOBT (22 mg, 20 mol %) and the mixture allowed to stir at 0° C. for 45 minutes. A solution of 2(S)-Amino-1-benzofuran-2-yl-3,3-dimethylbutan-1-one (149 mg, 0.65 mmol) in DMF (2 mL) was added and the reaction allowed to stir at ambient temperature for 18 hours. The solvent was removed in vacuo and the residue dissolved in ethyl acetate (50 mL) and ammonium chloride solution (50 mL). The organic layer was separated and the aqueous phase extracted with ethyl acetate (2×50 mL). The combined organic extracts were dried over magnesium sulphate, filtered and the solvents removed in vacuo to give a crude yellow oil. Purification by column chromatography (SiO$_2$, 2:1 hexanes: ethyl acetate) gave the title compound as a clear oil (196 mg, 58%).

Alternatively where the hydrochloride salts of the α-aminoketones were used the free amine was generated by the addition of 2 equivalents of TEA to the DMF solution of the α-aminoketone prior to addition to the HOBT ester.

$^1$H NMR (MeOD): δ/ppm 8.42–8.25 (1H, bm), 8.13 (0.5H, m), 7.90 (0.5H, m), 7.78 (1H, s), 7.60 (1H, m), 7.59–7.30 (7H, m), 5.25 (1H, m), 4.90 (2H, m), 3.72 (1.5H, m), 3.33 (0.5H, m), 2.95 (1H, m), 1.75 (1H, m), 1.65–1.10 (8H, m), 0.98 (9H, s), 0.94 (2H, m). LRMS: (m/z) 541 (M+Na)$^+$.

STEP GPC: N-[1(S)-(Benzofuran-2-carbonyl)-2,2-dimethylpropyl]-3'-cyclopentyl-2'(R)-[(N-formyl-N-hydroxyamino)-methyl]-propionamide N-[1(S)-(Benzofuran-2-carbonyl)-2,2-dimethylpropyl]-3'-cyclopentyl-2'(R)-[(N-benzyloxy-N-formylamino)-methyl]-propionamide (197 mg, 0.38 mmol) was dissolved in methanol (15 mL) under argon and a slurry of palladium on charcoal (20 mg) in ethyl acetate (1 mL) was added and hydrogen bubbled through the reaction for 10 minutes. An atmosphere of 1 bar of hydrogen was maintained via balloon and the reaction allowed to stir at ambient temperature for 1 hour. The reaction was filtered through glass wool and the solvents removed in vacuo. The residue was purified by reverse phase preparative HPLC to give the title compound as a white crystalline solid (84 mg, 52%).

$^1$H NMR (MeOD): δ/ppm 8.28 (0.4H, s), 7.83 (2.6H, m), 7.65–7.45 (2H, m), 7.35 (1H, t, J=7.0 Hz), 5.36 (1H, m), 3.77 (1H, dd, J=14.1, 9.5 Hz), 3.61 (0.3H, dd, J=14.0, 5.4 Hz), 3.43 (0.7H, dd, J=14.0, 4.6 Hz), 3.10 (0.7H, m), 2.93 (0.3H, m), 1.82–1.15 (9H, m), 1.05 (9H, s), 1.10–0.80 (2H, m). $^{13}$C NMR (MeOD): δ/ppm 191.5, 176.6, 157.8, 154.3, 130.4, 129.6, 125.7, 125.2, 116.3, 113.6, 62.5, 45.4, 39.4, 38.1, 36.3, 34.4, 33.8, 27.7, 26.3, 26.2. LRMS: (m/z) 451 (M+Na)$^+$. MIC (*E. coli*): 6.25 μM MIC (*S. capitis*): 0.7 μM

EXAMPLE 10

2(R)-[(N-Benzyloxy-N-formylamino)-methyl]-hexanoic Acid Pentafluorophenyl Ester

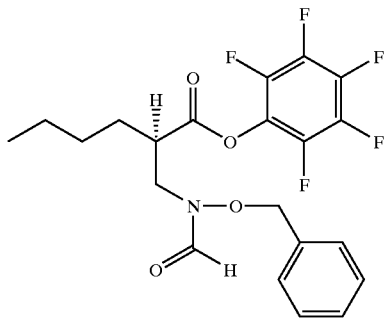

The title compound was prepared as described in Scheme 4. The experimental details of the synthesis and relevant spectroscopic data are described below.

Scheme 4

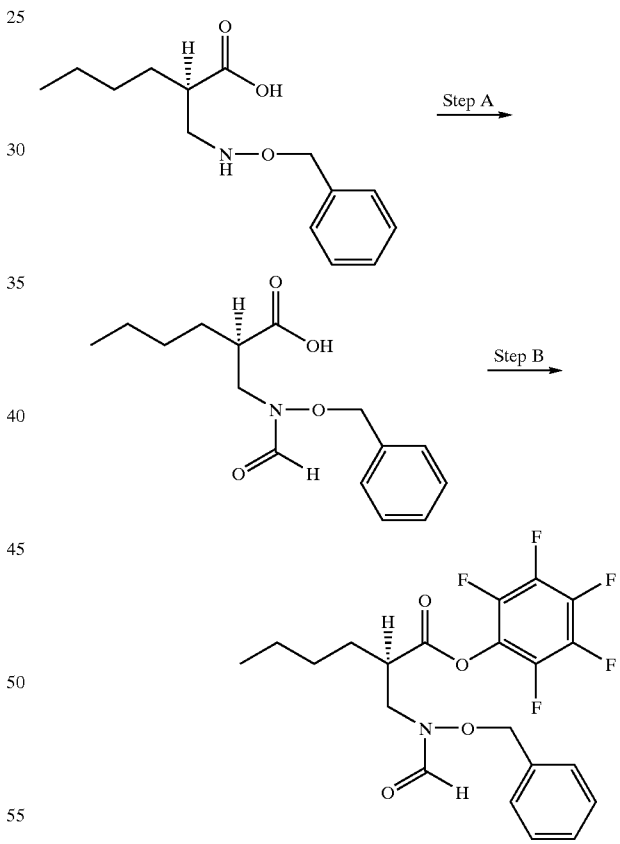

Reagents and conditions:
Step A: Formyl acetic anhydride, TEA, THF, 0° C., 1 hour then RT, 1 hour;
Step B: Pentafluorophenol, EDC, EtOAc, 0° C. to RT, O/N.

Step A: 2(R)-(N-Benzyloxy-N-formylamino)-methyl)-hexanoic Acid

To a solution of 2(R)-(N-benzyloxyamino-methyl)-hexanoic acid (30.6 g, 0.12 mol) in dry THF (300 ml) was added formic acetic anhydride (26.8 ml, 0.31 mol) at 0° C. Triethylamine (18.5 ml, 0.13 mol) was added and the reaction mixture was stirred for 1 hour at 0° C. and 60 hours at room temperature. The solvent was removed in vacuo to yield the title compound as a yellow oil (33.6 g, 99%) which was used in Step B without further purification.

¹H NMR (CDCl₃): δ/ppm (rotamers) 8.14 (0.7H, br s), 8.00 (0.3H, br s), 7.50–7.25 (5H, m), 5.07–4.70 (2H, m), 3.95–3.52 (2H, m), 2.78 (1H, br s), 1.72–1.20 (6H, m) and 0.89 (3H, br s). LRMS: (m/z) 280 (M+H)⁺.

Step B: 2(R)-[(N-Benzyloxy-N-formylamino)-methyl]-hexanoic Acid Pentafluorophenyl Ester To a solution of 2(R)-(benzyloxy-formylamino)-hexanoic acid (33.6 g, 0.12 mol) in dry THF (500 ml) was added pentafluorophenol (44.3 g, 0.24 mol), EDC (27.7 g, 0.14 mol) and hydroxybenzotriazole (16.2 g, 0.12 mol). The reaction was stirred overnight at room temperature. The solvent was removed in vacuo and the residue was dissolved in ethyl acetate, washed with 1 M Na₂CO₃ (3×500 ml) and water (1×500 ml) and dried over MgSO₄ and concentrated in vacuo to yield a yellow oil (60 g). The product was purified by flash chromatography (SiO₂, 5:1, hex:EtOAc to 1:2 hex:EtOAc) to yield a clear oil (42.0 g, 79%).

¹H NMR (CDCl₃): δ/ppm (rotamers) 8.15 (0.7H, br s), 8.01 (0.3H, br s), 7.60–7.21 (5H, m), 5.00–4.70 (2H, m), 4.04–3.72 (2H, m), 3.09 (1H, br s), 1.85–1.57 (2H, m), 1.50–1.26 (4H, m), 1.00–0.82 (3H, m). LRMS: (m/z) 468 (M+Na), 446 (M+H)⁺.

EXAMPLE 11
2(R)-[(N-Formyl-N-hydroxyamino)-methyl]-hexanoic Acid [1'-(2,4-dimethoxy-benzoyl)-2',2'-dimethylpropyl]-amide

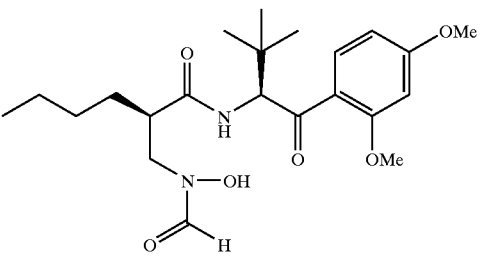

The title compound was prepared as described in Scheme 5. The experimental details of the synthesis and relevant spectroscopic data are described below.

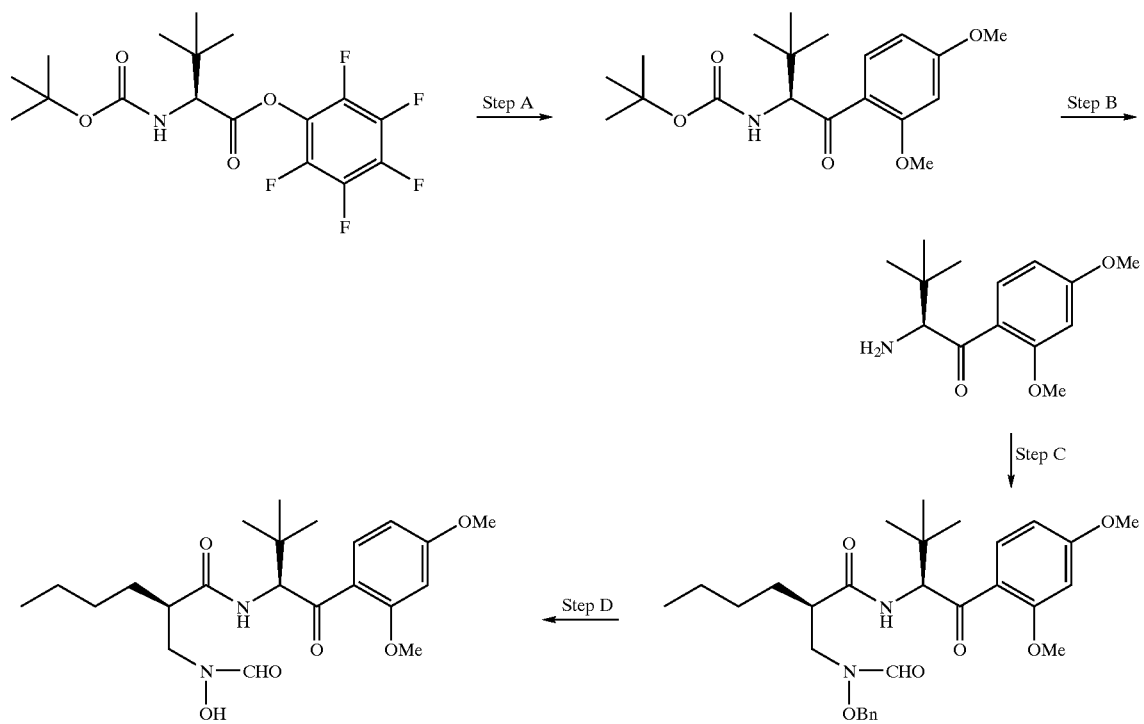

Reagents and conditions:
Step A: 4-lithio-3-methoxyanisole, THF -70° C.
Step B: HCl/dioxan
Step C: 2-(R)-[(N-benzyloxy-N-formylamino)methyl]-hexanoic acid pentafluorophenyl ester, TEA and DCM.
Step D: H₂/Pd/C STEP A: [1(S)-(2,4-Dimethoxy-benzoyl)-2,2-dimethylpropyl]-carbamic Acid tert-butyl Ester To a solution of 1-bromo-2,4-dimethoxybenzene (482 mg, 2.22 mmol) in dry THF (10 mL) at −78° C. under argon was added dropwise t-BuLi (2.96 mL, 4.44 mmol, 1.5M in pentanes). After addition was complete the reaction mixture was allowed to stir at −75° C. for one hour. Meanwhile a solution of 2-tert-Butoxycarbonylamino-3,3-dimethyl-butyric acid pentafluorophenyl ester (Example 14) (400 mg, 1.01 mmol) in dry THF (5 mL) was prepared at −75° C. under argon. The solution of 4-lithio-3-methoxyanisole was then added dropwise via cannula such that an internal temperature of less than −70° C. was maintained. The reaction was allowed to stir at −70° C. for 4 and a half hours before saturated ammonium chloride solution (30 mL) was added. The aqueous phase was extracted with ethyl acetate (3×30 mL) and the combined organic extracts washed with 1M sodium carbonate solution (3×100 mL) and brine (2×100 mL). The ethyl acetate phase was dried over magnesium sulphate, filtered and the solvents removed in vacuo to give a clear oil. Purification by column chromatography (SiO$_2$, 6:1 hexanes:ethyl acetate) gave the title compound as a clear oil (239 mg, 68%).

$^1$H NMR (CDCl$_3$): δ/ppm 7.70 (1H, d, J=8.6 Hz), 6.52 (1H, dd, J=8.7, 2.2 Hz), 6.42 (1H, m), 5.50 (1H, m), 5.40 (1H, d, J=9.7 Hz), 3.91 (3H, s), 3.86 (3H, s), 1.45 (9H, s), 0.88 (9H, s). LRMS: (m/z) 374 (M+Na)$^+$.

STEP B: 2(S)-Amino-1-(2,4-dimethoxy-phenyl)-3,3-dimethyl-butan-1-one.HCl

To [1(S)-(2,4-Dimethoxy-benzoyl)-2,2-dimethylpropyl]-carbamic acid tert-butyl ester (239 mg) at 0° C. was added 1–4 dioxan saturated with HCl (3 mL). The reaction solution was allowed to stir for 18 hours before the solvents were removed in vacuo and the residue azeotroped with DCM (3×10 mL) to give the title compound as a yellow solid (224 mg).

$^1$H NMR (MeOD): δ/ppm 7.74 (1H, d, J=9.3 Hz), 6.89 (2H, m), 5.12 (1H, s), 3.97 (3H, s), 3.89 (3H, s), 0.99 (9H, s). LRMS: (m/z) 252 (M+H)$^+$.

STEP C: 2(R)-[(N-Benzyloxy-N-formylamino) methyl]-hexanoic Acid [1'(S)-(2,4-dimethoxy-benzoyl)-2',2'-dimethylpropyl]-amide To a solution of 2-{2-[(N-Benzyloxy-N-formylamino) methyl]-hexanoylamino}-3,3-dimethyl-butyric acid pentafluorophenyl ester (303 mg, 0.681 mmol) in DCM (3 mL) at 0° C. was added triethylamine (131 mg, 1.29 mmol) followed by a solution of 2(S)-Amino-1-(2,4-dimethoxy-phenyl)-3,3-dimethyl-butan-1-one.HCl in DCM (2 mL). The reaction was allowed to warm to ambient temperature and stirred for 18 hours. Saturated ammonium chloride solution (50 mL) was added and the aqueous phase extracted with ethyl acetate (3×30 mL). The organic phases were washed with water (100 mL), 1M sodium carbonate solution (3×100 mL) and brine (100 mL), dried over magnesium sulphate, filtered and the solvents removed in vacuo to give a crude brown oil. Purification by column chromatography (SiO$_2$, 1:1 hexanes:ethyl acetate) gave the title product as a clear oil (153 mg 44%).

$^1$H NMR (CDCl$_3$): δ/ppm 8.13 (0.5, bs), 7.91 (0.5, bs), 7.69 (1H, bd, J=8.5 Hz), 7.60–7.30 (5H, m), 6.54 (1H, dd, J=8.7, 2.3 Hz), 6.40 (2H, m), 5.72 (1H, m), 5.00 and 4.80 (2H, m), 3.90 (3H, s), 3.85 (3H, s), 3.70 (1H, m), 3.10 (1H, m), 2.58 (1H, m), 1.55–1.10 (6H, m), 1.00–0.76 (12H, m). LRMS: (m/z) 513 (M+H)$^+$, 535 (M+Na)$^+$.

STEP D: 2(R)-[(N-Formyl-N-hydroxyamino) methyl]-hexanoic Acid [1'(S)-(2,4-dimethoxy-benzoyl)-2',2'-dimethylpropyl]-amide 2(R)-[(N-Benzyloxy-N-formylamino)methyl]-hexanoic Acid [1'(S)-(2,4-dimethoxy-benzoyl)-2',2'-dimethylpropyl]-amide (154 mg, 0.30 mmol) was dissolved in methanol (10 mL) under argon and a slurry of palladium on charcoal (15 mg) in ethyl acetate (1 mL) was added and hydrogen gas bubbled through the reaction solution for 10 minutes. The reaction was allowed to stir under a hydrogen atmosphere (balloon) for one hour. The reaction was filtered through glass wool and the solvents removed in vacuo to give the title compound as a white crystalline solid (99 mg, 78%).

$^1$H NMR (MeOD): δ/ppm 8.27 (0.4H, s), 8.19 (0.6H, bd, J=9.0 Hz), 8.10 (0.4H, bd, J=9.0 Hz), 7.85 (0.6H, s), 7.63 (1H, m), 6.62 (2H, m), 5.72 (1H, m), 3.90 (3.86 (3H, s), 3.85 (1H, m), 3.61 (0.4H, m), 3.41 (0.6H, dd, J=14.2, 4.6 Hz), 3.05 (0.6H, m), 2.90 (0.4H, m), 1.70–1.10 (6H, m), 0.90 (9H, bs), 0.82 (3H, m). $^{13}$C NMR (MeOD): δ/ppm 176.3, 175.9, 166.8, 162.3, 133.8, 123.7, 107.3, 99.9, 64.9, 64.8, 56.6, 53.4, 46.2, 45.9, 36.2, 31.6, 30.6, 27.9, 24.0, 14.6. LRMS: (m/z) 421 (M−H)$^−$, 423 (M+H)$^+$ 445 (M+Na)$^+$. MIC (E. coli): 25 μM MIC (S. capitis): 25 μM

EXAMPLE 12

2(R)-[(N-Formyl-N-hydroxyamino)-methyl]-hexanoic Acid [1'(S)-(4-hydroxy-benzoyl)-2',2'-dimethylpropyl]-amide

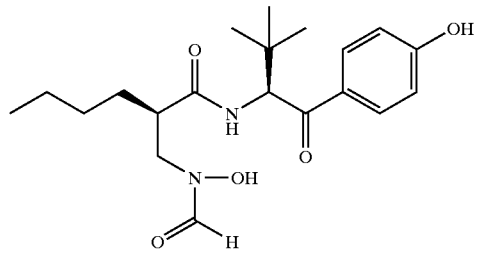

The title compound was prepared as described in Scheme 6. The experimental details of the synthesis and relevant spectroscopic data are described below.

Scheme 6

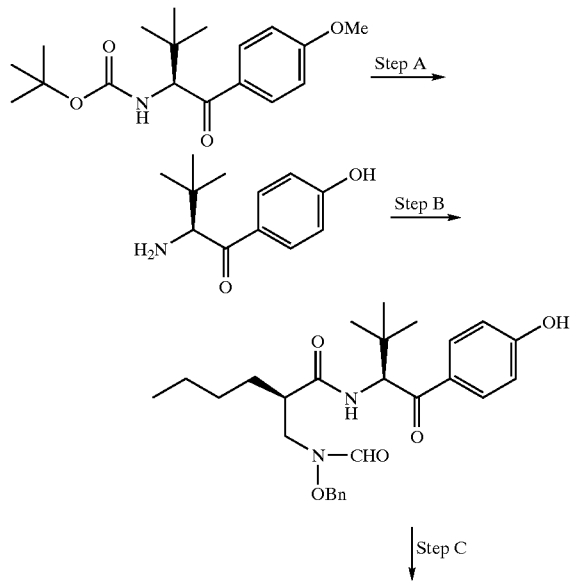

-continued

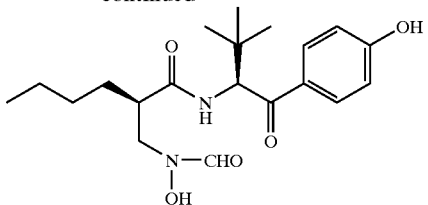

Reagents and conditions:
Step A: Boron tribromide
Step B: EDC, HOBT, and 2(R)-[(N-Benzyloxy-N-formylamino)-methyl]hexanoic acid, DMF
Step C: H₂/Pd/C 10 wt%

STEP A: 2(S)-Amino-1-(4-hydroxy-phenyl)-3,3-dimethyl-butan-1-one

To a solution of (1(S)-(4-Methoxybenzoyl)]-2,2-dimethylpropyl)carbamic acid-tert-butyl ester (191 mg, 0.86 mmol) in 1,2-dichloroethane (15 mL) at 0° C. was added dropwise BBr₃ (3 mL, 3 mmol, 1.0 M in DCM). The brown solution was allowed to warm to room temperature and stirred for 18 hours. The reaction mixture was again cooled to 0° C. and 1M HCl in methanol (15 mL) added cautiously. The yellow solution was allowed to warm to ambient temperature and stirred for two hours before the solvents were removed in vacuo to give a yellow solid. The residue was dissolved in 1M HCl (30 mL) and washed with toluene (15 mL) and diethyl ether (15 mL). The pH of the aqueous phase was adjusted to 8 with the addition of solid sodium bicarbonate. The aqueous phase was then extracted with ethyl acetate (3×70 mL), dried over magnesium sulphate and filtered. The solvents were removed in vacuo to give the title compound as a pinkish solid (148 mg, 83%).

¹H NMR (MeOD): δ/ppm 7.88 (2H, d, J=8.8 Hz), 6.83 (2H, d, J=8.9 Hz), 4.32 (1H, s), 0.93 (9H, s). LRMS: (m/z) 206 (M−H)⁻, 208 (M+H)⁺.

STEP B: 2(R)[(N-Benzyloxy-N-formylamino)-methyl]-hexanoic Acid [1'(S)-(4-hydroxy-benzoyl)-2,2-dimethylpropyl]-amide To a solution of 2(R)-[(N-Benzyloxy-N-formylamino)-methyl]-hexanoic acid (229 mg, 0.82 mmol) in DMF (10 mL) at 0° C. was added EDC (159 mg, 0.82 mmol) and HOBT (26 mg, 20 mol %) and the mixture allowed to stir at 0° C. for 30 minutes. A solution of 2(S)-Amino-1-(4-hydroxy-phenyl)-3,3-dimethyl-butan-1-one (140 mg, 0.68 mmol) in DMF (5 mL) was added and the reaction allowed to stir at ambient temperature for 18 hours. The solvent was removed in vacuo and the residue dissolved in ethyl acetate (30 mL) and water (70 mL). The organic layer was separated and the aqueous phase extracted with ethyl acetate (2×50 mL). The combined organic extracts were dried over magnesium sulphate, filtered and the solvents removed in vacuo to give a crude off white foam. Purification by column chromatography (SiO₂, 1:1 hexanes:ethyl acetate) gave the title compound as a white sticky foam (151 mg, 47%).

¹H NMR (CDCl₃): δ/ppm 8.93 (1H, bs), 8.15 (0.5H, bs), 7.95 (0.5H, bs), 7.84 (2H, d, J=8.8 Hz), 7.38 (5H, m), 6.88 (2H, d, J=8.7 Hz), 6.48 (1H, bd, J=9.1 Hz), 5.43 (1H, m), 4.90 (2H, bm), 3.75 (1.5H, bm), 3.12 (0.5H, bm), 2.60 (1H, m), 1.70–1.05 (6H, m), 0.93 (9H, s). LRMS: (m/z) 491 (M+Na)⁺.

STEP C: 2(R)-[(N-Formyl-N-hydroxyamino)-methyl]-hexanoic Acid [1'(S)-(4-hydroxy-benzoyl)-2',2'-dimethylpropyl]-amide 2(R)-[(N-Benzyloxy-N-formylamino)methyl]-hexanoic acid [1'(S)(4-hydroxy-benzoyl)-2',2'-dimethylpropyl]-amide (151 mg, 0.32 mmol) was dissolved in methanol (15 mL) under argon and a slurry of palladium on charcoal (20 mg) in ethyl acetate (1 mL) was added and hydrogen gas bubbled through the reaction solution for 10 minutes. The reaction was allowed to stir under a hydrogen atmosphere (balloon) for one hour. The reaction was filtered through glass wool and the solvents removed in vacuo to give the title compound as a white crystalline solid (119 mg, 98%). Purification on the ASPEC preparative HPLC system gave the title product in >95% purity (98 mg, 81%).

¹H NMR (MeOD): δ/ppm 8.27 (0.3H, s), 8.23 (0.7H, bd, J=9.4 Hz), 8.11 (0.3H, bd, J=9.2 Hz), 7.92 (2H, d, J=8.8 Hz), 7.86 (0.7H, s), 6.85 (2H, d, J=8.8 Hz), 5.48 (1H, m), 3.80 (1H, m), 3.61 (0.3H, dd, J=14.0, 5.7 Hz), 3.41 (0.7H, dd, J=14.2, 4.6 Hz), 3.02 (0.7H, m), 2.87 (0.3H, m), 1.60–1.30 (2H, m), 1.30–1.10 (4H, m), 0.96 (9H, s), 0.75 (3H, t, J=7.0 Hz). ¹³C NMR (MeOD): δ/ppm 176.7, 176.2, 164.6, 132.7, 131.2, 116.8, 60.5, 60.4, 53.9, 45.8, 45.5, 36.3, 31.6, 30.6, 27.9, 24.0, 14.5. LRMS: (m/z) 377 (M−H)⁻, 401 (M+Na)⁺. MIC (*E. coli*): 6.25 μM MIC (*S. capitis*): 12 μM

EXAMPLE 13

2(R)-[(N-Benzyloxy-N-formylamino)-methyl]-3-cyclopentyl-propionic Acid

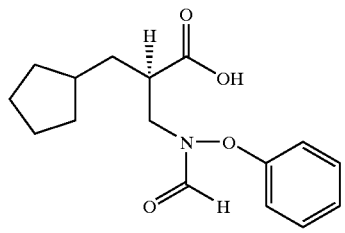

The title compound was prepared as described in Scheme 7. The experimental details of the synthesis and relevant spectroscopic data are described below.

Scheme 7

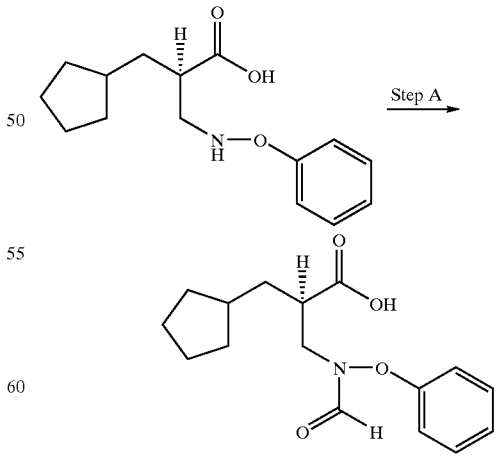

Reagents and conditions:
Step A: Formyl acetic anhydride, TEA, THF, 0° C., 1 hour then RT, 1 hour;

Step A: 2(R)-[(N-Benzyloxy-N-formylamino)-methyl]-3-cyclopentyl-propionic Acid 2(R)-(Benzyloxyamino-methyl)-3-cyclopentyl-propionic acid was prepared as described above.

Formic acetic anhydride (27.78 g, 0.32 mol) followed by TEA (52.7 mL, 0.38 mol) were added to a cooled (0° C.) solution of 2(R)-(benzyloxyamino-methyl)-3-cyclopentyl-propionic acid in THF (180 mL). The reaction mixture was stirred for 1 hour at 0° C. and then at room temperature for 1 hour before the solvent was removed in vacuo. The residue was purified by column chromatography (SiO$_2$, 25–100% EtOAc in hexanes) to give the title compound as a colourless oil (36.10 g, 94%).

$^1$H NMR (CDCl$_3$): δ/ppm 10.50–10.15 (1H, m), 8.23–7.87 (1H, m), 7.50–7.10 (5H, m), 5.13–4.67 (2H, m), 3.97–3.54 (2H, m), 2.95–2.67 (11H, m), 2.13–0.93 (11H, m). LRMS: (m/z) 328 (M+Na)$^+$; 304 (M−H)$^−$.

EXAMPLE 14

2(S)-tert-Butoxycarbonylamino-3,3dimethyl-butyric Acid Pentafluorophenyl Ester

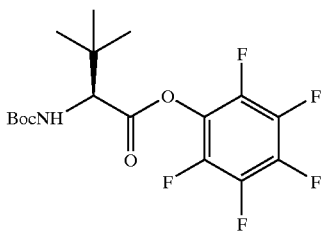

The title compound was prepared as described in Scheme 8. The experimental details of the synthesis and relevant spectroscopic data are described below.

Scheme 8

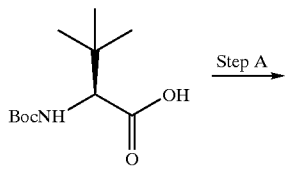

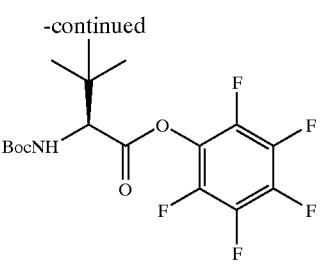

Reagents and conditions:

A. Pentafluorophenol, NMM, EDC, EtOAc, 0° C. to RT, O/N.

Step A: 2(S)-tert-Butoxycarbonylamino-3,3-dimethyl-butyric Acid Pentafluorophenyl Ester 2(S)-tert-Butoxycarbonylamino-3,3-dimethyl-butyric acid was prepared from L-tert-leucine according to Step A of Scheme 1.

Pentafluorophenol (8.75 g, 47.5 mmol) dissolved in EtOAc (5 mL) was added to a solution of 2(S)-tert-butoxycarbonylamino-3,3-dimethyl-butyric acid (10 g, 43 mmol) in EtOAC (35 mL) and the mixture cooled to 0° C. NMM (4.75 mL, 43 mmol) followed by EDC (9.12 g, 47.6 mmol) were added to this cooled solution and the reaction mixture was then allowed to warm to room temperature and stirred overnight. The reaction mixture was then diluted with EtOAc (200 mL) and washed with 1M HCl (2×200 mL), 1M Na$_2$CO$_3$ (3×200 mL) and brine, dried over MgSO$_4$ and concentrated in vacuo. The residue was purified by column chromatography (SiO$_2$, 10% EtOAc in hexanes) to give the title compound as a white solid (12.03 g, 70%).

$^1$H NMR (CDCl$_3$): δ/ppm 5.16–4.99 (1H, m), 4.41 (1H, d, J=9.4), 1.47 (9H, s) and 1.11 (9H, s). LRMS: (m/z) 420 (M+Na)$^+$.

EXAMPLE 15
2(R)-[(N-Formyl-N-hydroxyamino)-methyl]-hexanoic Acid-(1'(S)-tert-butyl-2'-oxo-3'-pyridin-2-yl-propyl) Amide

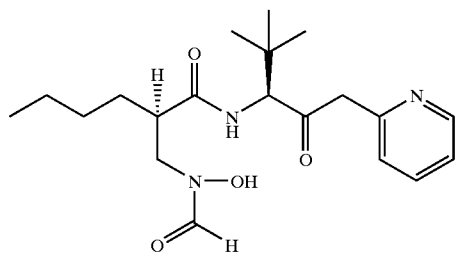

The title compound was prepared as described in Scheme 9. The experimental details of the synthesis and relevant spectroscopic data are described below.

Scheme 9

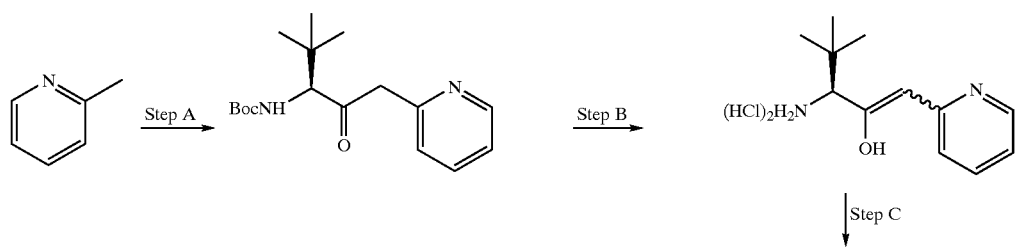

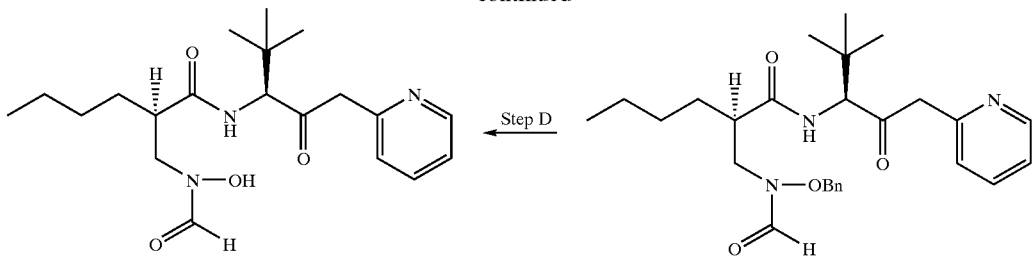

Reagents and Conditions:
Step A. (i) n-BuLi, THF, −40° C., 1 hour (ii) −78° C., 2(S)-tert-butoxycarbonylamino-3,3-dimethyl-butyric acid pentafluorophenyl ester/THF;
Step B. HCl/Dioxane, 2 hours, RT;
Step C. (i) 2(R)-[(benzyloxy-formyl-amino)-methyl]-hexanoic acid, EDC, HOBt, DMF, RT, 1.5 hours (ii) 3(S)-amino-4,4-dimethyl-1-pyridin-2-yl-pentan-2-one hydrochloride, NMM, DMF, RT, over W/E;
Step D. H₂, Pd/C, MeOH.

STEP A: (1(S)-tert-Butyl-2-oxo-3-pyridin-2-yl-propyl)carbamic Acid tert-butyl Ester The reaction was carried out under argon in flame dried apparatus. n-BuLi (1.6 M in hexanes, 11.3 mL, 18.1 mmol) was added dropwise to a cooled (−40° C.) solution of 2-picoline (1.64 mL, 16.6 mmol) in THF (30 mL). When addition was complete the solution was stirred at −40° C. for 1 hour before cooling to −78° C. A solution of 2(S)-tert-butoxycarbonylamino-3,3-dimethyl-butyric acid pentafluorophenyl ester (3.00 g, 7.6 mmol) in THF (30 mL) was added via a cannula, maintaining the reaction temperature below −65° C. After stirring for 1 hour at −78° C. saturated NH₄Cl solution (10 mL) was added and the reaction mixture was allowed to warm to room temperature before it was partitioned between EtOAc (200 mL) and saturated NH₄Cl solution (200 mL). The organic extract was washed with water (200 mL) and brine (200 mL), dried over MgSO₄ and concentrated in vacuo. The residue was purified by column chromatography (SiO₂, 25% Et₂O in hexanes) to give the title product as a bright yellow solid (1.01 g, 44%).

¹H NMR (CDCl₃): δ/ppm 8.57–8.51 (0.5H, m), 8.10 (0.5H, d, J=5.2 Hz), 7.69–7.49 (1H, m), 7.25–7.13 (1H, m), 6.95–6.84 (1H, m), 5.40–5.28 (1H, m), 5.28–5.14 (0.5H, m), 4.29 (0.5H, d, J=9.25 Hz), 4.09 (1H, s), 3.95 (0.5H, d, J=9.8 Hz), 1.44 (4.5H, s), 1.42 (4.5H, s), 1.02 (4.5H, s) and 1.01 (4.5H, s). [¹H NMR is complex due to the presence of E and Z enol tautomers.] LRMS: (m/z) 329 (M+Na)⁺.

STEP B: (E)- or (Z)-3(S)-Amino-4,4-dimethyl-1-pyridin-2-yl-pent-1-en-2-ol Hydrochloride (1(S)-tert-Butyl-2-oxo-3-pyridin-2-yl-propyl)-carbamic acid tert-butyl ester (300 mg, 1.0 mmol), was dissolved in dioxane saturated with HCl (20 mL) and the reaction mixture stirred at room temperature for 2 hours. The mixture was then concentrated in vacuo to give the title compound as a yellow solid (0.37 g) which was used in Step C without further purification.

¹H NMR (CD₃OD): δ/ppm 8.91 (1H, d, J=5.7 Hz), 8.73–8.60 (1H, m), 8.20–8.04 (2H, m), 5.16–4.77 (1H, m), 4.45 (1H, s), 1.23 (9H, s).

STEP C: 2(R)-[(N-Benzyloxy-N-formylamino)-methyl]-hexanoic Acid (1'(S)-tert-butyl-2'-oxo-3'-pyridin-2-yl-propyl) Amide EDC (0.16 g, 0.83 mmol) followed by HOBt (0.11 g, 0.81 mmol) was added to a solution of 2(R)-(benzyloxy-formylamino)methyl-hexanoic acid (0.18 g, 0.64 mmol) in DMF (3 mL) and the reaction mixture stirred for 1.5 hours at room temperature. A mixture of (E)- or (Z)-3(S)-amino-4,4-dimethyl-1-pyridin-2-yl-pent-1-en-2-ol hydrochloride (1.0 mmol) and NMM (0.23 mL, 2.1 mmol) in DMF (1.5 mL) was heated until a solution was obtained and added to the reaction mixture which was then stirred at room temperature for 72 hours. The solvent was removed by concentration in vacuo and the residue partitioned between ethyl acetate (30 mL) and water (15 mL). The organic phase was washed with saturated sodium bicarbonate solution (15 mL) and brine (15 mL), dried over MgSO₄, filtered and concentrated in vacuo. The residue was purified by column chromatography (SiO₂, 50% ethyl acetate in hexanes) to give the title compound as a bright yellow solid (0.20 g, 68%).

¹H NMR (CDCl₃): δ/ppm 8.58–6.21 (11H, m), 5.41–3.55 (6.5H, m), 2.66–2.46 (1H, m) and 1.73–0.67 (18H, m). [¹H NMR is complex due to the presence of E and Z enol tautomers.] LRMS: (m/z) 468 (M+H)⁺; 466 (M−H)⁻.

STEP D: 2(R)-[(N-Formyl-N-hydroxyamino)-methyl]-hexanoic Acid-(1'(S)-tert-butyl-2'-oxo-3'-pyridin-2-yl-propyl) Amide To a solution of 2(R)-[(N-benzyloxy-N-formylamino)-methyl]-hexanoic acid (1'(S)-tert-butyl-2'-oxo-3'-pyridin-2-yl-propyl) amide (0.20 g, 0.44 mmol) in methanol (40 mL) under an argon atmosphere was added a slurry of 10% Pd/C (20 mg) in ethyl acetate (1 mL). Hydrogen gas was bubbled through the reaction mixture for 5 minutes before leaving the reaction to stir under 1 atmosphere of hydrogen for 10 hours. The reaction mixture was then flushed with argon and filtered through a pad of glass microfibre filters. The filtrate was concentrated in vacuo to give the title compound as a bright yellow glass (0.15 g, 92%).

¹H NMR (CDCl₃): δ/ppm 8.73–6.65 (6H, m), 5.40–3.94 (2.5H, m), 3.94–3.24 (2H, m), 2.97–2.53 (1H, m), 1.73–1.10 (6H, m), [1.02, 1.00, 0.98 (9H, 3×s)] and 0.89–0.63 (3H, m). [¹H NMR is complex due to the presence of E and Z enol tautomers.] LRMS: (m/z) 378 (M+H)⁺; 376 (M−H)⁻. MIC (*S. capitis*): 100 μM EXAMPLE 16
2(R)-[(N-Formyl-N-hydroxyamino)-methyl]-hexanoic Acid [1'(S)-(4-methanesulfonyl-benzoyl)-2',2'-dimethyl-propyl]amide

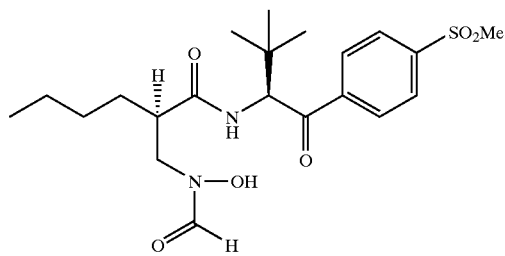

The title compound was prepared as described in Scheme 10. The experimental details of the synthesis and relevant spectroscopic data are described below.

Scheme 10

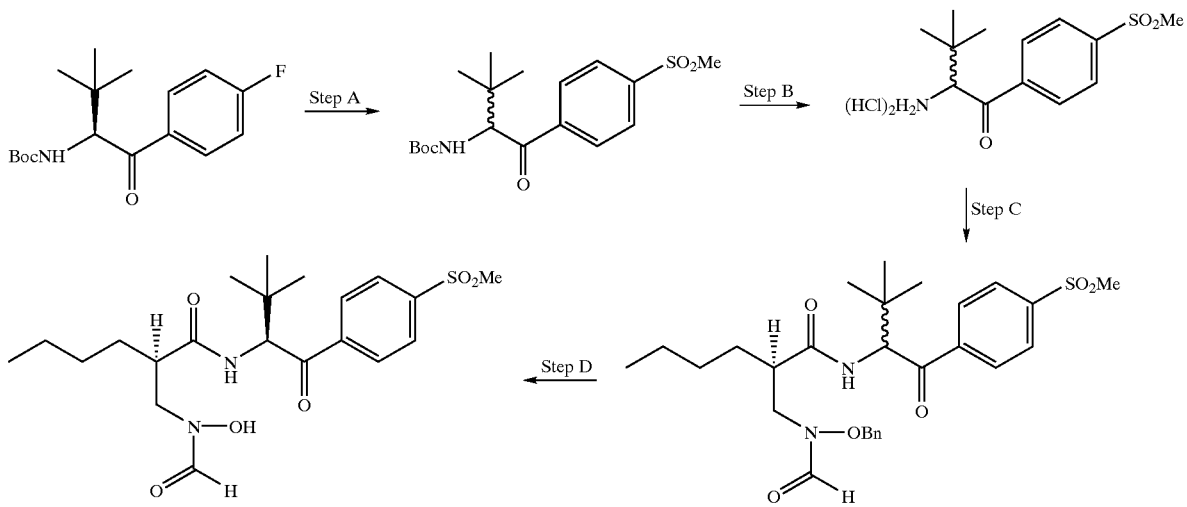

Reagents and conditions:

Step A: MeSO₂Na, DMSO, 130° C., O/N;
Step B: HCl/Dioxane, O/N, RT;
Step C: (i) 2(R)-[(Benzyloxy-formylamino)-methyl]-hexanoic acid, EDC, HOBt, DMF, RT, 1.5 hours (ii) 2(R)- and 2(S)-amino-1-(4-methanesulfonyl-phenyl)-3,3-dimethyl-butan-1-one hydrochloride, NMM, DMF, RT, O/N;
Step D: (i) H₂, Pd/C, MeOH, 3.5 hours, (ii) Prep. HPLC.

STEP A: Racemic mixture of 1 (R)- and 1(S)-(4-Methanesulfonyl-benzoyl)-2,2-dimethyl-propyl-carbamic Acid-tert-butyl Ester 1(S)-(4-fluorobenzoyl)-2,2-dimethylpropyl)carbamic acid-tert-butyl ester was prepared as described in steps A to C in Scheme 1 (version 2). Sodium methane sulphinate (132 mg, 1.3 mmol) was added to a solution of 1(S)-(4-fluorobenzoyl)-2,2-dimethylpropyl)carbamic acid-tert-butyl ester (200 mg, 0.6 mmol) in DMSO (4 mL) and the mixture stirred under argon at 130° C. for 17 hours. After cooling to room temperature the reaction mixture was partitioned between diethyl ether (100 mL) and water (100 mL), the organic extract washed with water (100 mL) and brine (100 mL), dried over MgSO₄, filtered and concentrated in vacuo. The residue was purified by column chromatography (SiO₂, 10% ethyl acetate in hexanes) to give the title compound as a white solid (0.22 g, 73%).
¹H NMR (CDCl₃): δ/ppm 8.18 (2H, d, J=8.4), 8.11–8.01 (2H, m), 5.42–5.27 (1H, m), 5.13 (1H, d, J=9.6), 3.08 (3H, s), 1.43 (9H, s) and 0.94 (9H, s). LRMS: (m/z) 392 (M+Na)⁺.

STEP B: 2(R)- and 2(S)-Amino-1-(4-methanesulfonyl-phenyl)-3,3-dimethyl-butan-1-one Hydrochloride 1 (R)- and 1(S)-4-Methanesulfonyl-benzoyl)-2,2-dimethyl-propyl-carbamic acid-tert-butyl ester (0.22 g, 0.6 mmol), was dissolved in dioxane saturated with HCl (20 mL) and the reaction mixture stirred at room temperature for 17 hours. The mixture was then concentrated in vacuo to give the title compound as a yellow solid which was used in Step C without further purification.
¹H NMR (MeOD): δ/ppm 8.34–8.12 (4H, m), 5.12 (1H, s), 3.20 (3H, s) and 1.04 (9H, s).

STEP C: (2R,1'R)- and (2R,1'S)-2-[(N-Benzyloxy-N-formylamino)-methyl]-hexanoic Acid [1'-(4-methanesulfonyl-benzoyl)2',2'-dimethylpropyl] amide EDC (98 mg, 0.51 mmol) followed by HOBt (70 mg, 0.52 mmol) were added to a solution of 2(R)-[(benzyloxy-formylamino)-methyl]-hexanoic acid (0.11 g, 0.39 mmol) in DMF (2 mL) and the reaction mixture stirred for an hour at room temperature. 2(R)- and 2(S)-amino-1-(4-methanesulfonyl-phenyl)-3,3-dimethyl-butan-1-one hydrochloride (0.6 mmol) and NMM (0.13 mL, 1.2 mmol) in DMF (1.0 mL) were heated until a solution was obtained, added to the reaction mixture and stirred overnight. The solvent was removed by concentration in vacuo and the residue partitioned between ethyl acetate (40 mL) and 1M HCl (40 mL). The organic phase was washed with saturated sodium bicarbonate solution (40 mL) and brine (40 mL), dried over MgSO₄, filtered and concentrated in vacuo. The residue was purified by column chromatography (SiO₂, 1.5% methanol in DCM) to give the title compound as a white solid (140 mg, 67%).
¹H NMR (CDCl₃): δ/ppm 8.30–7.92 (5H, m), 7.51–7.10 (5H, m), 6.50–6.17 (1H, m), 5.66–5.49 (0.4H, m), 5.49–5.33 (0.6H, m), 5.10–4.45 (2H, m), 3.93–3.53 (2H, m), 3.21–2.97 (3H, m), 2.68–2.49 (1H, m), 1.61–1.03 (6H, m) and 1.04–0.73 (12H, m). LRMS: (m/z) 553 (M+Na)⁺, 531 (M+H)⁺.

STEP D: (2R,1'R)- and (2R,1'S)-2-[(N-Formyl-N-hydroxyamino)-methyl]-hexanoic Acid [1'-(4-methanesulfonyl-benzoyl)-2',2'-dimethyl-propyl] amide To a solution of (2R,1'R)- and (2R,₁'S)-2-[(N-Benzyloxy-N-formylamino)-methyl]-hexanoic acid [1'-(4-methanesulfonyl-benzoyl)-2',2'-dimethylpropyl]amide (140 mg, 0.26 mmol) in methanol (30 mL) under an argon atmosphere was added a slurry of 10% Pd/C (14 mg) in ethyl acetate (1 mL). Hydrogen gas was bubbled through the reaction mixture for 5 minutes before leaving the reaction to stir under 1 atmosphere of hydrogen for 3.5 hours. The reaction mixture was then flushed with argon and filtered through a pad of glass microfibre filters. The filtrate was concentrated in vacuo and the residue purified by reverse phase HPLC to give the (2R, 1'S) isomer as a white solid (32 mg, 28%).

¹H NMR (MeOD): δ/ppm 8.24 (2H, d, J=8.5), 8.10 (2H, d, J=8.5), 7.95–7.56 (1H, m), 5.49–5.36 (1H, m), 3.86–3.36 (2H, m), 3.17 (3H, s), 3.15–2.80 (1H, m), 1.61–1.04 (6H, m), 1.04–0.90 (9H, m) and 0.84–0.78 (3H, m). ¹³C NMR (MeOD): δ/ppm (rotamers) 201.2, 201.1, 176.9, 176.6, 175.6, 146.3, 144.3, 144.1, 130.8, 129.9, 129.4, 128.6, 76.2, 62.7, 62.2, 53.9, 53.5, 45.4, 45.2, 44.5, 42.0, 36.0, 35.8, 32.4, 31.6, 30.5, 30.0, 28.7, 28.4, 24.0 and 14.6. LRMS: (m/z) 463 (M+Na)⁺, 441 (M+H)⁺; 439 (M−H)⁻. HPLC: 82%. MIC (*E. coli*): 6.25 µM MIC (*S. capitis*): 25 µM

EXAMPLE 17

3-Cyclopentyl-2(S)-[(N-formyl-N-hydroxyamino)-methyl]-N-[1'(R)-(4-methoxybenzoyl)-2',2'-dimethylpropyl]propionamide [Enantiomer of Example 5]

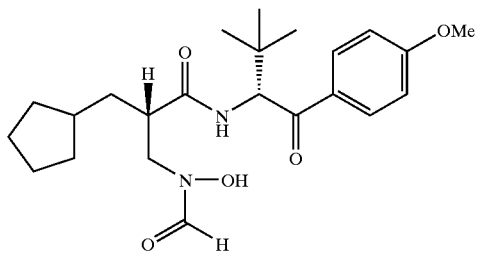

The title compound was prepared in an analogous manner to Example 5 as described in Scheme 1 utilising D-t-leucine in Step A and 2(S)-(benzyloxyamino-methyl)3-cyclopentyl-propionic acid in Step E. 2(S)-(benzyloxyamino-methyl)-3-cyclopentyl-propionic acid was synthesised in an analogous manner to 2(R)-(benzyloxyamino-methyl)-3-cyclopentyl-propionic acid using (R)-(+)-4-benzyl-2-oxazolidinone as the chiral auxilliary.

Spectral data was consistent with Example 5. MIC (*E. coli*): 100 µM MIC (*S. capitis*): 25 µM

EXAMPLE 18

2(R)-[(N-Formyl-N-hydroxyamino)-methyl]-hexanoic Acid-(1'(S)-(furan-2-carbonyl)-2',2'-dimethylpropyl)amide

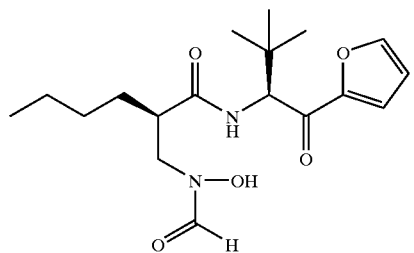

The title compound was prepared from furan in an analogous manner to that described in Scheme 2, using 2-lithiofuran in Step C. The relevant spectroscopic data are described below.

STEP C: 2(R)-(N-Benzyloxyaminomethyl)-hexanoic Acid-(1'(S)-(furan-2-carbonyl)-2',2'-dimethylpropyl)amide Purification by column chromatography (SiO₂, 5:1 iso-hexane:ethyl acetate) gave the product as a colourless oil (75 mg, 37%).

¹H NMR (CDCl₃): δ/ppm 7.69–7.63 (1H, m), 7.46–7.30 (5H, m), 7.33 (1H, d, J=3.5 Hz), 6.98 (1H, d, J=9.6 Hz), 6.57 (1H, dd, J=3.5, 1.7 Hz), 5.72 (1H, brs), 5.34 (1H, d, J=9.6 Hz), 4.75 (2H, s), 3.22–3.01 (2H, m), 2.60–2.44 (1H, m), 169–1.50 (1H, m), 1.50–1.34 (1H, m), 1.34–1.12 (4H, m), 1.01 (9H, s), 1.84 (3H, t, J=6.8 Hz). LRMS: (m/z) 414.8 (M+H)⁺.

STEP D: 2(R)-[(N-Benzyloxy-N-formylamino) methyl]-hexanoic Acid-(1'(S)-(furan-2-carbonyl)-2', 2'-dimethylpropyl)amide Purification by column chromatography (SiO₂, 4:1 to 2:1 iso-hexane:ethyl acetate) gave the product as a colourless oil (70 mg, 87%).

¹H NMR (CDCl₃): δ/ppm 8.04 (0.6H, brs), 7.90 (0.4H, brs), 7.65 (1H, d, J=1.7 Hz), 7.52–7.32 (5H, m), 7.32 (1H, d, J=3.5 Hz), 6.28 (1H, dd, J=3.5,1.7 Hz), 6.29 (1H, d, J=9.3 Hz), 5.27 (1H, d, J=9.2 Hz), 5.10–4.90 (1H, m), 4.90–4.72 (1H, m), 3.87–3.58 (2H, m), 3.20–3.01 (1H, m), 2.74–2.50 (1H, m), 1.65–1.46 (2H, m), 1.46–1.06 (4H, m), 0.95 (9H, s), 0.80 (3H, t, J=6.8 Hz). LRMS: (m/z) 423.2 (M+H)⁺, 465.2 (M+Na)⁺.

STEP E: 2(R)-[(N-formyl-N-hydroxyamino) methyl]-hexanoic Acid-(1'(S)-(furan-2-carbonyl)-2', 2'-dimethylpropyl)amide The title compound was isolated as a white crystalline solid (50 mg, 84%).

¹H NMR (CD₃OD): δ/ppm 8.35 (0.6H, d, J=8.8 Hz), 8.26 (0.2H, s), 8.24 (0.4H, d), 7.89–7.82 (1.8H, m), 7.46 (H, d, J=3.6 Hz), 6.67 (1H, dd, J=3.6, 1.7 Hz), 5.28–5.20 (1H, m), 3.85–3.70 (1H, m), 3.61 (0.4H, dd, J=14.0, 5.5 Hz), 3.41 (0.6H, dd, J=14.2, 4.6 Hz), 3.12–2.98 (0.6H, m), 2.96–2.82 (0.4H, m), 1.57–1.36 (2H, m), 1.36–1.12 (4H, m), 1.00 (3.6H, s), 0.99 (5.4H, s), 0.80 (3H, t, J=6.9 Hz). ¹³C NMR (CD₃OD): δ/ppm 189.5, 176.7, 176.4, 154.4, 149.7, 120.9, 114.2, 62.2, 62.1, 53.9, 50.3, 45.6, 45.3, 36.3, 31.6, 30.6, 27.7, 24.0, 14.6. LRMS: (m/z) 353.2 (M+H)⁺, 375.2 (M+Na)⁺, 351.2 (M−H)⁻. MIC (*E. coli*): 12.5 µM MIC (*S. capitis*): 12.5 µM

EXAMPLE 19

2(R)-[(N-Formyl-N-hydroxyamino)-methyl]-hexanoic Acid-(2',2'-dimethyl-1'(S)-(1-methyl-1H-pyrrole-2-carbonyl)-propyl)amide

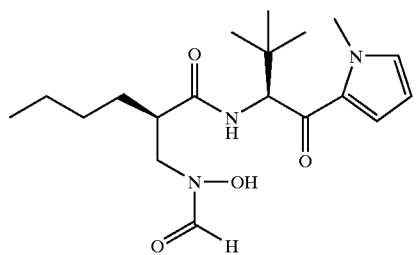

The title compound was prepared from 1-methylpyrrole in an analogous manner to that described in Scheme 5, using 2-lithio-1-methylpyrrole in Step A. The relevant spectroscopic data are described below.

STEP B: [2,2-dimethyl-1(S)-(1-methyl-1H-pyrrole-2-carbonyl)-propyl]-carbamic Acid tert-butyl Ester Purification by column chromatography (SiO₂, 18:1 iso-hexane:ethyl acetate) gave the product as an orange oil (0.18 g, 80%).

¹H NMR (CDCl₃): δ/ppm 7.19–7.12 (1H, m), 6.90–6.84 (1H, m), 6.19–6.12 (1H, m), 5.48 (1H, d, J=9.6 Hz), 4.82 (1H, d, J=9.6 Hz), 3.94 (3H, s), 1.44 (9H, s), 0.98 (9H, s). LRMS: (m/z) 295.2 (M+H)⁺.

STEP C: 2(S)-Amino-3,3-dimethyl-1-(1-methyl-1H-pyrrol-2-yl)-butan-1-one Hydrochloride The title compound was isolated as a pale purple solid and used without further purification (0.13 g, 100% crude).

¹H NMR (CD₃OD): δ/ppm 7.15–7.08 (1H, m), 6.93–6.87 (1H, m), 6.18–6.10 (1H, m), 4.61 (1H, brs), 3.93 (3H, s), 1.02 (9H, s). LRMS: (m/z) 195.0 (M+H)⁺.

STEP D: 2(R)-[(N-Benzyloxy-N-formylamino) methyl]-hexanoic Acid-(2',2'-dimethyl-1'(S)-(1-methyl-1H-pyrrole-2-carbonyl)-propyl)amide Purification by column chromatography (SiO₂, 4:1 to 1:1 iso-hexane:ethyl acetate) gave the product as a pale brown oil (0.16 g, 68%).

¹H NMR (CDCl₃): δ/ppm 8.13 (0.6H, brs), 7.92 (0.4H, brs), 7.56–7.28 (5H, m), 7.21–7.12 (1H, m), 6.92–6.83 (1H, m), 6.31 (1H, d, J=9.7 Hz), 6.25 (1H, dd, J=3.8, 2.6 Hz), 5.17 (1H, d, J=9.7 Hz), 5.08–4.91 (1H, m), 4.91–4.73 (1H, m), 3.92 (3H, s), 3.89–3.54 (2H, m), 3.19–3.02 (1H, m), 2.64–2.48 (1H, m), 1.64–1.32 (2H, m), 1.32–1.07 (4H, m), 0.96 (9H, s), 0.80 (3H, t, J=7.0 Hz). LRMS: (m/z) 456.2 (M+H)⁺, 478.2 (M+Na)⁺.

STEP E: 2(R)-[(N-formyl-N-hydroxyamino) methyl]-hexanoic Acid-(2',2'-dimethyl-1'(S)-(1-methyl-1H-pyrrole-2-carbonyl)-propyl)amide The title compound was isolated as a pale brown crystalline solid (60 mg, 80%).

¹H NMR (CD₃OD): δ/ppm 8.26 (0.5H, brs), 8.18 (0.5H, d, J=9.4 Hz), 8.07 (0.5H, brd, J=10.1 Hz), 7.85 (0.5H, s), 7.19 (1H, d, J=3.8 Hz), 7.10–7.00 (1H, m), 6.15 (1H, dd, J=3.7, 2.4 Hz), 5.25–5.15 (1H, m), 3.90 (3H, s), 3.88–3.71 (1H, m), 3.70–3.52 (0.5H, m), (0.5H obs. by CD₃OD peak), 3.11–2.92 (0.5H, m), 2.92–2.76 (0.5H, m), 1.63–1.31 (2H, m), 1.31–1.05 (4H, m), 0.99 (4.5H, s), 0.97 (4.5H, s), 0.76 (3H, t, J=6.8 Hz). ¹³C NMR (CD₃OD): δ/ppm 190.5, 176.4, 176.1, 134.5, 132.7, 122.9, 109.7, 61.9, 61.8, 53.9, 50.2, 45.8, 45.6, 38.3, 36.4, 31.6, 30.6, 28.1, 24.0, 14.6. LRMS: (m/z) 366.2 (M+H)⁺, 388.2 (M+Na)⁺, 363.8 (M−H)⁻. MIC (E. coli): 12.5 µM MIC (S. capitis): 12.5 µM

EXAMPLE 20

2(R)-[(N-Formyl-N-hydroxyamino)-methyl]-hexanoic Acid-(1'(S)-(4-aminobenzoyl)-2',2'-dimethylpropyl)amide

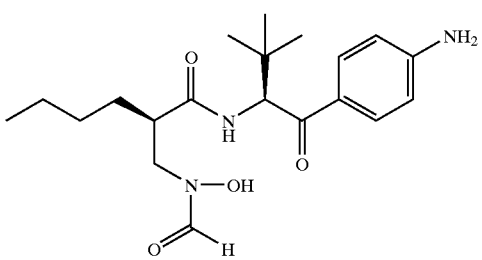

The title compound was prepared in as described in Scheme 11, using the General Protocol (GP) thereafter. The experimental details of the synthesis and relevant spectroscopic data are described below.

Scheme 11

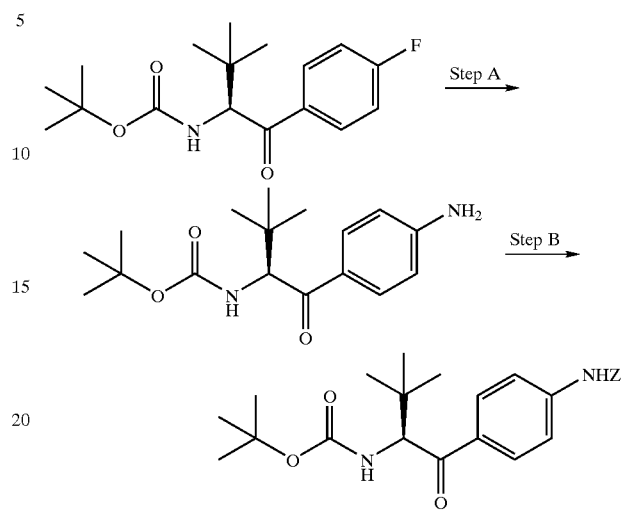

Reagents and Conditions:

A. NaN₃, DMF
B. Benzyl chloroformate, pyridine, DCM

STEP A: [1(S)-(4-Aminobenzoyl)-2,2-dimethylpropyl]-carbamic Acid tert-butyl Ester Sodium azide (1.26 g, 19.4 mmol) was added to a solution of [1(S)-(4-fluorobenzoyl)-2,2-dimethylpropyl]-carbamic acid tert-butyl ester (0.20 g, 0.7 mmol) in DMF (15 mL), and the mixture heated at 120° C. for 40 hours. The solvent was removed in vacuo before addition of 10% NaHCO₃ (aq.) (30 mL) to the residual solid. The aqueous phase was extracted with ethyl acetate (2×30 mL) and the organic phases washed with brine (1×30 mL), dried over MgSO₄, filtered and the solvent removed in vacuo to give a yellow solid. Purification by column chromatography (SiO₂, 4:1 iso-hexane:ethyl acetate) afforded the title compound as a yellow solid (67 mg, 36%).

¹H NMR (CDCl₃): δ/ppm 7.85 (2H, d, J=8.5 Hz), 6.65 (2H, d, J=8.6 Hz), 5.45 (1H, brd, J=9.2 Hz), 5.08 (1H, d, J=9.6 Hz), 4.17 (2H, brs), 1.42 (9H, s), 0.93 (9H, s). LRMS: (m/z) 329.2 (M+Na)⁺.

STEP B: [4-(2(S)-tert-Butoxycarbonylamino-3,3-dimethylbutyryl)-phenyl]-carbamic Acid Benzyl Ester A solution of [1(S)-(4-aminobenzoyl)-2,2-dimethylpropyl]-carbamic acid tert-butyl ester (67 mg, 0.22 mmol) and triethylamine (95 µL, 0.69 mmol) in DCM (3 mL) was cooled on an ice bath prior to addition of benzyl chloroformate (98 µL, 0.69 mmol). The reaction was warmed to room temperature and left for 15 hours. Examination by T.l.c. suggested minimal conversion to product hence pyridine (0.10 mL, 1.2 mmol) was added and the reaction left for a further 2 hours. Solvent was removed in vacuo and the residue taken up in ethyl acetate (20 mL). The organic phase was washed with 1M HCl (1×20 mL), brine (1×20 mL), 1M Na₂CO₃ (1×20 mL) and brine (1×20 mL, dried over MgSO₄, filtered and the solvent removed in vacuo, giving a yellow solid. Purification by column chromatography (SiO₂, 9:1 isohexane:ethyl acetate) afforded the title compound as a yellow solid (90 mg, 90%).

¹H NMR (CDCl₃): δ/ppm 7.77 (1H, d, J=8.7 Hz), 7.50 (1H, d, J=8.7 Hz), 7.42–7.32 (5H, m), 7.00 (1H brs), 5.43 (1H, brd, J=9.5 Hz), 5.22 (2H, s), 5.12 (1H, d, J=9.7 Hz), 1.42 (9H, s), 0.91 (9H, s). LRMS: (m/z) 463.2 (M+Na)⁺, 439.2 (M–H)⁻.

STEP GPA: [4-(2(S)-amino-3,3-dimethylbutyryl)-phenyl]-carbamic Acid Benzyl Ester Hydrochloride The title compound was isolated as a foam and used without further purification (75 mg, 100% crude).

¹H NMR (CDCl₃): δ/ppm 8.88 (0.5H, brs), 8.41–8.21 (3H, m), 7.59–7.50 (2.5H, m), 7.30–7.21 (2H, m, obs. by CDCl₃ peak), 7.432–7.31 (5H, m), 7.00 (1H brs), 4.86–4.68 (1H, m), 5.15 (2H, s), 1.04 (9H, s). LRMS: (m/z) 341.2 (M+H)⁺, 363.2 (M+Na)⁺.

STEP GPB: [4-(2(S)-{2(R)-(N-Formyl-N-hydroxyamino)-methyl]-hexanoylamino}-3,3-dimethylbutyryl)-phenyl]-carbamic Acid Benzyl Ester Purification by column chromatography (SiO₂, 4:1 iso-hexane:ethyl acetate) afforded the title compound as a pale brown oil (50 mg, 42%).

¹H NMR (CDCl₃): δ/ppm 8.13 (0.4H, brs), 8.04–7.80 (2.6H, m), 7.78–7.52 (1H, m), 7.57 (2H, d, J=8.7), 7.45–7.28 (10H, m), 6.38 (1H, d, J=9.3 Hz), 5.46 (1H, d, J=9.3 Hz), 5.20 (2H, s), 5.08–4.86 (1H, m), 4.86–4.70 (1H, m), 3.89–3.54 (2H, m), 2.62–2.50 (1H, m), 1.62–1.27 (2H, m), 1.27–1.05 (4H, m), 0.88 (9H, s), 0.75 (3H, t, J=6.9 Hz). LRMS: (m/z) 602.2 (M+H)⁺, 624.2 (M+Na)⁺, 600.2 (M–H)⁻.

STEP GPC: 2(R)-[(N-Formyl-N-hydroxyamino)-methyl]-hexanoic Acid-(1'(S)-(4-aminobenzoyl)-2',2'-dimethylpropyl)amide The title compound was isolated as a white crystalline solid (29.5 mg, 100%).

¹H NMR (CD₃OD): δ/ppm 8.27 (0.3H, s), 8.11 (0.7H, s, J=9.3 Hz), 8.00 (0.3H, d, J=9.4 Hz), 7.86 (0.7H, s), 7.80 (2H, d, J=8.8 Hz), 6.65 (2H, d, J=8.8 Hz), 5.44 (1H, d, J=9.4 Hz), 3.8 (1H, dd, J=14.2, 9.7 Hz), 3.61 (0.5H, dd, J=13.8, 5.4 Hz), 3.41 (0.5H, dd, J=14.2, 4.6 Hz), 3.09–2.93 (1H, m), 1.59–1.30 (2H, m), 1.30–1.03 (4H, m), 0.96 (4.5H, s), 0.95 (4.5H, s), 0.75 (3H, t, J=6.9 Hz). ¹³C NMR (CD₃OD): 199.2, 176.4, 176.1, 156.1, 132.8, 127.6, 114.7, 29.9, 53.9, 50.3, 45.9, 45.6, 36.4, 31.9, 30.6, 28.0, 24.0, 14.5. LRMS: (m/z) 400.2 (M+Na)⁺. MIC (*E. coli*): 6.25 μM MIC (*S. capitis*): 12.5 μM

EXAMPLE 21

2(R)-[(N-Formyl-N-hydroxyamino)-methyl]-hexanoic Acid-(2',2'-dimethyl-1'(S)-[4-(2,2,2-trifluoroacetylamino)-benzoyl]-propyl)amide

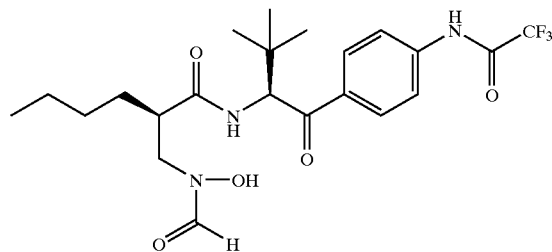

The title compound was prepared as described in Scheme 12, using the General Procedure (GP) thereafter. The experimental details of the synthesis and relevant spectroscopic data are described below.

Scheme 12

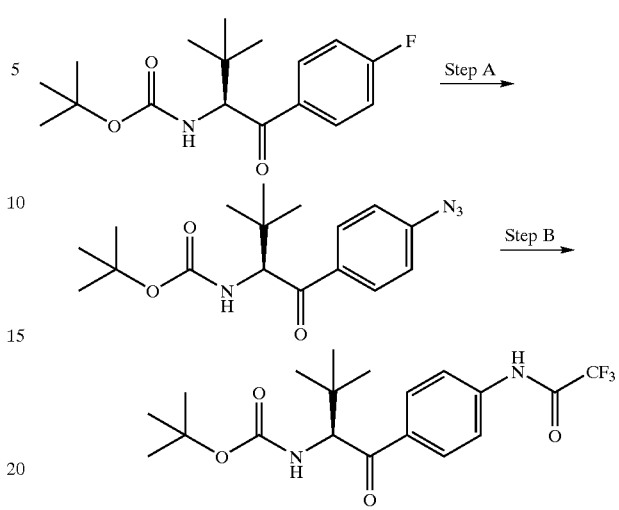

Reagents and Conditions:

A. NaN₃, DMF, 120° C.
B. i) H₂, 10% Pd-C, MeOH, ii) Trifluoroacetic anhydride, pyridine, DCM STEP A: [1(S)-(4-Azidobenzoyl)-2,2-dimethylpropyl]-carbamic Acid tert-butyl Ester Sodium azide (37.9 g, 0.58 mol) was added to a solution of [1(S)-(4-fluorobenzoyl)-2,2-dimethylpropyl]-carbamic acid tert-butyl ester (6.0 g, 19.4 mmol) in DMF (400 mL), and the mixture heated at 120° C. for 24 hours. The solvent was removed in vacuo and the residual solid taken up in ethyl acetate (200 ml). The organic phase was washed with 1M Na₂CO₃ (1×400 ml) and brine (1×400 mL), dried over MgSO₄, filtered and the solvent removed in vacuo to give a yellow solid. Purification by column chromatography (SiO₂, 6:1 iso-hexane:ethyl acetate) afforded the title compound as a yellow solid (1.96 g) and [1(S)-(4-Azidobenzoyl)-2,2-dimethylpropyl]-carbamic acid tert-butyl ester as an orange solid (0.97 g) (47% combined yield).

¹H NMR (CDCl₃): δ/ppm 8.01 (2H, d, J=8.7 Hz), 7.09 (2H, d, J=8.7 Hz), 5.37 (1H, brd, J=9.4 Hz), 5.10 (1H, d, J=9.6 Hz), 1.43 (9H, s), 0.93 (9H, s). LRMS: (m/z) 327.2 (M+H)⁺, 355.2 (M+Na)⁺.

STEP B: (2,2-dimethyl-1(S)-[4-(2,2,2-trifluoroacetylamino)-benzoyl]-propyl)-carbamic Acid tert-butyl Ester To a degassed solution of [1(S)-(4-azidobenzoyl-2,2-dimethylpropyl]-carbamic acid tert-butyl ester (1.0 g, 3.0 mmol) in methanol (10 mL) was added 10% palladium on charcoal (0.20 g). Hydrogen gas was bubbled through the suspension for 15 minutes when a balloon containing hydrogen was introduced to the reaction. After 15 hours, the catalyst was removed by filtration and washed liberally with methanol and DCM. The solvents were removed in vacuo to give a pale cream solid (1.0 g). The crude material was mixed with DCM (20 mL) and dissolution occurred on addition of triethylamine (0.63 mL, 3.16 mmol). The mixture was cooled to 0° C. (ice bath) and trifluoroacetic anhydride (0.45 mL, 3.16 mmol) was added dropwise. After 2 hours, further triethylamine (0.3 mL, 2.2 mmol) and trifluoroacetic anhydride (0.30 mL, 2.11 mmol) were added and the reaction proceeded for a further 2 hours. The solvent was removed in vacuo and ethyl acetate (20 mL) added to the residue. The organic phase was washed with 10% citric acid (aq.) (1×40 mL) and brine (1×40 mL), dried over MgSO₄, filtered and the solvent removed in vacuo to give a brown oil. Purification by column chromatography (SiO₂, 9:1 iso-hexane:ethyl acetate) afforded the title compound as a pale brown oil (0.63 g, 52%).

¹H NMR (CDCl₃): δ/ppm 8.58 (1H, brs), 8.00 (2H, d, J=8.6 Hz), 7.69 (2H, dd, J=8.5, 1.9 Hz), 5.42 (1H, brd, J=9.4 Hz), 5.10 (1H, d, J=9.5 Hz), 1.43 (9H, s), 0.93 (9H, s). LRMS: (m/z) 425.2 (M+Na)⁺.

STEP GPA: N-[4-(2(S)-Amino-3,3-dimethylbutyryl)-phenyl]-2,2,2-trifluoroacetamide The title compound was recovered as a pale brown solid and used without further purification (0.55 g, 100% crude).
¹H NMR (CD₃OD): δ/ppm 8.12 (2H, d, J=8.8 Hz), 7.90 (2H, d, J=8.8 Hz), 5.04 (1H, s), 1.05 (9H, s). LRMS: (m/z) 303.2 (M+H)⁺, 325.2 (M+Na)⁺.

STEP GPB: 2(R)-[(N-Benzyloxyl-N-formylamino)-methyl]-hexanoic Acid-(2',2'-dimethyl-1'(S)-[4-(2,2,2-trifluoroacetylamino)-benzoyl]-propyl)-amide Purification by column chromatography (SiO₂, 8:1 iso-hexane:ethyl acetate) afforded the title compound as a pale brown oil (0.4 g, 44%).
¹H NMR (CDCl₃): δ/ppm 9.03 (1H, brs), 8.13 (0.6H, brs), 8.00 (2H, d, J=8.7), 7.91 (0.4H, brs), 7.72 (2H, d, J=8.8), 7.43–7.32 (5H, m), 6.36 (1H, d, J=8.9 Hz), 5.42 (1H, d, J=9.0 Hz), 5.08–4.90 (1H, m), 4.90–4.74 (1H, m), 3.95–3.75 (1H, m), 3.75–3.58 (1H, m), 2.68–2.55 (1H, m), 1.62–1.30 (2H, m), 1.30–1.05 (4H, m), 0.88 (9H, s), 0.78 (3H, t, J=6.9 Hz). LRMS: (m/z) 564.2 (M+H)⁺, 686.2 (M+Na)⁺.

STEP GPC: 2(R)-[(N-Formyl-N-hydroxyamino)-methyl]-hexanoic Acid-(2',2'-dimethyl-1'(S)-[4-(2,2,2-trifluoroacetylamino)-benzoyl]-propyl)amide Purification by reverse phase preparative HPLC yielded the title compound as a white glassy solid (20 mg, 50%).
¹H NMR (CDCl₃): δ/ppm 8.27 (0.3H, s), 8.06 (2H, d, J=8.7 Hz), 7.90–7.78 (2.7H, m), 5.46 (1H, s), 3.88–3.72 (1H, m), 3.61 (0.3H, dd, J=14.2, 5.8 Hz), 3.42 (0.7H, dd, J=14.1, 4.3 Hz), 3.10–2.96 (0.7H, m), 2.95–2.80 (0.3H, m), 1.59–1.30 (2H, m), 1.30–1.04 (4H, m), 0.99 (3H, s), 0.98 (6H, s) and 0.75 (3H, t, J=6.9 Hz). ¹³C NMR (CDCl₃): δ/ppm 200.6, 200.4, 177.0, 176.7, 176.4, 157.3 (q, J=38 Hz), 142.9, 136.7, 131.2, 122.0, 117.7 (q, J=288 Hz), 61.1, 45.6, 45.4, 36.1, 31.6, 30.5, 27.8, 24.0, 14.5. LRMS: (m/z) 474.2 (M+H)⁺, 496.2 (M+Na)⁺, 472.2 (M–H)⁻. MIC (*E. coli*): 6.25 μM MIC (*S. capitis*): 6.25 μM

EXAMPLE 22

2(R)-[(N-Formyl-N-hydroxyamino)-methyl]-hexanoic Acid-(1'(S)-(4-acetylaminobenzoyl)-2',2'-dimethylpropyl)amide

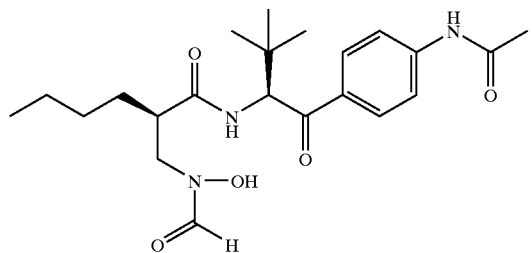

The title compound was prepared from 2(R)-[(N-benzyloxyl-N-formylamino)-methyl]-hexanoic acid-(2',2'-dimethyl-1'(S)-[4-(2,2,2-trifluoroacetylamino)-benzoyl]-propyl)-amide as described in Scheme 13. The experimental details of the synthesis and relevant spectroscopic data are described below.

Scheme 13

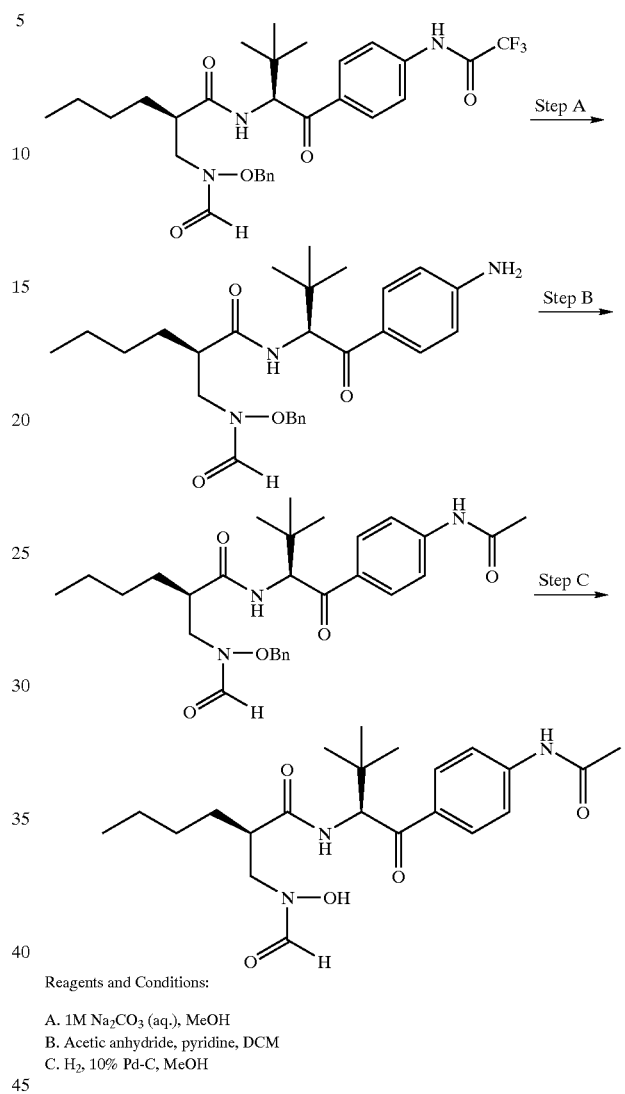

Reagents and Conditions:

A. 1M Na₂CO₃ (aq.), MeOH
B. Acetic anhydride, pyridine, DCM
C. H₂, 10% Pd-C, MeOH

STEP A: 2(R)-[(N-Benzyloxyl-N-formylamino)-methyl]-hexanoic Acid-(1'(S)-(4-aminobenzoyl]-2',2'-dimethylpropyl)-amide To a solution of 2(R)-[(N-benzyloxyl-N-formylamino)-methyl]-hexanoic acid-(2',2'-dimethyl-1'(S)-[4-(2,2,2-trifluoroacetylamino)-benzoyl]-propyl)-amide (0.35 g, 0.62 mmol) in methanol (4 mL) was added 1M Na₂CO₃. The reaction was left at room temperature for 4 hours when the mixture was extracted with ethyl acetate (2×20 mL). The organic phases were washed with brine (1×20 mL) and dried over MgSO₄, filtered and the solvent removed in vacuo. The resulting foam was purified by column chromatography (SiO₂, 4:1 iso-hexane:ethyl acetate) afforded the title compound as a pale brown oil (0.23 g, 79%).
¹H NMR (CDCl₃): δ/ppm 9.03 (1H, brs), 8.13 (0.6H, brs), 7.91 (0.4H, brs), 7.85 (2H, d, J=8.67), 7.46–7.32 (5H, m), 6.64 (2H, d, J=8.7), 6.38 (1H, d, J=9.3 Hz), 5.43 (1H, d, J=9.4 Hz), 5.09–4.90 (1H, m), 4.90–4.74 (1H, m), 3.90 (2H, m), 2.62–2.48 (1H, m), 1.612–1.28 (2H, m), 1.28–1.03 (4H, m), 0.90 (9H, s), 0.76 (3H, t, J=6.9 Hz). LRMS: (m/z) 468.2 (M+H)⁺, 490.2 (M+Na)⁺, 466.4 (M–H)⁻.

STEP B: 2(R)[(N-Benzyloxyl-N-formylamino)-methyl]-hexanoic Acid-(1'(S)-(4-acetylaminobenzoyl]-2',2'-dimethylpropyl)-amide A solution of 2(R)-[(N-benzyloxyl-N-formylamino)-methyl]-hexanoic acid-(1'(S)-(4-aminobenzoyl]-2',2'-dimethylpropyl)-amide (0.1 g, 0.21 mmol) in DCM (2 mL) was cooled to 0° C. (ice bath) before addition of pyridine (34.6 µl, 0.43 mmol) and acetyl chloride (30.5 µl, 0.43 mmol). The reaction was warmed to room temperature and left for 15 hours. The solvent was removed in vacuo and the residue dissolved in ethyl acetate (10 mL). The organic phase was washed with brine (1×20 mL), dried over MgSO$_4$, filtered and the solvent removed in vacuo, affording a pale brown oil which was used without further purification (0.11 g, 100% crude).

$^1$H NMR (CDCl$_3$): δ/ppm 8.13 (1H, brs), 7.96 (2H, d, J=8.7), 7.82 (1H, brs), 7.62 (2H, d, J=8.8), 7.43–7.32 (5H, m), 6.37 (1H, d, J=9.2 Hz), 5.45 (1H, d, J=9.3 Hz), 5.08–4.90 (1H, m), 4.90–4.74 (1H, m), 3.92–3.58 (2H, m), 2.66–2.52 (1H, m), 2.20 (3H, s), 1.62–1.30 (2H, m), 1.30–1.05 (4H, m), 0.88 (9H, s), 0.78 (3H, t, J=6.9 Hz). LRMS: (m/z) 510.4 (M+H)$^+$, 532.4 (M+Na)$^+$.

STEP C: 2(R)-[(N-Formyl-N-hydroxyamino)-methyl]-hexanoic Acid-(1'(S)-(4-acetylaminobenzoyl)-2',2'-dimethylpropyl)amide To a degassed solution of 2(R)-[(N-benzyloxyl-N-formylamino)-methyl]-hexanoic acid-(1'(S)-(4-acetylaminobenzoyl]-2',2'-dimethylpropyl)-amide (0.11 g, 0.21 mmol) in methanol (2 mL) was added 10% palladium on charcoal (20 mg). Hydrogen gas was bubbled through the suspension for 10 minutes when a balloon containing hydrogen was introduced to the reaction. After 2 hours, the catalyst was removed by filtration and the solvents were removed in vacuo to give a pale brown solid. Purification by reverse phase preparative HPLC afforded the title compound as a white crystalline solid (54 mg, 61%).

$^1$H NMR (CD$_3$OD): δ/ppm 8.30 (0.6H, d, J=9.1 Hz), 8.27 (0.4H, s), 8.19 (0.4H, d, J=9.1 Hz), 7.99 (2H, d, J=8.8 Hz), 7.86 (0.6H, s), 7.71 (2H, d, J=8.8 Hz), 5.47 (1H, d, J=9.1 Hz), 3.88–3.72 (1H, m), 3.61 (0.3H, dd, J=13.9, 5.7 Hz), 3.41 (0.7H, dd, J=14.1, 4.6 Hz), 3.09–2.95 (0.7H, m), 2.95–2.80 (0.3H, m), 2.15 (3H, s), 1.59–1.30 (2H, m), 1.30–1.04 (4H, m), 0.96 (9H, s), 0.74 (3H, t, J=7.0 Hz). $^{13}$C NMR (CD$_3$OD): δ/ppm 200.4, 176.6, 176.3, 172.4, 159.8, 145.4, 134.8, 131.3, 120.6, 60.8, 53.9, 50.3, 4537, 45.5, 36.2, 31.6, 30.6, 27.9, 24.5, 34.0, 14.5. LRMS: (m/z) 420.2 (M+H)$^+$, 442.2 (M+Na)$^+$, 418.4 (M–H)$^-$. MIC (E. coli): 12.5 µM MIC (S. capitis): 3.1 µM

EXAMPLE 23

2(R)-[(N-Formyl-N-hydroxyamino)-methyl]-hexanoic Acid-(1'(S)-(4-methanesulfonylaminobenzoyl)-2',2'-dimethylpropyl)amide

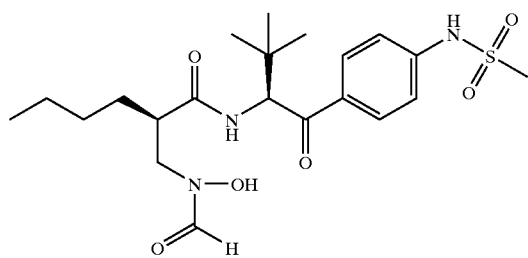

The title compound was prepared in an analogous manner to 2(R)-[(N-formyl-N-hydroxyamino)-methyl]-hexanoic acid-(1'(S)-(4-acetylaminobenzoyl)-2',2'-dimethylpropyl) amide as described in Scheme 13, using methanesulfonyl chloride in Step B. The relevant spectroscopic data are described below.

STEP B: 2(R)-[(N-Benzyloxyl-N-formylamino)-methyl]-hexanoic Acid-(1'(S)-(4-methanesulfonylaminobenzoyl]-2',2'-dimethylpropyl)-amide The title compound was afforded as a pale brown oil and used without further purification (0.10 g, 91% crude).

$^1$H NMR (CDCl$_3$): δ/ppm 8.29 (1H, s), 8.15 (0.5H, brs), 8.03–7.94 (2.5H, m), 7.82 (1H, brs), 7.62 (2H, d, J=8.8), 7.45–7.32 (7H, m), 6.45 (1H, d, J=9.2 Hz), 5.46 (1H, d, J=9.3 Hz), 5.10–4.90 (1H, m), 4.90–4.76 (1H, m), 4.04–3.84 (1H, m), 3.82–3.62 (1H, m), 3.69 (3H, s), 2.70–2.57 (1H, m), 1.62–1.32 (2H, m), 1.32–1.05 (4H, m), 0.90 (9H, s), 0.77 (3H, t, J=6.9 Hz). LRMS: (m/z) 546.2 (M+H)$^{+,}$ $^{568.2}$ (M+Na)$^+$.

STEP C: 2(R)-[(N-Formyl-N-hydroxyamino)-methyl]-hexanoic Acid-(1'(S)-(4-methanesulfonylaminobenzoyl)-2',2'-dimethylpropyl)amide Purification by reverse phase preparative HPLC afforded the title compound as a pale brown crystalline solid (30 mg, 31%).

$^1$H NMR (CD$_3$OD): δ/ppm 8.30 (0.4H, d, J=9.2 Hz), 8.27 (0.4H, s), 8.19 (0.6H, d, J=8.7 Hz), 8.02 (2H, d, J=8.8 Hz), 7.86 (0.6H, s), 7.33 (2H, d, J=8.8 Hz), 5.46 (1H, d, J=9.0 Hz), 3.87–3.72 (1H, m), 3.61 (0.3H, dd, J=14.1, 5.7 Hz), 3.42 (0.7H, dd, J=14.2, 4.6 Hz), 3.06 (3H, s), 3.09–2.95 (0.7H, m), 2.95–2.80 (0.3H, m), 1.59–1.30 (2H, m), 1.30–1.02 (4H, m__, 0.98 (3H, s), 0.97 (6H, s), 0.76 (3H, t, J=7.0 Hz). $^{13}$C NMR (CD$_3$OD): δ/ppm 200.4, 200.3, 176.7, 176.4, 159.8, 145.2, 134.7, 131.9, 119.4, 60.8, 53.9, 50.3, 45.7, 45.4, 40.4, 36.2, 31.6, 30.6, 27.9, 24.0, 14.6. LRMS: (m/z) 456.2 (M+H)$^+$, 478.2 (M+Na)$^+$, 454.4 (M–H)$^-$. MIC (E. coli): 50 µM MIC (S. capitis): 3.1 µM

EXAMPLE 24

2(R)-[(N-Formyl-N-hydroxyamino)-methyl]-hexanoic Acid-(2',2'-dimethyl-1'(S)-(4-morpholin-4-ylbenzoyl)-propyl)amide

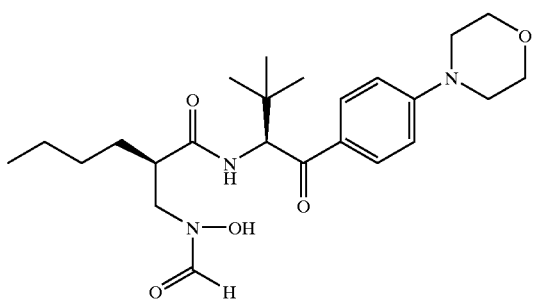

The title compound was prepared in as described in Scheme 14, followed by the General Protocol (GP). The experimental details of the synthesis and relevant spectroscopic data are described below.

Scheme 14

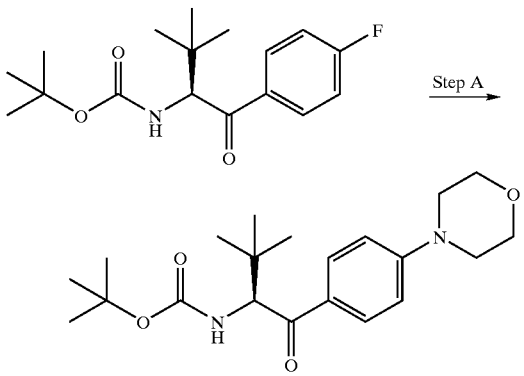

Reagents and Conditions:
A. Morpholine, DMSO, Et₃N, 120° C.

Reagents and Conditions:
A. Morpholine, DMSO, Et₂N, 120° C.

Scheme 14

STEP A: [2,2-Dimethyl-1(S)-(4-morpholin-4-ylbenzoyl)-propyl]-carbamic Acid tert-butyl Ester Morpholine (1.41 mL, 16.2 mmol) and triethylamine (0.25 mL, 1.8 mmol) were added to a solution of [1(S)-(4-fluorobenzoyl)-2,2-dimethylpropyl]-carbamic acid tert-butyl ester (0.5 g, 1.62 mmol) in DMSO (8 mL), and the mixture heated at 120° C. for 15 hours. The solvent was removed in vacuo and the residual solid taken up in ethyl acetate (30 ml), and washed with 10% citric acid (aq.) (1×40 ml). The aqueous layer re-extracted with ethyl acetate (1×30 mL) and the combined organic phases were washed with brine (1×40 mL), dried over MgSO₄, filtered and the solvent removed in vacuo to give a pale brown oil which was used without further purification (0.63 g, 100% crude).

$^1$H NMR (CDCl₃): δ/ppm 7.95 (2H, d, J=9.0 Hz), 6.88 (2H, d, J=9.0 Hz), 5.46 (1H, brd, J=9.6 Hz), 5.10 (1H, d, J=9.7 Hz), 3.90–3.82 (4H, m), 3.38–3.28 (4H, m), 1.42 (9H, s), 0.93 (9H, s). LRMS: (m/z) 377.2 (M+H)⁺, 399.2 (M+Na)⁺.

STEP GPA: 2(S)-Amino-3,3-dimethyl-1-(4-morpholin-4-ylphenyl)-butan-1-one

The title compound was recovered as pale brown solid and used without further purification (0.52 g, 100% crude).

$^1$H NMR (CDCl₃): δ/ppm 8.06 (2H, d, J=9.0 Hz), 7.31 (2H, d, J=9.0 Hz), 4.96 (1H, s), 3.99–3.89 (4H, m), 3.55–3.45 (4H, m), 1.04 (9H, s). LRMS: (m/z) 277.2 (M+H)⁺, 299.2 (M+Na)⁺.

STEP GPB: 2(R)-[(N-Benzyloxy-N-formylamino)-methyl]-hexanoic Acid-(2',2'-dimethyl-1'(S)-4-morpholin-4-ylbenzoyl)-propyl)-amide Purification by column chromatography (SiO₂, 2:1 to 2:3 iso-hexane:ethyl acetate) afforded the title compound as a pale brown oil (0.63 g, 72%).

$^1$H NMR (CDCl₃): δ/ppm 8.13 (0.6H, brs), 8.98–7.88 (0.4, m), 7.94 (2H, d, J=8.8 Hz), 7.48–7.30 (5H, m), 6.86 (2H, d, J=9.0), 6.36 (1H, d, J=9.3 Hz), 5.46 (1H, d, J=9.4 Hz), 5.10–4.90 (1H, m), 4.90–4.75 (1H, m), 3.90–3.80 (4H, m), 3.90–3.53 (2H, m), 3.38–3.28 (4H, m), 2.62–2.50 (1H, m), 1.60–1.30 (2H, m), 1.30–1.02 (4H, m), 0.90 (9H, s), 0.76 (3H, t, J=6.9 Hz). LRMS: (m/z) 538.4 (M+H)⁺, 560.4 (M+Na)⁺, 536.4 (M−H)⁻.

STEP GPC: 2(R)-[(N-Formyl-N-hydroxyamino)-methyl]-hexanoic Acid-(2',2'-dimethyl-1'(S)-(4-morpholin-4-ylbenzoyl)-propyl)amide Purification by reverse phase preparative HPLC yielded the title compound as a pale beige foam (0.36 g, 69%).

$^1$H NMR (CD₃OD): δ/ppm 8.27 (0.3H, s), 7.93 (2H, d, J=9.0 Hz), 7.85 (0.7H, s), 6.97 (2H, d, J=9.1 Hz), 5.46 (1H, s), 3.88–3.73 (5H, m), 3.61 (0.3H, dd, J=13.8, 5.8 Hz), 3.41 (0.7H, dd, J=14.2, 4.6 Hz), 3.39–3.27 (4H, m), 3.09–2.92 (0.7H, m), 2.92–2.78 (0.3H, m), 1.57–1.28 (2H, m), 1.28–1.00 (4H, m), 0.97 (3H, s), 0.95 (6H, s), 0.74 (3H, t, J=7.0 Hz). $^{13}$C NMR (CD₃OD): δ/ppm 199.6, 176.5, 176.2, 19.8, 156.7, 132.3, 129.4, 114.8, 68.1, 60.2, 53.9, 50.3, 48.9, 45.8, 45.6, 36.3, 31.6, 30.6, 27.9, 24.0, 14.6. LRMS: (m/z) 448.2 (M+H)⁺, 470.2 (M+Na)⁺, 446.4 (M−H)⁻. MIC (*E. coli*): 6.25 μM MIC (*S. capitis*): 3.1 μM

EXAMPLE 25

2(R)-[(N-Formyl-N-hydroxyamino)-methyl]-hexanoic Acid-(1'(S)-[4-(4-benzylpiperazin-1-yl)-benzoyl]-2',2'-dimethylpropyl)amide

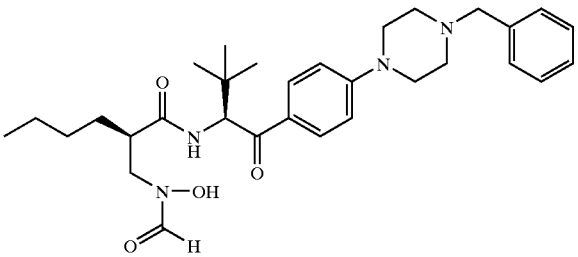

The title compound was prepared utilising 1-benzylpiperazine in Step A as described in Scheme 14, and using the General Protocol (GP) thereafter. The relevant spectroscopic data are described below.

STEP A: [1(S)-[4-(4-Benzylpiperazin-1-yl)-benzoyl]-2,2-dimethylpropyl]-carbamic Acid tert-butyl Ester.

1-Benzyloxycarbonyl piperazine (0.45 g, 2.03 mmol) Purification by column chromatography (SiO₂, 5:1 iso-hexane:ethyl acetate) afforded the title compound as a yellow oil (0.68 g, 82%).

$^1$H NMR (CDCl₃): δ/ppm 7.91 (2H, d, J=8.9 Hz), 7.38–7.28 (5H, m), 6.84 (2H, d, J=9.1 Hz), 5.46 (1H, brd, J=9.4 Hz), 5.10 (1H, d, J=9.6 Hz), 3.56 (2H, s), 3.41–3.33 (4H, m), 3.62–3.55 (4H, m), 1.42 (9H, s), 0.93 (9H, s). LRMS: (m/z) 466.2 (M+H)⁺, 488.2 (M+Na)⁺.

STEP GPA: 2(S)-1-[4-(4-Benzylpiperazin-1-yl)-phenyl]-3,3-dimethyl-butan-1-one Dihydrochloride The title compound was recovered as an orange foam and used without further purification (0.12 g, 100% crude).

$^1$H NMR (CD₃OD): δ/ppm 8.00 (2H, d, J=9.0 Hz), 7.66–7.58 (2H, m), 7.54–7.47 (3H, m), 7.11 (2H, d, J=9.0 Hz), 4.92 (1H, s), 4.44 (2H, s), 4.25–4.12 (2H, m), 3.62–3.51 (2H, m), 3.40–3.26 (4H, m), 1.03 (9H, s). LRMS: (m/z) 366.2 (M+H)⁺, 388.2 (M+Na)⁺.

STEP GPB: 2(R)-[(N-Benzyloxy-N-formylamino)-methyl]-hexanoic Acid-(1'(S)-[4-(4-benzylpiperazin-1-yl)-benzoyl]-2',2'-dimethylpropyl)amide Purification by column chromatography (SiO₂, 2:1 ethyl acetate:iso-hexane) afforded the title compound as a pale yellow oil (37 mg, 24%).

¹H NMR (CDCl₃): δ/ppm 8.13 (0.6H, brs), 7.98–7.87 (0.4, m), 7.93 (2H, d, J=8.8 Hz), 7.48–7.30 (5H, m), 6.85 (2H, d, J=9.0), 6.35 (1H, d, J=9.3 Hz), 5.45 (1H, d, J=9.3 Hz), 5.10–4.90 (1H, m), 4.90–4.75 (1H, m), 3.87–3.58 (2H, m), 3.56 (2H, s), 3.42–3.31 (4H, m), 2.63–2.50 (5H, m), 1.62–1.28 (2H, m), 1.28–1.05 (4H, m), 0.90 (9H, s), 0.76 (3H, t, J=6.9 Hz). LRMS: (m/z) 663.4 (M+Na)⁺.

STEP GPC: 2(R)-[(N-Formyl-N-hydroxyamino)-methyl]-hexanoic Acid-(1'(S)[4-(4-benzylpiperazin-1-yl)-benzoyl]-2',2'-dimethylpropyl)amide Trifluoroacetic Acid Purification by reverse phase preparative HPLC afforded the title compound as a colourless crystalline solid (10 mg, 27%).

¹H NMR (CD₃OD): δ/ppm 8.26 (0.4H, s), 8.24 (0.3H, d, J=9.8 Hz), 8.13 (0.3H, d, J=9.1 Hz), 7.97 (2H, d, J=8.9 Hz), 7.84 (0.6H, s), 7.59–7.48 (5H, m), 7.06 (2H, d, J=8.9 Hz), 5.46 (0.5H, d, J=5.6 Hz), 5.45 (0.5H, d, J=9.1 Hz), 4.42 (2H, s), 3.79 (1H, dd, J=14.1, 8.8 Hz), 3.59 (1H, dd, J=14.3, 5.8 Hz), 3.55–3.26 (8H, m), 3.10–2.95 (0.4H, m), 2.95–2.80 (0.6H, m), 1.56–1.31 (2H, m), 1.31–1.01 (4H, m), 0.96 (4H, s), 0.95 (5H, s), 0.75 (3H, t, J=6.9). ¹³C NMR (CD₃OD): δ/ppm 199.8, 176.3, 154.9, 132.8, 132.3, 131.9, 131.0, 130.9, 130.4, 116.0, 62.0, 60.5, 53.9, 52.7, 50.3, 46.3, 45.6, 45.5, 36.3, 31.6, 30.6, 27.9, 24.0, 14.6. LRMS: (m/z) 533.4 (M+H)⁺, 559.4 (M+Na)⁺. MIC (*E. coli*): 50 µM MIC (*S. capitis*): 3.1 µM

EXAMPLE 26

2(R)-[(N-Formyl-N-hydroxyamino)-methyl]-hexanoic Acid-(2',2'-dimethyl-1'(S)-(4-piperazin-1-yl-benzoyl)-propyl)amide

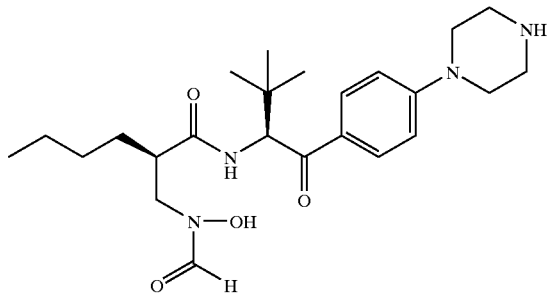

The title compound was prepared using 1-benzyloxycarbonylpiperazine in Step A as described in Scheme 14, and using the General Protocol (GP) thereafter. The experimental details of the synthesis and relevant spectroscopic data are described below.

STEP A: 4-[4-(2(S)-tert-Butoxycarbonylamino-3,3-dimethylbutyryl)-phenyl]-piperazine-1-carboxylic Acid Benzyl Ester Purification by column chromatography (SiO₂, 5:1 isohexane:ethyl acetate) afforded the title compound as a yellow oil (0.68 g, 82%).

¹H NMR (CDCl₃): δ/ppm 7.93 (2H, d, J=8.9 Hz), 7.40–7.30 (5H, m), 6.85 (2H, d, J=9.0 Hz), 5.42 (1H, brd, J=8.9 Hz), 5.17 (2H, s), 5.10 (1H, d, J=9.0 Hz), 3.70–3.62 (4H, m), 3.40–3.32 (4H, m), 1.42 (9H, s), 0.93 (9H, s). LRMS: (m/z) 332.4 (M+Na)⁺.

STEP GPA: 4-[4-(2(S)-Amino-3,3-dimethylbutyryl)-phenyl]-piperazine-1-carboxylic Acid Benzyl Ester Hydrochloride The title compound was recovered as a red foam and used without further purification (0.17 g, 100% crude).

¹H NMR (CD₃OD): δ/ppm 8.02 (2H, d, J=9.0 Hz), 7.51 (2H, d, J=9.0 Hz), 7.42–7.25 (5H, m), 5.17 (2H, s), 5.05 (1H, s), 3.89–3.79 (4H, m), 3.67–3.52 (4H, m), 1.03 (9H, s). LRMS: (m/z) 410.2 (M+H)⁺, 432.2 (M+Na)⁺.

STEP GPB: 4-[4-(2(S)-{2(R)-[(N-Benzyloxy-N-formylamino)-methyl]-hexanoylamino}-(3,3-dimethylbutyryl)-phenyl]-piperazine-1-carboxylic Acid Benzyl Ester Purification by column chromatography (SiO₂, 3:1 isohexane:ethyl acetate) afforded the title compound as a pale yellow oil (0.15 g, 58%).

¹H NMR (CDCl₃): δ/ppm 8.13 (0.6H, brs), 7.95–7.85 (0.4, m), 7.91 (2H, d, J=8.9 Hz), 7.46–7.29 (5H, m), 6.84 (2H, d, J=9.0), 6.38 (1H, d, J=9.3 Hz), 5.45 (1H, d, J=9.4 Hz), 5.17 (2H, s), 5.09–4.90 (1H, m), 4.90–4.75 (1H, m), 3.88–3.60 (6H, m), 3.42–3.31 (4H, m), 2.63–2.49 (1H, m), 1.62–1.28 (2H, m), 1.28–1.05 (4H, m), 0.90 (9H, s), 0.76 (3H, t, J=7.0 Hz). LRMS: (m/z) 671.2 (M+H)⁺, 693.4 (M+Na)⁺.

STEP GPC: 2(R)-[(N-Formyl-N-hydroxyamino)-methyl]-hexanoic Acid-(2',2'-dimethyl-1'(S)-(4-piperazin-1-yl-benzoyl)-propyl)amide The title compound was recovered as a yellow crystalline solid (0.12 g, 100%).

¹H NMR (CD₃OD): δ/ppm 8.27 (0.3H, s), 7.93 (2H, d, J=9.0 Hz), 7.85 (0.7H, s), 6.99 (2H, d, J=9.0 Hz), 5.46 (1H, s), 3.80 (1H, dd, J=14.1, 9.7 Hz), 3.61 (0.5H, dd, J=13.9, 5.7 Hz), 3.48–3.37 (4.5H, m), 3.08–2.96 (4.5H, m), 2.91–2.80 (0.5H, m), 1.57–1.32 (2H, m), 1.31–1.02 (4H, m), 0.95 (9H, s), 0.75 (3H, t, J=7.0). ¹³C NMR (CD₃OD): δ/ppm 199.6, 176.5, 176.2, 156.5, 132.3, 129.4, 115.1, 60.2, 54.0, 50.3, 4836, 46.3, 45.8, 36.3, 31.6, 30.6, 27.0, 24.0, 14.6. LRMS: (m/z) 447.2 (M+H)⁺, 469.2 (M+Na)⁺. MIC (*E. coli*): 3.1 µM MIC (*S. capitis*): 12.5 µM

EXAMPLE 27

2(R)-[(N-Formyl-N-hydroxyamino)-methyl]-hexanoic Acid-(2',2'-dimethyl-1'(S)-[4-(4-methylpiperazin-1-yl)benzoyl]-propyl)amide

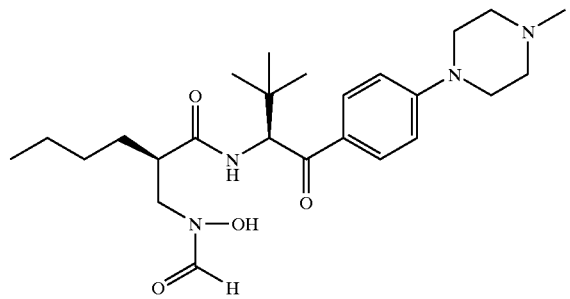

The title compound was prepared from 4-[4-(2(S)-tert-butoxycarbonylamino-3,3-dimethylbutyryl)-phenyl]-piperazine-1-carboxylic acid benzyl ester as described in Scheme 15, and using the General Protocol (GP) thereafter. The experimental details of the synthesis and relevant spectroscopic data are described below.

Scheme 15

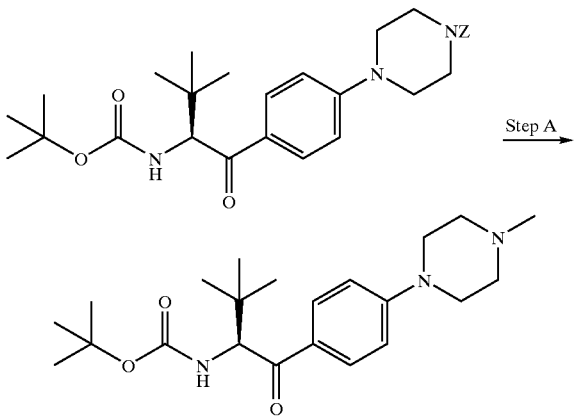

Reagents and Conditions:
A. H₂, 10% Pd-C, CH₂O (37% wt. % in H₂O), MeOH

Reagents and Conditions:
A. H$_2$, 10% Pd-C, CH$_2$O (37% wt. % in H$_2$O), MeOH

Scheme 15

STEP A: {2,2-Dimethyl-1(S)-[4-(4-methylpiperazin-1-yl)-benzoyl]-propyl}-carbamic Acid tert-butyl Ester Formaldehyde (37% wt. % solution in H$_2$O, 0.5 mL) was added to a solution of 4-[4-(2(S)-tert-Butoxycarbonylamino-3,3-dimethylbutyryl)-phenyl]-piperazine-1-carboxylic acid benzyl ester in methanol (3 mL) and ethyl acetate (1 mL). The mixture was degassed and 10% palladium on charcoal (20 mg) was added. Hydrogen gas was bubbled through the suspension for 15 minutes when a balloon containing hydrogen was introduced to the reaction. After 18 hours, the catalyst was removed by filtration and the solvents were removed in vacuo to give a yellow oil which was used without further purification (0.15 g, 100% crude).

$^1$H NMR (CDCl$_3$): δ/ppm 7.97 (2H, d, J=8.8 Hz), 7.40–7.30 (5H, m), 6.90 (2H, d, J=8.9 Hz), 5.44 (1H, brd, J=9.6 Hz), 5.09 (1H, d, J=9.7 Hz), 3.87–3.78 (4H, m), 3.50–3.05 (4H, m), 2.85 (3H, s), 1.41 (9H, s), 0.92 (9H, s). LRMS: (m/z) 390.2 (M+H)$^+$, 402.4 (M+Na)$^+$.

STEP GPA: 2(S)-Amino-3,3-dimethyl-1-[4-(4-methylpiperazin-1-yl)-phenyl]-butan-1-one The title compound was recovered as a yellow foam and used without further purification (0.14 g, 100% crude).

STEP GPB: 2(R)-[(N-Benzyloxy-N-formylamino)-methyl]-hexanoic Acid-(2',2'-dimethyl-1'(S)-[4-(4-methylpiperazin-1-yl)-benzoyl]-propyl)amide Trifluoroaectic Acid Purification by reverse phase preparative HPLC afforded the title compound as a yellow solid (0.15 g, 54%).

$^1$H NMR (CDCl$_3$): δ/ppm 8.13 (0.6H, brs), 8.01–7.91 (0.4, m), 7.95 (2H, d, J=8.7 Hz), 7.49–7.30 (5H, m), 6.90 (2H, d, J=8.7), 6.40 (1H, d, J=9.0 Hz), 5.44 (1H, d, J=9.1 Hz), 5.10–4.90 (1H, m), 4.90–4.74 (1H, m), 4.00–3.33 (8H, m), 3.17–3.79 (2H, m), 2.89 (3H, s), 2.67–2.51 (1H, m), 1.62–1.30 (2H, m), 1.30–1.02 (4H, m), 0.90 (9H, s), 0.76 (3H, t, J=7.0 Hz). LRMS: (m/z) 551.2 (M+H)$^+$, 573.4 (M+Na)$^+$.

STEP GPC: 2(R)-[(N-Formyl-N-hydroxy-amino)-methyl]-hexanoic Acid-(2',2'-dimethyl-1'(S)-[4-(4-methylpiperazin-1-yl)benzoyl]-propyl)amide Trifluoroacetic Acid Purification by reverse phase preparative HPLC afforded the title compound as a yellow solid (85 mg, 71%).

$^1$H NMR (CD$_3$OD): δ/ppm 8.27 (0.5H, s), 7.98 (2H, d, J=8.9 Hz), 7.85 (0.5H, s), 7.08 (2H, d, J=8.9 Hz), 5.46 (1H, s), 4.25–3.98 (2H, m), 3.80 (1H, dd, J=14.2, 9.0 Hz), 3.71–3.51 (4H, m), 3.42 (1H, dd, J=14.2, 4.5 Hz), 3.35–3.15 (4H, m), 3.11–2.92 (0.5H, m), 2.97 (3H, s), 2.92–2.81 (0.5H, m), 1.58–1.30 (2H, m), 1.30–1.03 (4H, m), 0.96 (3H, s), 0.95 (6H, s), 0.75 (3H, t, J=9.9 Hz) $^{13}$C NMR (CD$_3$OD): δ/ppm 199.8, 176.6, 176.3, 154.9, 132.7, 131.0, 116.1, 60.5, 54.6, 53.9, 50.3, 46.5, 45.6, 45.5, 44.0, 36.3, 31.6, 30.3, 27.9, 24.0, 14.6. LRMS: (m/z) 461.4 (M+H)$^+$. MIC (E. coli): 6.25 μM MIC (S. capitis): 6.25 μM

EXAMPLE 28

2(R)-[(N-Formyl-N-hydroxyamino)-methyl]-hexanoic Acid-(2',2'-dimethyl-1'(S)-[4-(4-pyrimidin-2-yl-piperazin-1-yl)-benzoyl]-propyl)amide

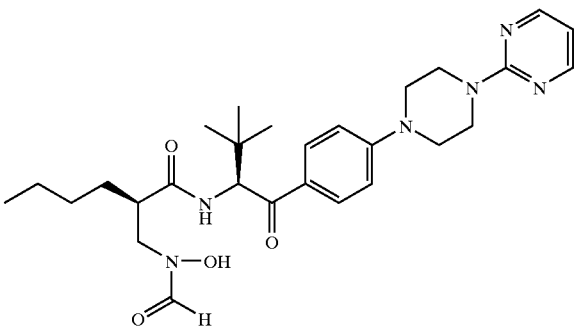

The title compound was prepared from 1-(2-pyrimidyl)-piperazine in Step A as described in Scheme 14, and using the General Protocol (GP) thereafter. The final step yielded both Example 28 and Example 29. Relevant spectroscopic data are described below.

STEP A: {2,2-Dimethyl-1(S)-[4-(4-pyrimidin-2-ylpiperazin-1-yl)-benzoyl]-propyl}-carbamic Acid tert-butyl Ester Purification by column chromatography (SiO$_2$, 5:2 isohexane:ethyl acetate) afforded the title compound as a pale brown oil (0.36 g, 82%).

$^1$H NMR (CDCl$_3$): δ/ppm 8.34 (2H, d, J=4.7), 7.95 (2H, d, J=8.8 Hz), 6.90 (2H, d, J=9.0 Hz), 6.54 (1H, t, J=4.8), 5.48 (1H, brd, J=9.4 Hz), 5.11 (1H, d, J=9.7 Hz), 4.04–3.94 (4H, m), 3.54–3.43 (4H, m), 1.42 (9H, s), 0.94 (9H, s). LRMS: (m/z) 454.4 (M+H)$^+$.

STEP GPA: 2(S)-Amino-3,3-dimethyl-1-[4-(4-pyrimidin-2-ylpiperazin-1-yl)-phenyl]-butan-1-one Dihydrochloride The title compound was recovered as pale brown solid and used without further purification (0.34 g, 100% crude).

$^1$H NMR (CDOD$_3$): δ/ppm 8.67 (2H, d, J=5.3), 8.00 (2H, d, J=9.1 Hz), 7.11–7.02 (3H, m), 4.90 (1H, s), 4.17–4.09 (4H, m), 3.82–3.72 (4H, m), 1.04 (9H, s). LRMS: (m/z) 354.4 (M+H)$^+$.

STEP GPB: 2(R)-[(N-Benzyloxy-N-formylamino)-methyl]-hexanoic Acid-(2',2'-dimethyl-1'(S)-[4-(4-pyrimidin-2-ylpiperazin-1-yl)-benzoyl)-propyl)-amide Purification by column chromatography (SiO₂, 2:1 to 3:1 ethyl acetate:iso-hexane) afforded the title compound as a yellow foam (0.24 g, 83%).

¹H NMR (CDCl₃): δ/ppm 8.13 (0.6H, brs), 7.98–7.88 (0.4, m), 7.94 (2H, d, J=8.8 Hz), 7.48–7.30 (5H, m), 6.86 (2H, d, J=9.0), 6.36 (1H, d, J=9.3 Hz), 5.46 (1H, d, J=9.4 Hz), 5.10–4.90 (1H, m), 4.90–4.75 (1H, m), 3.90–3.80 (4H, m), 3.90–3.53 (2H, m), 3.38–3.28 (4H, m), 2.62–2.50 (1H, m), 1.60–1.30 (2H, m), 1.30–1.02 (4H, m), 0.90 (9H, s), 0.76 (3H, t, J=6.9 Hz). LRMS: (m/z) 538.4 (M+H)⁺, 560.4 (M+Na)⁺, 536.4 (M–H)⁻.

STEP GPC: 2(R)-[(N-Formyl-N-hydroxyamino)-methyl]-hexanoic Acid-(2',2'-dimethyl-1'(S)-[4-(4-pyrimidin-2-yl-piperazin-1-yl)-benzoyl]-propyl) amide Purification by reverse phase preparative HPLC yielded the title compound as a pale yellow glassy solid (65 mg, 34%, 58% combined yield with Example 29).

¹H NMR (CD₃OD): δ/ppm 8.34 (2H, d, J 4.8 Hz), 8.27 (0.3H, s), 7.95 (2H, d, J 9.0 Hz), 7.86 (0.7H, s), 7.00 (2H, d, J=9.0 Hz), 6.61 (1H, t, J=4.8 Hz), 5.48 (1H, s), 3.95 (4H, t, J=5.3 Hz), 3.87–3.73 (1H, m), 3.61 (0.4H, dd, J=14.0, 5.8 Hz), 3.50 (4H, t, J=5.3 Hz), 3.41 (0.6H, dd, J=14.0, 4.6 Hz), 3.09–2.95 (0.6H, m), 2.95–2.78 (0.4H, m), 1.58–1.30 (2H, m), 1.28–1.04 (4H, m), 0.96 (9H, s), 0.74 (3H, t, J=7.0 Hz). ¹³C NMR (CD₃OD): δ/ppm 199.5, 176.5, 176.2, 163.2, 159.5, 156.4, 132.4, 129.0, 114.9, 111.9, 60.2, 56.9, 50.3, 45.8, 45.6, 44.9, 36.4, 31.6, 30.6, 28.0, 24.0, 14.6. LRMS: (m/z) 525.2 (M+H)⁺, 547.2 (M+Na)⁺. MIC (*E. coli*): 12.5 μM MIC (*S. capitis*): 1.6 μM

EXAMPLE 29

2(R)-[(N-Formyl-N-hydroxyamino)-methyl]-hexanoic Acid-(2',2'-dimethyl-1'(S)-{4-[4-(1,4,5,6-tetrahydropyrimidin-2-yl)-piperazin-1-yl]-benzoyl}-propyl)amide

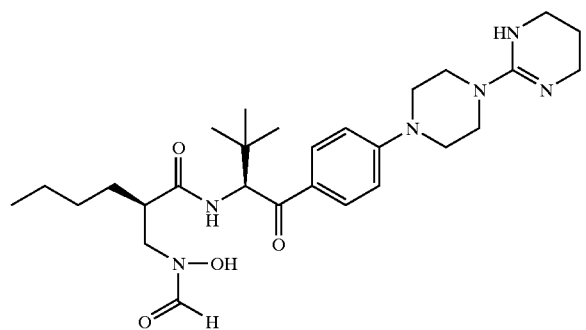

The title compound was prepared in an identical manner to Example 28 as described in Scheme 14. The final step yielded both Example 28 and Example 29. Relevant spectroscopic data are described below.

STEP GPC: 2(R)-[(N-Formyl-N-hydroxyamino)-methyl]-hexanoic Acid-(2',2'-dimethyl-1'(S)-{4-[4-(1,4,5,6-tetrahydropyrimidin-2-yl)-piperazin-1-yl]-benzoyl}-propyl)amide Purification by reverse phase preparative HPLC yielded the title compound as a colourless glassy solid (47 mg, 24%, 58% combined yield with Example 28).

¹H NMR (CD₃OD): δ/ppm 8.27 (0.3H, s), 7.95 (2H, d, J=8.9 Hz), 7.86 (0.7H, s), 6.98 (2H, d, J=8.9 Hz), 5.46 (1H, s), 3.77 (1H, dd, J=14.1, 4.9 Hz), 3.69–3.50 (8.3H, m), 3.47–3.38 (0.7H, m), 3.42 (4H, t, J=5.9 Hz), 3.10–2.95 (0.7H, m), 2.95–2.80 (0.3H, m), 1.97 (2H, tt, J=5.9, 5.9 Hz), 1.58–1.30 (2H, m), 1.30–1.02 (4H, m). 0.97 (3H, s), 0.95 (6H, s), 0.74 (3H, t, J=7.0 Hz). ¹³C NMR (CD₃OD): δ/ppm 199.8, 199.6, 176.5, 176.2, 159.8, 155.5, 155.3, 132.4, 129.5, 114.8, 60.3, 53.9, 50.3, 47.4, 46.1, 45.7, 45.6, 40.7, 36.3, 31.6, 30.6, 28.0, 24.0, 21.7, 14.6. LRMS: (m/z). 529.2 (M+H)⁺, 527.4 (M–H)⁻. MIC (*E. coli*): 50 μM MIC (*S. capitis*): 6.25 μM

EXAMPLE 30

2(R)-[(N-Formyl-N-hydroxyamino)-methyl]-hexanoic Acid-(1'(S)-(4-dipropylaminobenzoyl)-2',2'-dimethylpropyl)amide

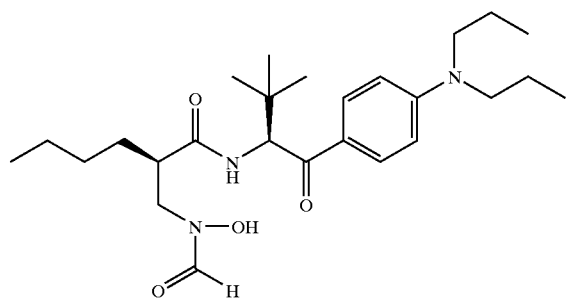

The title compound was prepared utilising diallyl amine in Step A as described in Scheme 14, and using the General Protocol (GP) thereafter. The final step yielded both Example 30 and Example 31. Relevant spectroscopic data are described below.

STEP A: [1(S)-(4-Diallylaminobenzoyl)-2,2-dimethylpropyl]-carbamic Acid tert-butyl Ester Purification by column chromatography (SiO₂, 19:1 iso-hexane:ethyl acetate) afforded the title compound as a thick yellow oil (5.18 g, 52% (81% based on recovered SM)).

¹H NMR (CDCl₃): δ/ppm 7.89 (2H, d, J=8.6 Hz), 6.66 (2H, d, J=8.7 Hz), 5.85 (2H, ddt, J=17.1, 10.3, 4.7 Hz), 5.47 (1H, brd, J=9.5 Hz), 5.26–5.11 (4H, m), 5.09 (1H, d, J=9.6 Hz), 4.04–3.94 (4H, m), 1.42 (9H, s), 0.95 (9H, s). LRMS: (m/z) 387.2 (M+H)⁺.

STEP GPA: 2(S)Amino-1-(4-diallylamino-phenyl)-3,3-dimethylbutan-1-one Hydrochloride The title compound was recovered as yellow solid and used without further purification (3.7 g, 100% crude).

¹H NMR (CDOD₃): δ/ppm 7.91 (2H, d, J=8.6 Hz), 6.85 (2H, d, J=8.7 Hz), 5.90 (2H, ddt, J=17.1, 10.3, 4.7 Hz), 5.26–5.17 (3H, m), 5.16–5.12 (1H, m), 4.84 (1H, s), 4.13–3.05 (4H, m), 1.05 (9H, s). LRMS: (m/z) 287.2 (M+H)⁺.

STEP GPB: 2(R)-[(N-Benzyloxy-N-formylamino)-methyl]-hexanoic Acid-(1'(S)-(4-diallylaminobenzoyl)-2',2'-dimethylpropyl)-amide Purification by column chromatography (SiO₂, 3:1 iso-hexane:ethyl acetate) afforded the title compound as a yellow oil (5.64 g, 90%).

¹H NMR (CDCl₃): δ/ppm 8.13 (0.6H, brs), 7.95–7.83 (0.4, m), 7.88 (2H, d, J=9.0 Hz), 7.48–7.31 (5H, m), 6.65

(2H, d, J=9.1), 6.40 (1H, d, J=9.3 Hz), 5.84 (2H, ddt, J=17.0, 10.4, 4.7 Hz), 5.44 (1H, d, J=9.4 Hz), 5.24–5.17 (3H, m), 5.16–5.10 (1H, m), 5.08–4.90 (1H, m), 4.90–4.74 (1H, m), 4.04–3.94 (4H, m), 3.89–3.58 (2H, m), 2.62–2.48 (1H, m), 1.60–1.30 (2H, m), 1.30–1.05 (4H, m), 0.91 (9H, s), 0.76 (3H, t, J=6.9 Hz). LRMS: (m/z) 548.4 (M+H)$^+$, 570.4 (M+Na)$^+$.

STEP GPC: 2(R)-[(N-Formyl-N-hydroxyamino)-methyl]-hexanoic Acid-(1'(S)-(4-dipropylaminobenzoyl)-2',2'-dimethylpropyl)amide Purification by reverse phase preparative HPLC yielded the title compound as a colourless foam (20 mg, 22%, 69% combined yield with Example 31).

$^1$H NMR (CD$_3$OD): δ/ppm 8.27 (0.3H, s), 7.92–7.80 (2.7H, m), 6.68 (2H, d, J=9.1 Hz), 5.45 (1H, s), 3.88–3.75 (1H, m), 3.61 (0.3H, dd, J=14.4, 5.8 Hz), 3.48–3.30 (4.7H, m), 3.08–2.90 (0.7H, m), 3.90–2.78 (0.3H, m), 1.64 (4H, qt, J=7.5, 7.5 Hz), 1.55–1.27 (2H, m), 1.27–1.06 (4H, m), 1.05–0.76 (15H, m), 0.74 (3H, t, J=6.9 Hz). $^{13}$C NMR (CD$_3$OD): δ/ppm 198.8, 176.4, 176.1, 159.8, 154.2, 132.8, 125.8, 112.1, 59.9, 54.0, 50.3, 45.9, 45.7, 36.4, 31.6, 31.2, 30.6, 27.6, 24.0, 21.8, 14.5, 11.9. LRMS: (m/z) 462.2 (M+H)$^+$, 460.4 (M–H)$^-$. MIC (E. coli): 100 μM MIC (S. capitis): 3.1 μM

EXAMPLE 31

2(R)-[(N-Formyl-N-hydroxyamino)-methyl]-hexanoic Acid-(2',2'-dimethyl-1'(S)-(4-propylaminobenzoyl)-propyl)amide

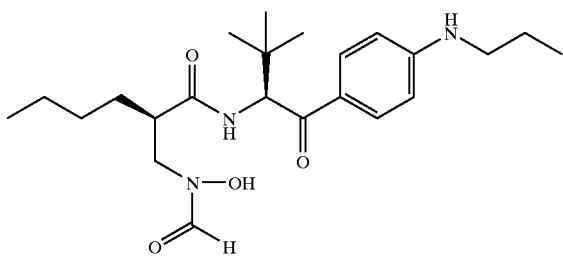

The title compound was prepared in an identical manner to Example 30 as described in Scheme 14. The final step yielded both Example 30 and Example 31. Relevant spectroscopic data are described below.

STEP GPC: 2(R)-[(N-Formyl-N-hydroxyamino)-methyl]-hexanoic Acid-(2',2'-dimethyl-1'(S)-(4-propylaminobenzoyl)-propyl)amide Purification by reverse phase preparative HPLC yielded the title compound as a white powder (45 mg, 49%; 69% combined yield with Example 30).

$^1$H NMR (CD$_3$OD): δ/ppm 8.27 (0.4H, s), 7.89–7.78 (2.6H, m), 6.60 (2H, d, J=8.9 Hz), 5.44 (1H, s), 3.86–3.72 (1H, m), 3.61 (0.4H, dd, J=14.0, 5.8 Hz), 3.40 (0.6H, dd, J=14.2, 4.6 Hz), 3.13 (2H, t, J=7.1 Hz), 3.08–2.90 (0.6H, m), 3.90–2.76 (0.4H, m), 1.65 (2H, qt, J=7.3,7.3 Hz), 1.55–1.30 (2H, m), 1.29–1.06 (4H, m), 1.04–0.89 (12H, m), 0.75 (3H, t, J=7.0). $^{13}$C NMR (CD$_3$OD): δ/ppm 199.1, 198.9, 176.4, 176.1, 159.8, 155.9, 132.9, 126.7, 112.5, 59.8, 53.9, 50.3, 46.1, 45.9, 45.7, 36.4, 31.6, 30.6, 28.0, 24.1, 24.0, 14.5, 12.3. LRMS: (m/z) 420.2 (M+H)$^+$, 442.2 (M+Na)$^+$, 418.4 (M–H)$^-$. MIC (E. coli): 12.5 μM MIC (S. capitis): 3.1 μM

EXAMPLE 32

2(R)-[(N-Formyl-N-hydroxyamino)-methyl]-hexanoic Acid-(1'(S)-acetyl-2',2'-dimethylpropyl)amide

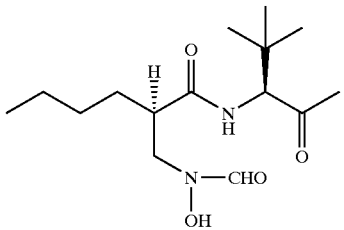

STEP A: 2(S)-tert-Butoxycarbonylamino-3,3-dimethyl-butyric Acid

To a suspension of L-tert-leucine (26.1 g, 0.2 mol) in methanol (150 mL) was added triethylamine (56 mL, 0.4 mol) and the mixture cooled to 0° C. To the mixture was added slowly a solution: of di-tert-butyldicarbamate (48 g, 0.22 mol) in methanol (40 mL) such that an internal temperature of between 0 and 5° C. was maintained. The reaction was allowed to stir overnight and the solvents were removed in vacuo. The residue was dissolved in ethyl acetate (200 mL) and washed with 10% w/v aqueous citric acid solution (3×100 mL). The organic layer was dried over MgSO$_4$, filtered and the solvents removed in vacuo to give the title product as a pale yellow oil (48.9 g, >100%, residual solvent).

$^1$H NMR (CDCl$_3$): δ/ppm 9.20 (1H, bs), 5.10 (1H, m), 4.15 (1H, m), 1.45 (9H, s), 1.00 (9H, s).

STEP B: [1(S)-(Methoxy-methyl-carbamoyl)-2,2-dimethylpropyl]-carbamic Acid-tert-butyl Ester To a solution of 2(S)-tert-butoxycarbonylamino-3,3-dimethyl-butyric acid (30 g, 0.13 mol) in dichloromethane (400 mL) was added portionwise 1,1'-carbonyldiimidazole (63.3 g, 0.39 mol). After addition was complete the reaction was allowed to stir for 15 minutes before N-methoxy-N-methylamine hydrochloride (38 g, 0.39 mol) was added and the reaction allowed to stir overnight. The solvents were removed in vacuo and the residue partitioned between ethyl acetate (250 mL) and 1M HCl (150 mL). The organic phase was washed with 1M HCl solution (2×100 mL), saturated sodium bicarbonate solution (2×100 mL) and brine (100 mL). The organic phase was dried over MgSO$_4$, filtered and the solvents removed in vacuo to give a crude yellow oil. Purification by column chromatography (SiO$_2$, 30% ethyl acetate in hexanes) afforded the title product as a pale yellow oil (26.5 g, 74%).

$^1$H NMR (CDCl$_3$): δ/ppm 5.20 (1H, bd, J=9.5 Hz), 4.65 (1H, d, J=10.4 Hz), 3.77 (3H, s), 3.21 (3H, s), 1.43 (9H, s), 0.97 (9H, s). LRMS: (m/z) 297 (M+Na)$^+$.

STEP C: (1(S)-Acetyl-2,2-dimethylpropyl)carbamic Acid-tert-butyl Ester

[1(S)-(Methoxy-methyl-carbamoyl)-2,2-dimethylpropyl]-carbamic acid-tert-butyl ester (2.0 g, 7.3 mmol) was dissolved in, freshly distilled THF under an argon atmosphere. The solution was cooled to −78° C. whereupon MeLi (15.6 mL, 1.4 M in diethyl ether, 21.9 mmol, 3 eqv) was added dropwise maintaining an internal temperature <−70° C. The reaction was stirred at −70° C. for 30 minutes before warming to −30° C. for a further 30 minutes. After this time TLC analysis indicated the complete consumption of starting material. Saturated aqueous ammonium chloride solution (10 mL) was added and the reaction allowed to warm to room temperature. The aqueous phase was extracted with ethyl acetate (3×30 mL). The organic phases were washed with water (3×50 mL) and brine (50 mL), dried over MgSO$_4$, filtered and the solvents removed in vacuo to give a crude yellow oil. Purification by column chromatography (SiO$_2$, 20% ethyl acetate in hexanes) afforded the title compound as a colourless oil (1.355 g, 84%).

$^1$H NMR (CDCl$_3$): δ/ppm 5.13 (1H, m), 4.16 (1H, bd, J=10.0 Hz), 2.25 (3H, s), 1.43 (9H, s), 0.98 (9H, s). LRMS: (m/z) 252 (M+Na)$^+$.

STEP D: 3(S)-Amino-4,4-dimethyl-pentan-2-one

To a solution of (1(S)-acetyl-2,2-dimethylpropyl) carbamic acid-tert-butyl ester (700 mg, 2.55 mmol) in dichloromethane (10 mL) at 0° C. was added trifluoroacetic acid (5 mL). The reaction was left at <5° C. for 16 hours before the solvents were removed in vacuo to give a bright yellow oil. The residue was dissolved in methanol (30 mL) and was treated portionwise with Dowex 1X8-400 basic resin until pH 9. Filtration and removal of the solvents in vacuo gave the title compound as a pale yellow oil (~1.0 g, >100%, residual water). The material was used without further purification.

$^1$H NMR (CDCl$_3$): δ/ppm 3.28 (1H, s), 2.21 (3H, s), 1.50 (2H, bs), 0.98 (9H, s).

STEP E: 2(R)-(N-Benzyloxyaminomethyl)-hexanoic Acid-(1'(S)-acetyl-2',2'-dimethylpropyl)amide To a suspension of 2(R)-(N-benzyloxyamino-methyl)-hexanoic acid (879 mg, 3.5 mmol, 1.1 eqv) in DMF (10 mL) at 0° C. was added EDC (730 mg, 1.2 eqv) and 1-hydroxybenzotriazole (43 mg, 10 mol%). The mixture was allowed to stir at 0° C. for 45 minutes before a solution of 3(S)-amino-4,4-dimethyl-pentan-2-one (409 mg, 1 eqv) in DMF (5 mL) was added. The reaction was allowed to warm to room temperature and stirred overnight. The solvents were removed in vacuo and the residue dissolved in ethyl acetate (50 mL) and 10% w/v aqueous citric acid (50 mL). The aqueous phase was extracted with ethyl acetate (3×50 mL) and the combined organic layers washed with saturated sodium hydrogen carbonate (100 mL) and brine (2×100 mL). The organic phases were dried over MgSO$_4$, filtered and the solvents removed in vacuo to give a crude yellow oil. Purification by column chromatography (SiO$_2$, 25% ethyl acetate in hexanes) gave the title compound as a clear oil (412 mg, 36%).

$^1$H NMR (CDCl$_3$): δ/ppm 7.35 (5H, m), 6.73 (1H, bd, J=8.7 Hz), 5.68 (1H, bs), 4.73 (2H, s), 4.54 (1H, d, J=8.7 Hz), 3.06 (2H, m), 2.50 (1H, m), 2.27 (3H, s), 1.70–1.20 (6H, m), 0.98 (9H, s), 0.87 (3H, t, J=7.0 Hz). LRMS: (m/z) 363 (M+H)$^+$.

STEP F: 2(R)-[N-Benzyloxy-N-formylamino)-methyl]-hexanoic Acid-(1'(S)-acetyl-2',2'-dimethylpropyl)amide To a solution of 2(R)-(N-benzyloxyamino-methyl)-hexanoic acid-(1'(S)-acetyl-2',2'-dimethylpropyl)amide (400 mg, 1.1 mmol) in dichloromethane (10 mL) at 0° C. was added formylacetic anhydride (0.25 mL, 2.76 mmol, 2.5 eqv) and the reaction allowed to stir at room temperature. After 2 hours TLC analysis indicated complete consumption of the starting material. The solvents were removed in vacuo and the residue azeotroped with toluene (3×30 mL). The product was placed under high vacuum to give the title compound as a clear sticky oil (443 mg, >100%, residual solvent).

$^1$H NMR (CDCl$_3$): δ/ppm 8.15 (0.7H, bs), 7.90 (0.3H, bs), 7.38 (5H, bs), 6.06 (1H, bd, J=8.2 Hz), 5.00–4.75 (2H, m), 4.43 (1H, bd, J=8.3 Hz), 3.72 (2H, m), 2.53 (1H, m), 2.24 (3H, s), 1.65–1.40 (2H, m), 1.35–1.10 (4H, m), 0.94 (9H, s), 0.86 (3H, t, J=6.7 Hz). LRMS: (m/z) 389 (M−H)$^−$, 391 (M+H)$^+$.

STEP G: 2(R)-[N-Formyl-N-hydroxyamino)-methyl]-hexanoic Acid-(1'(S)-acetyl-2',2'-dimethylpropyl)amide To a solution of 2(R)-[N-benzyloxy-N-formylamino)-methyl]-hexanoic acid-(1'(S)-acetyl-2',2'-dimethylpropyl) amide (200 mg, 0.55 mmol) in methanol (10 mL) under argon was added a slurry of 10% Pd/C (27 mg) in ethyl acetate (5 mL). Hydrogen gas was bubbled through the reaction for 15 minutes after which time the reaction was allowed to stir under a hydrogen atmosphere of 1 bar for two hours. After this time TLC analysis indicated the complete consumption of starting material. The reaction was flushed with argon and filtered through Celite. The solvents were removed in vacuo to afford the title compound as a pale orange solid (148 mg, 96%).

$^1$H NMR (CDCl$_3$): δ/ppm 8.38 (0.3H, s), 7.81 (0.7H, s), 6.40 (0.3H, bd, J=6.9 Hz), 6.25 (0.7H, bd, J=8.2 Hz), 4.52 (1H, m), 4.00 (0.3H, dd, J=14.7, 7.1 Hz), 3.82 (0.7H, dd, J=14.2, 10.0 Hz), 3.62 (0.3H, dd, J=14.5, 2.8 Hz), 3.47 (0.7H, dd, J=14.2, 3.8 Hz), 2.79 (0.7H, m), 2.65 (0.3H, m), 2.30 (0.9H, s), 2.27 (2.1H, s), 1.60 (1H, m), 1.50–1.20 (5H, m), 1.01 (2.7H, s), 0.96 (6.3H, s), 0.88 (3H, t, J=6.6 Hz). $^{13}$C NMR (CD$_3$OD): δ/ppm 177.0, 176.7, 67.9, 53.9, 45.5, 45.3, 35.1, 31.5, 31.2, 30.7, 27.8, 24.1, 14.6. LRMS: (m/z) 299 (M−H)$^−$, 301 (M+H)$^+$, 323 (M+Na)$^+$.

To a suspension of 2(R)-(N-benzyloxyamino-methyl)-hexanoic acid (1.430 mg, 5.17 mmol, 1.1 eqv) in DMF (20 mL) at 0° C. was added EDC (1.190 g, 5.64 mmol 1.2 eqv) and 1-hydroxybenzotriazole (84 mg, 10 mol%). The mixture was allowed to stir at 0° C. for 45 minutes before a solution of 2(S)-amino-N-methoxy-3,3,N-trimethyl-butyramide (900 mg, 4.7 mmol, 1 eqv) in DMF (5 mL) was added. The reaction was allowed to warm to room temperature and stirred overnight. The solvents were removed in vacuo and the residue dissolved in ethyl acetate (75 mL) and 10% w/v aqueous citric acid (50 mL). The aqueous phase was extracted with ethyl acetate (3×75 mL) and the combined organic layers washed with saturated sodium hydrogen carbonate solution (100 mL) and brine (2×100 mL). The organic phases were dried over MgSO$_4$, filtered and the solvents removed in vacuo to give a crude yellow oil. Purification by column chromatography (SiO$_2$, 25% ethyl acetate in hexanes) gave the title compound as a clear oil (1.43 g, 68%).

$^1$H NMR (CDCl$_3$): δ/ppm 7.35 (5H, m), 6.73 (1H, bd, J=10.0 Hz), 5.70 (1H, bs), 5.05 (1H, d, J=10.0 Hz), 4.74 (2H, s), 3.78 (3H, s), 3.20 (3H, s), 3.07 (2H, m), 2.50 (1H, m), 1.65 (1H, m), 1.45 (1H, m), 1.25 (4H, m), 0.98 (9H, s), 0.86 (3H, t, J=7.0 Hz). LRMS: (m/z) 408 (M+H)$^+$.

STEP C: 2(R)-[(N-Benzyloxyamino)-methyl]-hexanoic Acid-(1'(S)-benzoyl-2',2'-dimethylpropyl) amide To a solution of 2(R)-[(N-benzyloxyamino)-methyl]-hexanoic acid-[1'(S)-(methoxy-methyl-carbamoyl)-2',2'- dimethylpropyl]amide (416 mg, 1.05 mmol) in freshly distilled THF (10 mL) under argon at −78° C. was added dropwise PhLi (3.5 mL, 1.8M in cyclohexane, 6.3 mmol, 6 eqv) such that an internal temperature of <−70° C. was maintained. The reaction was allowed to stir at −70° C. for three hours after which time TLC analysis appeared to indicate the complete consumption of starting material. Saturated aqueous ammonium chloride solution (10 mL) was added and the solution allowed to warm to room temperature. The aqueous phase was extracted with ethyl acetate (3×50 mL), and the organic phases combined and washed with water (3×50 mL) and brine (50 mL). The organic phase was dried over MgSO$_4$, filtered and the solvents removed in vacuo to give a crude yellow oil. Purification by column chromatography (SiO$_2$/25% ethyl acetate in hexanes) gave the title product as a colourless oil (143 mg, 32%, Rf=0.3) and the recovered starting material 2(R)-[(N-Benzyloxyamino)-methyl]-hexanoic acid-[1'(S)-(methoxy-methyl-carbamoyl)-2',2'-dimethylpropyl]amide (209 mg, Rf=0.1).

$^1$H NMR (CDCl$_3$): δ/ppm 8.02 (2H, m), 7.62–7.40 (2H, m), 7.40–7.25 (6H, m), 6.97 (1H, bd, J=9.4 Hz), 5.60 (1H, d, J=9.4 Hz), 4.75 (2H, s), 3.10 (2H, m), 2.53 (1H, m), 1.65–1.30 (2H, m), 1.30–1.10 (4H, m), 0.94 (9H, s), 0.85 (3H, m).

STEP D: 2(R)-[(N-Benzyloxy-N-formylamino)-methyl]-hexanoic acid-(1'(S)-benzoyl-2',2'-dimethylpropyl)amide To a solution of 2(R)-[(N-benzyloxyamino)-methyl]-hexanoic acid-(1'(S)-benzoyl-2',2'-dimethylpropyl)amide (195 mg, 0.46 mmol) in dichloromethane (50 mL) at 0° C. was added formylacetic anhydride (0.1 mL, 1.15 mmol, 2.5 eqv) and the reaction allowed to stir at room temperature. After 1 hour TLC analysis indicated complete consumption of the starting material. The solvents were removed in vacuo and the residue azeotroped with toluene (3×30 mL). The product was placed under high vacuum for several hours to give the title compound as a clear sticky oil (208 mg, 100%).

$^1$H NMR (CDCl$_3$): δ/ppm 8.15 (0.5H, bs), 8.00 (2.5H, m), 7.65–7.30 (8H, m), 6.33 (1H, bd, J=9.0 Hz), 5.51 (1H, d, J=9.0 Hz), 5.00 (1H, m), 4.80 (1H, m), 3.75 (2H, bm), 2.58 (1H, m), 1.70–1.00 (6H, m), 0.89 (9H, s), 0.77 (3H, t, J=6.7 Hz). LRMS: (m/z) 451 (M−H)$^-$, 453 (M+H)$^+$.

STEP E: 2(R)-[(N-Formyl-N-hydroxyamino)-methyl]-hexanoic Acid-(1'(S)-benzoyl-2',2'-dimethylpropyl)amide To a solution of 2(R)-[(N-benzyloxy-N-formylamino)-methyl]-hexanoic acid-(1'(S)-benzoyl-2',2'-dimethylpropyl)amide (192 mg, 0.43 mmol) in methanol (5 mL) was added a slurry of 10% Pd/C (20 mg) in ethyl acetate (2 mL). Hydrogen gas was bubbled through the reaction for 15 minutes after which time the reaction was allowed to stir under a hydrogen atmosphere of 1 bar for. After four hours reaction time TLC analysis indicated the complete consumption of starting material. The reaction was flushed with argon and filtered through glass fibre. The solvents were removed in vacuo to afford the title compound as a white crystalline solid (135 mg, 88%). The product was purified by preparative HPLC giving 75 mg (49%) of a white crystalline solid.

$^1$H NMR (CDCl$_3$): δ/ppm 9.18 (1H, bs), 8.40 (0.3H, s), 8.00 (2H, bd, J=7.1 Hz), 7.86 (0.7H, s), 7.60 (1H, m), 7.48 (2H, m), 6.84 (0.3H, bd, J=9.2 Hz), 6.70 (0.7H, bd, J=9.3 Hz), 5.55 (1H, m), 4.05 (0.3H, dd, J=14.6, 7.2 Hz), 3.87 (0.7H, dd, J=14.1, 9.7 Hz), 3.64 (0.3H, dd, J=14.6, 3.3 Hz), 3.47 (0.7H, dd, J=14.0, 4.0 Hz), 2.85 (0.7H, m), 2.71 (0.3H, m), 1.55 (1H, m), 1.40 (1H, m), 1.30–1.10 (4H, m), 0.94 (3H, s), 0.90 (6H, s), 0.78 (3H, t, J=6.3 Hz). $^{13}$C NMR (CDCl$_3$): δ/ppm 176.1, 172.9, 137.6, 133.9, 133.6, 128.9, 128.8, 128.6, 59.4, 59.1, 51.8, 47.7, 46.2, 44.7, 35.7, 35.4, 30.0, 29.8, 29.2, 29.1, 27.0, 22.5, 13.7. LRMS: (m/z) 361 (M−H)$^-$, 363 (M+H)$^+$.

Biological Example

Minimal inhibitory concentrations (MIC) of inhibitors against *E. coli* strain DH5α (Genotype; F-φ80d/acZΔM 15Δ(lacZYA-argF)U 169 deoR recA1 endA1 hsdR17(r$_k^-$, m$_k^+$)phoAsupE44λ$^-$thi-1 gyrA96 re/A1) obtained from GibcoBRL Life Technologies, or *Staphylococcus capitis* (American Type Culture Collection number 35661) were determined as follows. Stock solutions of each test compound were prepared by dissolution of the compound in dimethylsulfoxide at 10 mM. For the determination of the minimal inhibitory concentration, two fold serial dilutions were prepared in 2×YT broth (typtone 16 g/l, yeast extract 10 g/l, sodium chloride 5 g/l obtained from BIO 101 Inc, 1070 Joshua Way, Vista, Calif. 92083, USA) to yield 0.05 ml compound-containing medium per well. Inocula were prepared from cultures grown overnight in 2×YT broth at 37° C. Cell densities were adjusted to absorbance at 660 nm (a$_{660}$)=0.1; the optical density-standardised preparations were diluted 1:1000 in 2×YT broth; and each well inoculated with 0.05 ml of the diluted bacteria. Microtiter plates were incubated at 37° C. for 18 hours in a humidified incubator. The MIC (μM) was recorded as the lowest drug concentration that inhibited visible growth.

What is claimed is:

1. A method for the treatment of bacterial or protozoal infections in humans and non-human mammals, which comprises administering to a subject suffering such infection an antibacterially or antiprotozoally effective dose of a compound of formula (I) or a pharmaceutically or veterinarily acceptable salt, hydrate or solvate thereof:

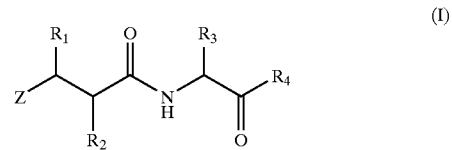

(I)

wherein:

Z represents a radical of formula —N(OH)CH(=O) of formula —C(=O)NH(OH);

R$_1$ represents hydrogen, methyl or trifluoromethyl, or, except when Z is a radical of formula —N(OH)CH (=O), a hydroxy or amino group;

R$_2$ represents a group R$_{10}$—(X)$_n$—(ALK)$_m$— wherein R$_{10}$ represents hydrogen, or a C$_{1-6}$ alkyl, C$_2$–C$_6$ alkenyl, C$_2$–C$_6$ alkynyl, cycloalkyl, aryl, or heterocyclyl group, any of which may be unsubstituted or substituted by (C$_1$–C$_6$)alkyl, (C$_1$–C$_6$)alkoxy, hydroxy, mercapto, (C$_1$–C$_6$)alkylthio, amino, halo (including fluoro, chloro, bromo and iodo), trifluoromethyl, cyano, nitro, oxo, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a (C$_1$–C$_6$)alkyl group and ALK represents a straight or branched divalent C$_1$–C$_6$ alkylene, C$_2$–C$_6$ alkenylene, or C$_2$–C$_6$ alkynylene radical, and may be interrupted by one or more non-adjacent —NH—, —O— or —S— linkages, X represents —NH—, —O— or —S—, and
m and n are independently 0 or 1;
$R_3$ represents the side chain of a natural or non-natural alpha amino acid; and
$R_4$ represents a radical $R_5$—(ALK)$_p$— wherein ALK is as defined in relation to $R_2$, p is 0 or 1, and $R_5$ represents hydrogen, or a $C_{1-6}$ alkyl, $C_2$–$C_6$ alkenyl, $C_2$–$C_6$ alkynyl, cycloalkyl, aryl, or heterocyclyl group any of which
  (i) may be substituted by a group selected from ($C_1$–$C_6$) alkyl, phenyl, benzyl, ($C_1$–$C_6$)alkoxy, phenoxy, hydroxy, mercapto, ($C_1$–$C_6$)alkylthio, amino, halo, trifluoromethyl, cyano, nitro, oxo, —COOH, —SO$_2$H, —CONH$_2$, —SO$_2$NH$_2$, —COR$^A$, —SOR$^A$, —SO$_2$R$^A$, —SO$_2$R$^A$, —COOR$^A$, —CONHR$^A$, —SO$_2$NHR$^A$, —NHCOR$^A$, —NHSO$_2$R$^A$, and —NHR$^A$, wherein R$^A$ is
    ($C_1$–$C_6$)alkyl, cycloalkyl, phenyl, 2-, 3- or 4-pyridyl, N- or 2-, 3- or 4-piperidyl, N- or 2- or 3-piperazyl group; or
  (ii) may be substituted by —NR$^A$R$^B$, —CONR$^A$R$^B$ or —SO$_2$NR$^A$R$^B$, wherein R$^A$ and R$^B$ are independently ($C_1$–$C_6$)alkyl, cycloalkyl, phenyl, 2-, 3- or 4-pyridyl, N- or 2-, 3- or 4-piperidyl, N- or 2- or 3-piperazyl group,
or when taken together with the N atom to which they are attached R$^A$ and R$^B$ form a 5 to 7 membered aromatic or non-aromatic ring, which ring (a) may contain additional heteroatoms selected from N, O and S, and in which any S atom may be oxidised as a sulphonyl or sulphoxide, and (b) may be substituted on a ring carbon or heteroatom by one or more of the substituents listed under (i) above.

2. The method of claim 1 wherein $R_1$ is hydrogen.

3. The method of claim 1 wherein $R_2$ is:
optionally substituted $C_{1-8}$ alkyl, $C_3$–$C_6$ alkenyl, $C_3$–$C_6$ alkynyl or cycloalkyl;
phenyl($C_1$–$C_6$ alkyl)-, phenyl($C_3$–$C_6$ alkenyl)- or phenyl ($C_3$–$C_6$ alkynyl)-optionally substituted in the phenyl ring;
cycloalkyl($C_1$–$C_6$ alkyl)-, cycloalkyl($C_3$–$C_6$ alkenyl)- or cycloalkyl($C_3$–$C_6$ alkynyl)-optionally substituted in the cycloalkyl ring;
heterocyclyl($C_1$–$C_6$ alkyl)-, heterocyclyl($C_3$–$C_6$ alkenyl)- or heterocyclyl($C_3$–$C_6$ alkynyl)-optionally substituted in the heterocyclyl ring; or
CH$_3$(CH$_2$)$_p$O(CH$_2$)$_q$— or CH$_3$(CH$_2$)$_p$S(CH$_2$)$_q$—, wherein p is 0, 1, 2 or 3 and q is 1, 2 or 3.

4. The method of claim 1 wherein $R_2$ is methyl, ethyl, n- or iso-propyl, n- and iso-butyl, n-pentyl, iso-pentyl, 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, or 4-methoxybenzyl.

5. The method of claim 1 wherein $R_2$ is n-propyl, n-butyl, n-pentyl, or cyclopentylmethyl.

6. The method of claim 1 wherein $R_3$ is:
the characterising group of a natural a amino acid or 4-methoxyphenylmethyl, in which any functional group may be protected, any amino group may be acylated and any carboxyl group present may be amidated; or a group —(Alk)$_n$R$_9$ where Alk is a ($C_1$–$C_6$)alkylene or ($C_2$–$C_6$)alkenylene group optionally interrupted by one or more —O—, or —S— atoms or —N(R$_{12}$)— groups where R$_{12}$ is a hydrogen atom or a ($C_1$–$C_6$)alkyl group, n is 0 or 1, and R$_9$ is hydrogen or an optionally substituted phenyl, aryl, heterocyclyl, cycloalkyl or cycloalkenyl group or (only when n is 1) R$_9$ may additionally be hydroxy, mercapto, ($C_1$–$C_6$)alkylthio, amino, halo, trifluoromethyl, nitro, —COOH, —CONH$_2$, —COOR$^A$, —NHCOR$^A$, —CONHR$^A$, —NHR$^A$, NR$^A$R$^B$, or —CONR$^A$R$^B$ wherein R$^A$ and R$^B$ are independently a ($C_1$–$C_6$)alkyl group; or a benzyl group substituted in the phenyl ring by a group of formula —OCH$_2$COR$_8$ where R$_8$ is hydroxyl, amino, ($C_1$–$C_6$)alkoxy, phenyl($C_1$–$C_6$)alkoxy, ($C_1$–$C_6$)alkylamino, di(($C_1$–$C_6$)alkyl)amino, phenyl($C_1$–$C_6$)alkylamino; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_{1-6}$) alkanoyl, trifluoromethyl ($C_1$–$C_6$)alkyl, hydroxy, formyl, amino, ($C_1$–$C_6$)alkylamino, di-($C_1$–$C_6$) alkylamino, mercapto, ($C_1$–$C_6$)alkylthio, hydroxy ($C_1$–$C_6$)alkyl, mercapto($C_1$–$C_6$)alkyl or ($C_1$–$C_6$) alkylphenylmethyl; or a group —CR$_a$R$_b$R$_c$ in which:
each of R$_a$R$_b$ and R$_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or
R$_c$ is hydrogen and R$_a$ and R$_b$ are independently phenyl or heteroaryl such as pyridyl; or
R$_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and R$_a$ and R$_b$ together with the carbon atom to which they are attached form a 3 to 8 membered cycloalkyl or a 5- to 6-membered heterocyclic ring; or
R$_a$R$_b$ and R$_c$ together with the carbon atom to which they are attached form a tricyclic ring (for example adamantyl); or
R$_a$ and R$_b$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, ($C_1$–$C_4$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$)alkyl, —SO ($C_1$–$C_6$)alkyl, —SO$_2$($C_1$–$C_6$)alkyl, —S($C_2$–$C_6$) alkenyl, —SO($C_2$–$C_6$)alkenyl, —SO$_2$($C_2$–$C_6$) alkenyl or a group —Q—W wherein Q represents a bond or —O—, —S—, —SO— or —SO$_2$— and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH($C_1$–$C_6$) alkyl, —CONH($C_{1-6}$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$ ($C_1$–$C_6$)alkyl, —NO$_2$, —NH$_2$, —NH($C_1$–$C_6$)alkyl, —N((C₁–C₆)alkyl)₂, —NHCO(C₁–C₆)alkyl, (C₁–C₆)alkyl, (C₂–C₆)alkenyl, (C₂–C₆)alkynyl, (C₃–C₈)cycloalkyl, (C₄–C₈)cycloalkenyl, phenyl or benzyl.

7. The method of claim 1 wherein R₃ is methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxethyl, 2-carboxyethyl, 2-methylcarbamoylethyl, 2-carbamoylethyl, or 4-aminobutyl.

8. The method of claim 1 wherein R₃ is tert-butyl.

9. The method of claim 1 wherein R₄ is:

optionally substituted C₁–C₈ alkyl, C₂–C₆ alkenyl, C₂–C₆ alkynyl or cycloalkyl;

optionally substituted phenyl, biphenyl or naphthyl;

optionally substituted piperidinyl, cyclohexyl, cyclopentyl, oxazolyl, thiazepinyl, pyridinyl, pyrrolidinyl, pyrimidinyl, morpholinyl, piperazinyl, indolyl, thienyl, furanyl, pyrrolyl, imidazolyl, benzofuranyl, benzothienyl, benzimidazolyl, thiazolyl, benzothiazolyl, pyrazolyl, isoxazolyl, isothiazolyl, triazolyl, thiadiazolyl, oxadiazolyl, pyridinyl, pyridazinyl, pyrazinyl, or triazinyl;

phenyl(C₁–C₆ alkyl)-, phenyl(C₂–C₆ alkenyl)- or phenyl (C₂–C₆ alkynyl)-optionally substituted in the phenyl ring;

cycloalkyl(C₁–C₆ alkyl)-, cycloalkyl(C₂–C₆ alkenyl)- or cycloalkyl(C₂–C₆ alkynyl)-optionally substituted in the cycloalkyl ring;

heterocyclyl(C₁–C₆ alkyl)-, heterocyclyl(C₂–C₆ alkenyl)- or heterocyclyl(C₂–C₆ alkynyl)-optionally substituted in the heterocyclyl ring.

10. The method of claim 1 wherein R₄ is: methyl, ethyl, n-propyl, iso-propyl, cyclopropyl, cyclobutyl, cyclopentyl, cyclohexyl, 2-phenylcycloprop-1-yl, benzyl, biphenyl-2-yl, biphenyl-3-yl, biphenyl-4-yl, 2-methoxyphenyl, 3-methoxyphenyl, 4-methoxyphenyl, 2,3-dimethoxyphenyl, 2,4-dimethoxyphenyl, 3,4-dimethoxyphenyl, 2-phenoxyphenyl, 3-phenoxyphenyl, 4-phenoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-aminophenyl, 3-aminophenyl, 4-aminophenyl, 2-acetamidophenyl, 3-acetamidophenyl, 4-acetamidophenyl, 2-N,N-dimethylaminophenyl, 3-N,N-dimethylaminophenyl, 4-N,N-dimethylaminophenyl, 2-methanesulfonamidophenyl, 3-methanesulfonamidophenyl, 4-methanesulfonamidophenyl, 2-hydroxyphenyl, 3-hydroxyphenyl, 4-hydroxyphenyl, 2,3-dihydroxyphenyl, 2,4-dihydroxyphenyl, 3,4-dihydroxyphenyl, 2-thiophenolyl, 3-thiophenolyl, 4-thiophenolyl, 2-thioanisolyl, 3-thioanisolyl, 4-thioanisolyl, 1-naphthyl, 2-naphthyl, furan-2-yl, thien-2-yl, pyrrol-2-yl, 1-methylpyrrol-2-yl, imidazol-2-yl, 1-methylimidazol-2-yl, thiazol-2-yl, 5-phenylpyrrol-2-yl, 5-phenylfuran-2-yl, 5-phenylthien-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 1,3,4-thiadiazol-2-yl, pyridin-2-yl, pyridin-3-yl, pyridin-4-yl, N-oxides of pyridin-2-yl pyridin-3-yl and pyridin-4-yl, indol-2-yl, indol-3-yl, 1-methylindol-2-yl, 1-methylindol-3-yl, benzimidazol-2-yl, 1-methylbenzimidazol-2-yl, pyrazin-2-yl, 1,2-pyridazin-3-yl, 1,3-pyrimidin-2-yl, benzo[b]thien-2-yl, benzo[b]thien-3-yl, benzo[b]furan-2-yl, benzo[b]furan-3-yl, isoxazol-5-yl, quinolin-2-yl, quinolin-3-yl, isoquinolin-2-yl, isoquinolin-3-yl, 2-oxo-2-phenylethyl, diphenylmethyl, 4-N-methylaminophenyl, 4-N,N-dimethylcarboxamidophenyl, and 4-carboxyphenyl.

11. The method of claim 1 wherein R₄ is a phenyl group which is substituted by one of the following:

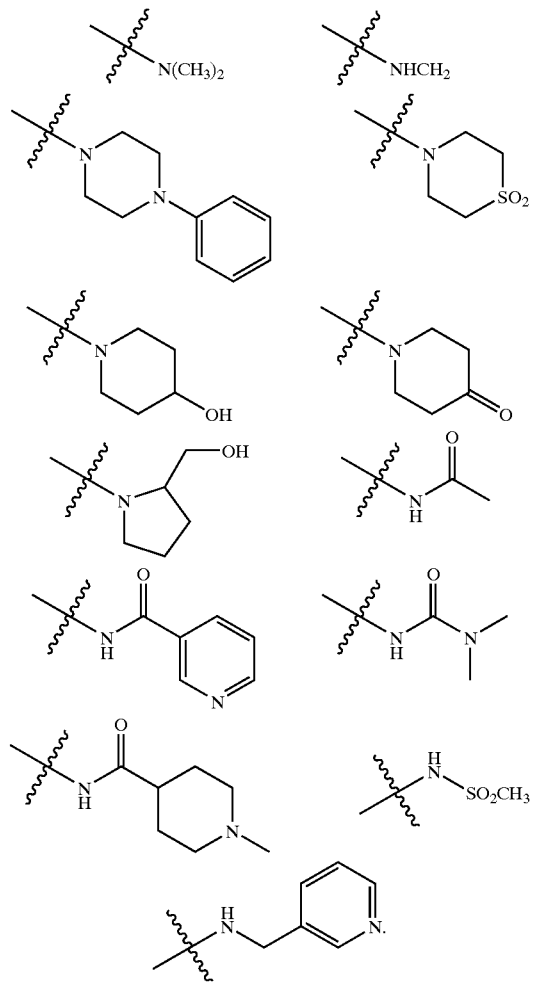

12. A compound for the treatment of bacterial or protozoal infections in humans and non-human mammals comprising a compound of formula (I) or a pharmaceutically or veterinarily acceptable salt, hydrate or solvate thereof:

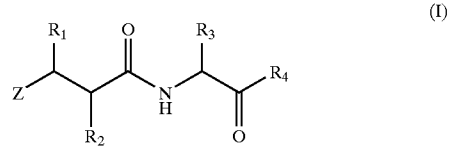

wherein:

Z represents a radical of formula —N(OH)CH(=O) or formula —C(=O)NH(OH);

$R_1$ represents hydrogen, methyl or trifluoromethyl, or, except when Z is a radical of formula —N(OH)CH(=O), a hydroxy or amino group;

$R_2$ represents a group $R_{10}$—(X)$_n$—(ALK)$_m$— wherein
  $R_{10}$ represents hydrogen, or a $C_1$–$C_6$ alkyl, $C_2$–$C_6$ alkenyl, $C_2$–$C_6$ alkynyl, cycloalkyl, aryl, or heterocyclyl group, any of which may be unsubstituted or substituted by ($C_1$–$C_6$)alkyl, ($C_1$–$C_6$)alkoxy, hydroxy, mercapto, ($C_1$–$C_6$)alkylthio, amino, halo (including fluoro, chloro, bromo and iodo), trifluoromethyl, cyano, nitro, oxo, —COOH, —CONH$_2$, —COOR$^A$, NHCOR$^A$, —CONHR$^A$, —NHR$^A$, —NR$^A$R$^B$, or —CONR$^A$R$^B$ wherein R$^A$ and R$^B$ are independently a ($C_1$–$C_6$)alkyl group and
  ALK represents a straight or branched divalent $C_1$–$C_6$ alkylene, $C_2$–$C_6$ alkenylene, or $C_2$–$C_6$ alkynylene radical, and may be interrupted by one or more non-adjacent —NH—, —O— or —S— linkages,
  X represents —NH—, —O— or —S—, and
  m and n are independently 0 or 1;

$R_3$ represents the side chain of a natural or non-natural alpha amino acid; and when Z represents a radical of formula —N(OH)CH(=O):

$R_4$ represents a radical $R_5$—(ALK)$_p$— wherein ALK is as defined in relation to $R_2$, p is 0 or 1, and $R_5$ represents hydrogen, or a $C_1$–$C_6$ alkyl, $C_2$–$C_6$ alkenyl, $C_2$–$C_6$ alkynyl, cycloalkyl, aryl, or heterocyclyl group any of which
  (i) may be substituted by a group selected from ($C_1$–$C_6$) alkyl, phenyl, benzyl, ($C_1$–$C_6$)alkoxy, phenoxy, hydroxy, mercapto, ($C_1$–$C_6$)alkylthio, amino, halo, trifluoromethyl, cyano, nitro, oxo, —COOH, —SO$_2$H, —CONH$_2$, —SO$_2$NH$_2$, —COR$^A$, —SOR$^A$, —SO$_2$R$^A$, —SO$_2$R$^A$, —COOR$^A$, —CONHR$^A$, —SO$_2$NHR$^A$, —NHCOR$^A$, —NHSO$_2$R$^A$, and —NHR$^A$, wherein R$^A$ is ($C_1$–$C_6$)alkyl, cycloalkyl, phenyl, 2-, 3- or 4-pyridyl, N- or 2-, 3- or 4-piperidyl, N- or 2- or 3-piperazyl group; or
  (ii) may be substituted by —NR$^A$R$^B$, —CONR$^A$R$^B$ or —SO$_2$NR$^A$R$^B$, wherein R$^A$ and R$^B$ are independently
  ($C_1$–$C_6$)alkyl, cycloalkyl, phenyl, 2-, 3- or 4-pyridyl, N- or 2-, 3- or 4-piperidyl, N- or 2- or 3-piperazyl group,
or when taken together with the N atom to which they are attached R$^A$ and R$^B$ form a 5 to 7 membered aromatic or non-aromatic ring, which ring (a) may contain additional heteroatoms selected from N, O and S, and in which any S atom may be oxidised as a sulphonyl or sulphoxide, and (b) may be substituted on a ring carbon or heteroatom by one or more of the substituents listed under (i) above; and when Z represents a radical of formula —C(=O)NH(OH):

$R_4$ represents a radical $R_5$—(ALK)$_p$— wherein ALK is as defined in relation to $R_2$, p is 0 or 1, and $R_5$ represents hydrogen, or a $C_{1-6}$ alkyl, $C_2$–$C_6$ alkenyl, $C_2$–$C_6$ alkynyl, cycloalkyl, aryl, or heterocyclyl group which is substituted by —NR$^A$R$^B$, —CONR$^A$R$^B$ or —SO$_2$NR$^A$R$^B$, wherein R$^A$ and R$^B$ taken together with the N atom to which they are attached form a 5 to 7 membered aromatic or non-aromatic ring, which ring (a) may contain additional heteroatoms selected from N, O and S, and in which any S atom may be oxidised as a sulphonyl or sulphoxide, and (b) may be substituted by a group selected from ($C_1$–$C_6$)alkyl, phenyl, benzyl, ($C_1$–$C_6$)alkoxy, phenoxy, hydroxy, mercapto, ($C_1$–$C_6$)alkylthio, amino, halo, trifluoromethyl, cyano, nitro, oxo, —COOH, —SO$_2$H, —CONH$_2$, —SO$_2$NH$_2$, —COR$^A$, —SOR$^A$, —SO$_2$R$^A$, —SO$_2$R$^A$, —COOR$^A$, —CONHR$^A$, —SO$_2$NHR$^A$, —NHCOR$^A$, —NHSO$_2$R$^A$, and —NHR$^A$, wherein R$^A$ is $C_{1-6}$)alkyl, cycloalkyl, phenyl, 2-, 3- or 4-pyridyl, N- or 2-, 3- or 4-piperidyl, N- or 2- or 3-piperazyl group.

13. The compound of claim 12 wherein $R_1$ is hydrogen.

14. The compound of claim 12 wherein $R_2$ is:
  optionally substituted $C_1$–$C_8$ alkyl, $C_3$–$C_6$ alkenyl, $C_3$–$C_6$ alkynyl or cycloalkyl;
  phenyl($C_1$–$C_6$ alkyl)-, phenyl($C_3$–$C_6$ alkenyl)- or phenyl ($C_3$–$C_6$ alkynyl)-optionally substituted in the phenyl ring;
  cycloalkyl($C_1$–$C_6$ alkyl)-, cycloalkyl($C_3$–$C_6$ alkenyl)- or cycloalkyl($C_3$–$C_6$ alkynyl)-optionally substituted in the cycloalkyl ring;
  heterocyclyl($C_1$–$C_6$ alkyl)-, heterocyclyl($C_3$–$C_6$ alkenyl)- or heterocyclyl($C_3$–$C_6$ alkynyl)-optionally substituted in the heterocyclyl ring; or
  $CH_3(CH_2)_pO(CH_2)_q$— or $CH_3(CH_2)_pS(CH_2)_q$—, wherein p is 0, 1, 2 or 3 and q is 1, 2 or 3.

15. The compound of claim 12 wherein $R_2$ is methyl, ethyl, n- or iso-propyl, n- and iso-butyl, n-pentyl, iso-pentyl, 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, or 4-methoxybenzyl.

16. The compound of claim 12 wherein $R_2$ is n-propyl, n-butyl, n-pentyl, or cyclopentylmethyl.

17. The compound of claim 12 wherein $R_3$ is:
  the characterising group of a natural α amino acid or 4-methoxyphenylmethyl, in which any functional group may be protected, any amino group may be acylated and any carboxyl group present may be amidated; or
  a group —(Alk)$_n$R$_9$ where Alk is a ($C_1$–$C_6$)alkylene or ($C_2$–$C_6$)alkenylene group optionally interrupted by ne or more —O—, or —S— atoms or —N(R$_{12}$)— groups where $R_{12}$ is a hydrogen atom or a ($C_1$–$C_6$)alkyl group, n is 0 or 1, and R$_9$ is hydrogen or an optionally substituted phenyl, aryl, heterocyclyl, cycloalkyl or cycloalkenyl group or (only when n is 1) R$_9$ may additionally be hydroxy, mercapto, ($C_1$–$C_6$)alkylthio, amino, halo, trifluoromethyl, nitro, —COOH, —CONH$_2$, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$–$C_6$)alkyl group; or
  a benzyl group substituted in the phenyl ring by a group of formula —OCH$_2$COR$_8$ where R$_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino; or
  a heterocyclic($C_1$–$C_6$)alkyl group, either being unsubstituted or mono- or di-substituted in ihe heterocyclic ring with halo, nitro, carboxy, $(C_1-C_6)$alkoxy, cyano, $(C_1-C_6)$alkahioyl, trifluoromethyl $(C_1-C_6)$alkyl, hydroxy, formyl, amino, $(C_1-C_6)$alkylamino, di-$(C_1-C_6)$alkylamino, mercapto, $(C_1-C_6)$alkylthio, hydroxy$(C_1-C_6)$alkyl, mercapto$(C_1-C_6)$alkyl or $(C_1-C_6)$alkylphenylmethyl; or a group —$CR_aR_bR_c$ in which:
each of $R_a$, $R_b$ and $R_c$ is independently hydrogen, $(C_1-C_6)$alkyl, $(C_2-C_6)$alkenyl, $(C_2-C_6)$alkynyl, phenyl$(C_1-C_6)$alkyl, $(C_3-C_8)$cycloalkyl; or $R_c$ is hydrogen and $R_a$ and $R_b$ are independently phenyl or heteroaryl such as pyridyl; or $R_c$ is hydrogen, $(C_1-C_6)$alkyl, $(C_2-C_6)$alkenyl, $(C_2-C_6)$alkynyl, phenyl$(C_1-C_6)$alkyl, or $(C_3-C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently $(C_1-C_6)$alkyl, $(C_2-C_6)$alkenyl, $(C_2-C_6)$alkynyl, phenyl$(C_1-C_6)$alkyl, or a group as defined for $R_c$ below other than hydrogen, or $R_a$ and $R_b$ together with the carbon atom to which they are attached form a cycloalkyl or heterocyclic ring, and R, is hydrogen, —OH, —SH, halogen, —CN, —$CO_2R$, $(C_1-C_4)$perfluoroalkyl, —$CH_2OH$, —$CO_2(C_1-C_6)$alkyl, —$O(C_1-C_6)$alkyl, —$O(C_2-C_6)$alkenyl, —$S(C_1-C_6)$alkyl, —SO$(C_1-C_6)$alkyl, —$SO_2(C_1-C_6)$alkyl, —$S(C_2-C_6)$alkenyl, —$SO(C_2-C_6)$alkenyl, —$SO_2(C_2-C_6)$alkenyl or a group —Q—W wherein Q represents a bond or —O—, —S—, —SO— or —$SO_2$— and W represents a phenyl, phenylalkyl, $(C_3-C_8)$cycloalkyl, $(C_3-C_8)$cycloalkylalkyl, $(C_4-C_8)$cycloalkenyl, $(C_4-C_8)$cycloalkenylalkyl, heteroaryl or heteroarylalkyl group, which group W may optionally be substituted by one or more substituents independently selected from, hydroxyl, halogen, —CN, —$CO_2H$, —$CO_2(C_1-C_6)$alkyl, —$CONH_2$, —$CONH(C_1-C_6)$alkyl, —$CONH(C_1-C_6$alkyl)$_2$, —CHO, —$CH_2OH$, $(C_1-C_4)$perfluoroalkyl, —$O(C_1-C_6)$alkyl, —$S(C_1-C_6)$alkyl, —$SO(C_1-C_6)$alkyl, —$SO_2(C_{1-6})$alkyl, —$NO_2$, —$NH_2$, —$NH(C_1-C_6)$alkyl, —$N((C_1-C_6)$alkyl)$_2$, —$NHCO(C_1-C_6)$alkyl, $(C_1-C_6)$alkyl, $(C_2-C_6)$alkenyl, $(C_2-C_6)$alkynyl, $(C_3-C_8)$cycloalkyl, $(C_4-C_8)$cycloalkenyl, phenyl or benzyl.

18. The compound of claim 12 wherein $R_3$ is methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxethyl, 2-carboxyethyl, 2-methylcarbamoylethyl, 2-carbamoylethyl, or 4-aminobutyl.

19. The compound of claim 12 wherein $R_3$ is tert-butyl.

20. The compound of claim 12 wherein $R_4$ is:
optionally substituted $C_1-C_8$ alkyl, $C_2-C_6$ alkenyl, $C_2-C_6$ alkynyl or cycloalkyl;
optionally substituted phenyl, biphenyl or naphthyl;
optionally substituted piperidinyl, cyclohexyl, cyclopentyl, oxazolyl, thiazepinyl, pyridinyl, pyrrolidinyl, pyrimidinyl, morpholinyl, piperazinyl, indolyl, thienyl, furanyl, pyrrolyl, imidazolyl, benzofuranyl, benzothienyl, benzimidazolyl, thiazolyl, benzothiazolyl, pyrazolyl, isoxazolyl, isothiazolyl, triazolyl, thiadiazolyl, oxadiazolyl, pyridinyl, pyridazinyl, pyrazinyl, or triazinyl, phenyl($C_1-C_6$ alkyl)-, phenyl($C_2-C_6$ alkenyl)- or phenyl ($C_2-C_6$ alkynyl)-optionally substituted in the phenyl ring;

cycloalkyl($C_1-C_6$ alkyl)-, cycloalkyl($C_2-C_6$ alkenyl)- or cycloalkyl($C_2-C_6$ alkynyl)-optionally substituted in the cycloalkyl ring;

heterocyclyl($C_1-C_6$ alkyl)-, heterocyclyl($C_2-C_6$ alkenyl)- or heterocyclyl($C_2-C_6$ alkynyl)-optionally substituted in the heterocyclyl ring.

21. The compound of claim 12 wherein $R_4$ is: methyl, ethyl, n-propyl, iso-propyl, cyclopropyl, cyclobutyl, cyclopentyl, cyclohexyl, 2-phenylcycloprop-1-yl, benzyl, biphenyl-2-yl, biphenyl-3-yl, biphenyl-4-yl, 2-methoxyphenyl, 3-methoxyphenyl, 4-methoxyphenyl, 2,3-dimethoxyphenyl, 2,4-dimethoxyphenyl, 3,4-dimethoxyphenyl, 2-phenoxyphenyl, 3-phenoxyphenyl, 4-phenoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-aminophenyl, 3-aminophenyl, 4-aminophenyl, 2-acetamidophenyl, 3-acetamidophenyl, 4-acetamidophenyl, 2-N,N-dimethylaminophenyl, 3-N,N-dimethylaminophenyl, 4-N,N-dimethylaminophenyl, 2-methanesulfonamidophenyl, 3-methanesulfonamidophenyl, 4-methanesulfonamidophenyl, 2-hydroxyphenyl, 3-hydroxyphenyl, 4-hydroxyphenyl, 2,3-dihydroxyphenyl, 2,4-dihydroxyphenyl, 3,4-dihydroxyphenyl, 2-thiophenolyl, 3-thiophenolyl, 4-thiophenolyl, 2-thioanisolyl, 3-thioanisolyl, 4-thioanisolyl, 1-naphthyl, 2-naphthyl, furan-2-yl, thien-2-yl, pyrrol-2-yl, 1-methylpyrrol-2-yl, imidazol-2-yl, 1-methylimidazol-2-yl, thiazol-2-yl, 5-phenylpyrrol-2-yl 5-phenylfuran-2-yl, 5-phenylthien-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 1,3,4-thiadiazol-2-yl, pyridin-2-yl pyridin-3-yl, pyidin-4-yl, N-oxides of pyridin-2-yl pyridin-3-yl and pyridin-4-yl, indol-2-yl, indol-3-yl, 1-methylindol-2-yl, 1-methylindol-3-yl, benzimidazol-2-yl, 1-methylbenzirmidazol-2-yl, pyrazin-2-yl, 1,2-pyridazin-3-yl, 1,3-pyrimidin-2-yl, benzo[b]thien-2-yl, benzo[b]thien-3-yl, benzo[b]furan-2-yl, benzo[b]furan-3-yl, isoxazol-5-yl, quinolin-2-yl, quinolin-3-yl, isoquinolin-2-yl, isoquinolin-3-yl, 2-oxo-2-phenylethyl, diphenylmnethyl, 4-N-methylaminophenyl, 4-N,N-dimethylcarboxamidophenyl, and 4-carboxyphenyl.

22. The compound of claim 12 wherein $R_4$ is a phenyl group which is substituted by one of the following:

 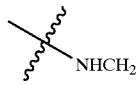

-continued

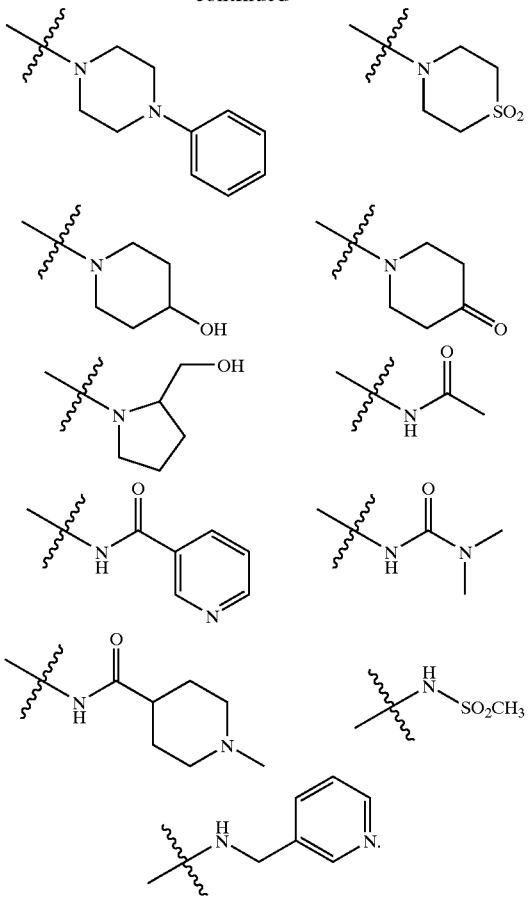

23. A pharmaceutical composition comprising a compound as claimed in claim 12 together with a pharmaceutically acceptable carrier.

24. A compound selected from the group consisting of:

2(R)-[(N-Formyl-N-hydroxyamino)-methyl]-hexanoic acid-(1'(S)-(4-fluorobenzoyl)-2',2'-dimethylpropyl) amide;

2(R)-[(N-Formyl-N-hydroxyamino)-methyl]-hexanoic acid-(1'(S)-(4-methoxybenzoyl 2',2'-dimethylpropyl) amide;

2(R)-[(N-Formyl-N-hydroxyamino)-methyl]-hexanoic acid-(1'(S)-cyclohexanecarbonyl-2'-methylpropyl) amide;

3-Cyclopentyl-2(R)-[(N-formyl-N-hydroxyamino)-methyl]-N-[1'(S)-(4-fluorobenzoyl)-2',2'-dimethylpropyl]propionamide;

3-Cyclopentyl-2(R)-[(N-formyl-N-hydroxyamino)-methyl]-N-[1'(S)-(4-methoxybenzoyl)-2',2'-dimethylpropyl]propionamide;

2(R)-[(N-Formyl-N-hydroxyamino)-methyl]-hexanoic acid-[2,2-dimethyl-1-(S)-(1-methyl-1H-imidazole-2-carbonyl)-propyl]-amide;

2(R)-[(N-Formyl-N-hydroxyamino)-methyl]-hexanoic acid-[2,2-dimethyl-1(S)-(pyridine-2-carbonyl)-propyl]-amide;

2(R)-[(N-Formyl-N-hydroxyamino)-methyl]-hexanoic acid-(1'(S)-(benzofuran-2-carbonyl)-2',2'-dimethylpropyl)amide;

N-[1(S)-(Benzofuran-2-carbonyl)-2,2-dimethylpropyl]-3'-cyclopentyl-2'(R)-[(N-formyl-N-hydroxyamino)-methyl]-propionamide;

2(R)-[(N-Benzyloxy-N-formylamino)-methyl]-hexanoic acid pentafluorophenyl ester;

2(R)-[(N-Formyl-N-hydroxyamino)-methyl]-hexanoic acid [1'-(2,4-dimethoxy-benzoyl)-2',2'-dimethylpropyl]-amide;

2(R)-[(N-Formyl-N-hydroxyamino)-methyl]-hexanoic acid [1'(S)-(4-hydroxy-benzoyl)-2',2'-dimethylpropyl]-amide;

2(R)-[(N-Benzyloxy-N-formylamino)-methyl]-3-cyclopentyl-propionic acid;

2(S)-tert-Butoxycarbonylamino-3,3-dimethyl-butyric acid pentafluorophenyl ester;

2(R)-[(N-Formyl-N-hydroxyamino)-methyl]-hexanoic acid-(1'(S)-tert-butyl-2'-oxo-3'-pyridin-2-yl-propyl) amide;

2(R)-[(N-Formyl-N-hydroxyamino)-methyl]-hexanoic acid [1'(S)-(4-methanesulfonyl-benzoyl)-2',2'-dimethyl-propyl]amide;

3-Cyclopentyl-2(S)-[(N-formyl-N-hydroxyamino)-methyl]-N-[1'(R)-(4-methoxybenzoyl)-2',2'-dimethylpropyl]propionamide;

2(R)-[(N-Formyl-N-hydroxyamino)-methyl]-hexanoic acid-(1'(S)-(furan-2-carbonyl)-2',2'-dimethylpropyl) amide;

2(R)-[(N-Formyl-N-hydroxyamino)-methyl]-hexanoic acid-(2',2'-dimethyl-1'(S)-(1-methyl-1H-pyrrole-2-carbonyl)-propyl)amide;

2(R)-[(N-Formyl-N-hydroxyamino)-methyl]-hexanoic acid-(1'(S)-(4-aminobenzoyl)-2',2'-dimethylpropyl) amide;

2(R)-[(N-Formyl-N-hydroxyamino)-methyl]-hexanoic acid-(2',2'-dimethyl-1'(S)-[4-(2,2,2-trifluoroacetylamino)-benzoyl]-propyl)amide;

2(R)-[(N-Formyl-N-hydroxyamino)-methyl]-hexanoic acid-(1'(S)-(4-acetylaminobenzoyl)-2',2'-dimethylpropyl)amide;

2(R)-[(N-Formyl-N-hydroxyamino)-methyl]-hexanoicacid-(1'(S)-(4-methanesulfonyl-aminobenzoyl)-2',2'-dimethylpropyl)amide;

2(R)-[(N-Formyl-N-hydroxyamino)-methyl]-hexanoic acid-(2',2'-dimethyl-1'(S)-(4-morpholin-4-ylbenzoyl)-propyl)amide;

2(R)-[(N-Formyl-N-hydroxyamino)-methyl]-hexanoic acid-(1'(S)-[4-(4-benzylpiperazin-1-yl)-benzoyl]-2',2'-dimethylpropyl)amide;

2(R)-[(N-Formyl-N-hydroxyamino)-methyl]-hexanoic acid-(2',2'-dimethyl-1'(S)-(4-piperazin-1-yl-benzoyl)-propyl)amide;

2(R)-[(N-Formyl-N-hydroxyamino)-methyl]-hexanoic acid-(2',2'-dimethyl-1'(S)-[4-(4-methylpiperazin-1-yl)-benzoyl]-propyl)amide;

2(R)-[(N-Formyl-N-hydroxyamino)-methyl]-hexanoic acid-(2',2'-dimethyl-1'(S)-[4-(4-pyrimidin-2-yl-piperazin-1-yl)-benzoyl]-propyl)amide;

2(R)-[(N-Formyl-N-hydroxyamino)-methyl]-hexanoic acid-(2',2'-dimethyl-1'(S)-{4-[4-(1,4,5,6-tetrahydropyrimidin-2-yl)-piperazin-1-yl]-benzoyl}-propyl)amide;

2(R)-[(N-Formyl-N-hydroxyamino)-methyl]-hexanoic acid-(1'(S)-(4-dipropylaminobenzoyl)-2',2'-dimethylpropyl)amide;

2(R)-[(N Formyl-N-hydroxyamino)-methyl]-hexanoic acid-(2',2'-dimethyl-1'(S)-(4-propylaminobenzoyl)-propyl)amide;

2(R)-[(N-Formyl-N-hydroxyamino)-methyl]-hexanoic acid-(1'(S)-acetyl-2',2'-dimethyl-propyl)amide; and 2(R)-[(N-Formyl-N-hydroxyamino)-methyl]-hexanoic acid-(1'(S)-benzoyl-2',2'-dimethyl-propyl)amide.

* * * * *

UNITED STATES PATENT AND TRADEMARK OFFICE
CERTIFICATE OF CORRECTION

PATENT NO. : 6,716,878 B1
DATED : April 6, 2004
INVENTOR(S) : Richard Simon Todd et al.

It is certified that error appears in the above-identified patent and that said Letters Patent is hereby corrected as shown below:

Column 73,
Line 27, please replace "R," with -- $R_c$ --
Line 28, please replace "—$CO_2R$" with -- $CO_2H$ --

Column 74,
Line 46, please replace "5-phenylpyrrol-2-yl 5-phenylfuran-2-yl" with
-- 5-phenylpyrrol-2-yl, 5-phenylfuran-2-yl --
Line 50, please replace "pyridine-2-yl pyridine-3-yl" with
-- pyridine-2-yl, pyridine-3-yl --

Column 76,
Line 59, please replace "N Formyl" with -- N-Formyl --

Signed and Sealed this

Twenty-second Day of March, 2005

JON W. DUDAS
*Director of the United States Patent and Trademark Office*